US007205139B2

(12) United States Patent
Moore et al.

(10) Patent No.: US 7,205,139 B2

(45) Date of Patent: Apr. 17, 2007

(54) TISSUE PLASMINOGEN ACTIVATOR-LIKE PROTEASE

(75) Inventors: Paul A. Moore, North Bethesda, MD (US); Steven M. Ruben, Brookeville, MD (US); Reinhard Ebner, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 378 days.

(21) Appl. No.: 10/894,043

(22) Filed: Jul. 20, 2004

(65) Prior Publication Data

US 2004/0265968 A1 Dec. 30, 2004

Related U.S. Application Data

(60) Division of application No. 10/057,951, filed on Jan. 29, 2002, now Pat. No. 6,815,534, which is a division of application No. 09/411,977, filed on Oct. 4, 1999, now Pat. No. 6,372,473, which is a continuation-in-part of application No. 09/084,491, filed on May 27, 1998, now abandoned.

(60) Provisional application No. 60/048,000, filed on May 28, 1997.

(51) Int. Cl.

| | |
|---|---|
| ***C12N 9/48*** | (2006.01) |
| ***C12N 9/68*** | (2006.01) |
| ***C12N 1/21*** | (2006.01) |
| ***C12N 5/06*** | (2006.01) |
| ***C12N 15/63*** | (2006.01) |
| ***C07H 21/04*** | (2006.01) |

(52) U.S. Cl. .................. 435/212; 435/217; 435/252.3; 435/320.1; 435/325; 435/455; 536/23.2; 536/23.4; 536/23.5

(58) Field of Classification Search ..................... None
See application file for complete search history.

(56) References Cited

U.S. PATENT DOCUMENTS 6,372,473 B1 4/2002 Moore et al.

FOREIGN PATENT DOCUMENTS

| | | |
|---|---|---|
| DE | 19817946 A1 | 10/1999 |
| JP | 10265498 | 10/1998 |
| WO | WO 98/00539 | 1/1998 |
| WO | WO 98/54199 A1 | 12/1998 |
| WO | WO 99/06548 | 2/1999 |
| WO | WO 99/06553 | 2/1999 |
| WO | WO 99/11788 | 3/1999 |
| WO | WO 00/58473 A2 | 10/2000 |

OTHER PUBLICATIONS

Genbank Accession No. N29083, "yx41f01.r1 Soares melanocyte 2NbHM *Homo sapiens* cDNA clone IMAGE:264313 5', MRNA sequence" (Jan. 1996).

Genbank Accession No. N56924, "yy82d03.s1 Soares_multiple_sclerosis_2NbHMSP *Homo sapiens* cDNA clone IMAGE:280037 3', MRNA sequence" (Feb. 1996).

Genbank Accession No. AA040339, "zk47g10.r1 Soares_pregnant_uterus_NbHPU *Homo sapiens* cDNA clone IMAGE:486018 5', MRNA sequence" (Aug. 1996).

Genbank Accession No. AA010038, "ze16e05.s1 Soares_fetal_heart_NbHH19W *Homo sapiens* cDNA clone IMAGE:359168 3', MRNA sequence" (Jul. 1996).

Genbank Accession No. R59582, "yh02b02.s1 Soars infant brain 1NIB *Homo sapiens* cDNA clone IMAGE:41998 3', MRNA sequence" (May 1995).

Genbank Accession No. H27162, "y166h03.r1 Soares breast 3NbHBst *Homo sapiens* cDNA clone IMAGE:163253 5', MRNA sequence" (Jul. 1995).

Genbank Accession No. AA007433, "zh95g09.r1 Soares_fetal_liver_spleen_1NFLS_S1 *Homo sapiens* cDNA clone IMAGE:429088 5', MRNA sequence" (Jun. 1996).

Genbank Accession No. AA384820, "EST98381 Thyroid *Homo sapiens* cDNA 5' end, MRNA sequence" (Apr. 1997).

Genbank Accession No. AA299895, "EST12506 Uterus tumor I *Homo sapiens* cDNA 3' end, MRNA sequence" (Apr. 1997).

Genbank Accession No. W39554, "zc18g07.r1 Soares_parathyroid_tumor_NbHPA *Homo sapiens* cDNA clone IMAGE:322716 5', MRNA sequence" (May 1996).

Genbank Accession No. H27370, "y165e11.r1 Soares breast 3NbHBst *Homo sapiens* cDNA clone IMAGE:163148 5', MRNA sequence" (Jul. 1995).

Genbank Accession No. W61188, "zd31d09.r1 Soares_fetal_heart_NbHH19W *Homo sapiens* cDNA clone IMAGE:342257 5', MRNA sequence" (May 1996).

Genbank Accession No. R59640, "yh02b02.r1 Soares infant brain 1NIB *Homo sapiens* cDNA clone IMAGE:41998 5' similar to SP:HGFL_MOUSE P26928 Hepatocyte Growth Factor-Like Protein Precursor;, MRNA sequence" (May 1995).

Genbank Accession No. Z44818, "HSC29H051 normalized infant brain cDNA *Homo sapiens* cDNA clone c-29h05, MRNA sequence" (Nov. 1994).

Genbank Accession No. F07547, "HSC29H061 normalized infant brain cDNA *Homo sapiens* cDNA clone c-29h06, MRNA sequence" (Feb. 1995).

Genbank Accession No. R80298, "yi92e07.r1 Soares placenta Nb2HP *Homo sapiens* cDNA clone IMAGE:146724 5', MRNA sequence" (Jun. 1995).

Genbank Accession No. W61189, "zd31d09.s1 Soares_fetal_heart_NbHH19W *Homo sapiens* cDNA clone IMAGE:342257 3', MRNA sequence" (May 1996).

(Continued)

*Primary Examiner*—Elizabeth Slobodyansky

(57) ABSTRACT

The present invention relates to a novel t-PALP protein which is a member of the serine protease family. In particular, isolated nucleic acid molecules are provided encoding the human t-PALP protein. t-PALP polypeptides are also provided as are vectors, host cells and recombinant methods for producing the same. The invention further relates to screening methods for identifying agonists and antagonists of t-PALP activity. Also provided are diagnostic methods for detecting circulatory system-related disorders and therapeutic methods for treating circulatory system-related disorders.

20 Claims, 8 Drawing Sheets

OTHER PUBLICATIONS

Genbank Accession No. F13082, "HSC3ID071 normalized infant brain cDNA *Homo sapiens* cDNA clone c-3id07, MRNA sequence" (Mar. 1995).

Genbank Accession No. AA040340, "zk47g10.s1 Soares_pregnant_uterus_NbHPU *Homo sapiens* cDNA clone IMAGE:486018 3', MRNA sequence" (Aug. 1996).

Genbank Accession No. N31943, "yy22fl1.s1 Soares melanocyte 2NbHM *Homo sapiens* cDNA clone IMAGE:272013 3', MRNA sequence" (Jan. 1996).

Genbank Accession No. W15393, "zc18g07.s1 Soares_parathyroid_tumor_NbHPA *Homo sapiens* cDNA clone IMAGE:322716 3', MRNA sequence" (May 1996).

Genbank Accession No. AA381441, "EST94518 Activated T-cells I *Homo sapiens* cDNA 5' end, MRNA sequence" (Apr. 1997).

Genbank Accession No. F10676, "HSC3ID072 normalized infant brain cDNA *Homo sapiens* cDNA clone c-3id07 3', MRNA sequence" (Feb. 1995).

Genbank Accession No. AA340555, "EST45776 Fetal kidney I *Homo sapiens* cDNA 3' end, MRNA sequence" (Apr. 1997).

Genbank Accession No. H93584, "yw54c10.r1 Soares_placenta_8to9weeks_2NbHP8to9W *Homo sapiens* cDNA clone IMAGE:256050 5' similar to contains Alu repetitive element;, MRNA sequence" (Dec. 1995).

Genbank Accession No. N42779, "yy22fl1.r1 Soares melanocyte 2NbHM *Homo sapiens* cDNA clone IMAGE:272013 5', MRNA sequence" (Jan. 1996).

Genbank Accession No. Z40604, "HSC29H062 normalized infant brain cDNA *Homo sapiens* cDNA clone c-29h06 3', MRNA sequence" (Nov. 1994).

Genbank Accession No. AA007565, "zh95g09.s1 Soares_fetal_liver_spleen_1NFLS_S1 *homo sapiens* cDNA clone IMAGE:429088 3' similar to contains Alu repetitive element;, MRNA sequence" (Jun. 1996).

Genbank Accession No. AA174274, "mo97b10.r1 Stratagene mouse testis (#937308) Mus musculus cDNA clone IMAGE:567643 5', MRNA sequence" (Oct. 1996).

Genbank Accession No. AA103132, "mo17d06.r1 Life Tech mouse embryo 13 5dpc 10666014 *Mus musculus* cDNA clone IMAGE:553835 5', MRNA sequence" (Oct. 1996).

Genbank Accession No. D31562, "HUML1833 Human fetal lung *Homo sapiens* cDNA 5', MRNA sequence" (Feb. 1995).

Genbank Accession No. F03785, "HSC29H052 normalized infant brain cDNA *Homo sapiens* cDNA clone c-29h05 3', MRNA sequence" (Feb. 1995).

Genbank Accession No. AA372863, "EST84827 Colon adenocarcinoma IV *Homo sapiens* cDNA 5' end, MRNA sequence" (Apr. 1997).

Genbank Accession No. G24591, "human STS WI-14622, sequence tagged site" (May 1996).

Genbank Accession No. G24430, "human STS WI-12936, sequence tagged site" (May 1996).

Genbank Accession No. G20845, "human STS A006I21, sequence tagged site" (Jul. 1996).

Genbank Accession No. AC002073, "Human PAC clone RP3-515N1 from 22q11.2-q22, complete sequence" (Feb. 2000).

Genbank Accession No. AAB54054, "Putative gene. Genscan predictions confirmed by EST splicing" (Feb. 2000).

Database SPTREMBL 12, Accession No. O00318, Du et al., Putative Protein.

Abaza et al., "Effects of amino acid substitutions outside an antigenic site on protein binding to monoclonal antibodies of predetermined specificity obtained by peptide immunization," J. Protein Chem. 11(6):687-98 (1992).

Colman, P.M., "Effects of amino acid sequence changes on antibody-antigen interactions," Res. Immumol. 145(1):33-36 (1994).

Lederman et al., "A single amino acid substitution in a common African allele of the CD4 molecule ablates binding of the monoclonal antibody, OKT4," Mol. Immunol. 28(11):1171-81 (1991).

Li et al., "beta-Endorphin omission analogs: dissociation of immunoreactivity from other biological activities," Proc. Natl. Acad. Sci. U.S.A. 77(6):3211-3214 (1980).

Pennica et al., "Cloning and expression of human tissue-type plasminogen activator cDNA in *E. coli*", *Nature* 301(5897):214-21 (1983).

```
1    TTACCAGAACAGCATAACAAGGGCAGGTCTGACTGCAAGCTGGGACTGGGAGGCAGAGCC   60

61   GCCGCCAAGGGGGCCTCGGTTAAACACTGGTCGTTCAATCACCTGCAAGACGAAGAGGCA   120

121  AGGATGCTGTTGGCCTGGGTACAAGCATTCCTCGTCAGCAACATGCTCCTAGCAGAAGCC   180
1       M  L  L  A  W  V  Q  A  F  L  V  S  N  M  L  L  A  E  A     19

181  TATGGATCTGGAGGCTGTTTCTGGGACAACGGCCACCTGTACCGGGAGGACCAGACCTCC   240
20   Y  G  S  G  G  C  F  W  D  N  G  H  L  Y  R  E  D  Q  T  S     39

241  CCCGCGCCGGGCCTCCGCTGCCTCAACTGGCTGGACGCGCAGAGCGGGCTGGCCTCGGCC   300
40   P  A  P  G  L  R  C  L  N  W  L  D  A  Q  S  G  L  A  S  A     59

301  CCCGTGTCGGGGGCCGGCAATCACAGTTACTGCCGAAACCCGGACGAGGACCCGCGCGGG   360
60   P  V  S  G  A  G  N  H  S  Y  C  R  N  P  D  E  D  P  R  G     79

361  CCCTGGTGCTACGTCAGTGGCGAGGCCGGCGTCCCTGAGAAACGGCCTTGCGAGGACCTG   420
80   P  W  C  Y  V  S  G  E  A  G  V  P  E  K  R  P  C  E  D  L     99

421  CGCTGTCCAGAGACCACCTCCCAGGCCCTGCCAGCCTTCACGACAGAAATCCAGGAAGCG   480
100  R  C  P  E  T  T  S  Q  A  L  P  A  F  T  T  E  I  Q  E  A     119

481  TCTGAAGGGCCAGGTGCAGATGAGGTGCAGGTGTTCGCTCCTGCCAACGCCCTGCCCGCT   540
120  S  E  G  P  G  A  D  E  V  Q  V  F  A  P  A  N  A  L  P  A     139

541  CGGAGTGAGGCGGCAGCTGTGCAGCCAGTGATTGGGATCAGCCAGCGGGTGCGGATGAAC   600
140  R  S  E  A  A  A  V  Q  P  V  I  G  I  S  Q  R  V  R  M  N     159

601  TCCAAGGAGAAAAAGGACCTGGGAACTCTGGGCTACGTGCTGGGCATTACCATGATGGTG   660
160  S  K  E  K  K  D  L  G  T  L  G  Y  V  L  G  I  T  M  M  V     179

661  ATCATCATTGCCATCGGAGCTGGCATCATCTTGGGCTACTCCTACAAGAGGGGGAAGGAT   720
180  I  I  I  A  I  G  A  G  I  I  L  G  Y  S  Y  K  R  G  K  D     199
```

FIG.1A

```
721  TTGAAAGAACAGCATGATCAGAAAGTATGTGAGAGGGAGATGCAGCGAATCACTCTGCCC  780
200  L  K  E  Q  H  D  Q  K  V  C  E  R  E  M  Q  R  I  T  L  P   219

781  TTGTCTGCCTTCACCAACCCCACCTGTGAGATTGTGGATGAGAAGACTGTCGTGGTCCAC  840
220  L  S  A  F  T  N  P  T  C  E  I  V  D  E  K  T  V  V  V  H   239

841  ACCAGCCAGACTCCAGTTGACCCTCAGGAGGGCAGCACCCCCCTTATGGGCCAGGCCGGG  900
240  T  S  Q  T  P  V  D  P  Q  E  G  S  T  P  L  M  G  Q  A  G   259

901  ACTCCTGGGGCCTGAGCCCCCCCAGTGGGCAGGAGCCCATGCAGACACTGGTGCAGGACA  960
260  T  P  G  A  *                                                 263

961  GCCCACCCTCCTACAGCTAGGAGGAACTACCACTTTGTGTTCTGGTTAAAACCCTACCAC  1020

1021 TCCCCCGCTTTTTTGGCGAATCCTAGTAAGAGTGACAGAAGCAGGTGGCCCTGTGGGCTG  1080

1081 AGGGTAAGGCTGGGTAGGGTCCTAACAGTGCTCCTTGTCCATCCCTTGGAGCAGATTTTG  1140

1141 TCTGTGGATGGAGACAGTGGCAGCTCCCACAGTGATGCTGCTGCTAAGGGCTTCCAAACA  1200

1201 TTGCCTGCACCCCTGGAACTGAACCAGGGATAGACGGGGAGCTCCCCCAGGCTCCTCTGT  1260

1261 GCTTTACTAAGATGGCTCAGTCTCCACTGTGGGCTTGAGTGGCATACACTGTTATTCATG  1320

1321 GTTAAGGTAAAGCAGGTCAAGGGATGGCATTGAAAAAATATATTTAGTTTTTAAAATATT  1380

1381 TGGGATGGAACTCCCTACTGACCTCTGACAACTGGAAACGAGTTTGTACTGAAGTCAGAA  1440

1441 CTTTGGGTTGGGAATGAGATCTAGGTTGTGGCTGCTGGTATGCTTCAGCTTGCTGGCAAT  1500

1501 GATGTGCCTTGACAACCGTGGGCCAGGCCTGGGCCCAGGGACTCTTCCTGTTTCATAAGG  1560
```

FIG.1B

1561 AAAGGAAGAATTGCACTGAGCATTCCACTTAGGAAGAGGATAGAGAAGGATCTGCTCCGC 1620

1621 CTTTGGCCACAGGAGCAGAGGCAGACCTGGGATGCCCCAGTTTCTCTTCAGGGATGGATA 1680

1681 GTGACCTGTCTTCATTTTGCACAGGTAAGAGAGTAGTTAGCTAACCTATGGGAATTATAC 1740

1741 TGTGGGGCCTTGTGAGCTGCTTCTAAGAGGCTAACCTGGAAACTAAGCTCAGAGGCAAGG 1800

1801 TAATAAAGCACTTCAGGGCTTGCTCCCCAAGTGGGCCTGATTTAGCAGGTGGTCTGCGGG 1860

1861 CGTCCAGGTCAGCACCTTCCTGTAGGGCACTGGGGCTAGGGTCACAGCCCCTAACTCATA 1920

1921 AAGCAATCAAAGAACCATTAGAAAGGGCTCATTAAGCCTTTTGGACACAGGACCCCAGAG 1980

1981 AGGAAAAAGTGACTTGCCCAAGGTCGTAAGCAAGCTACTGGCATGGCAAGAGCCCAGCTT 2040

2041 CCTGACGGAGCGCAACATTTCTCCACTGCACTGTGCTAGCAGCTCAGCAGGGCCTCTAAC 2100

2101 CTGTGATGTCACACTCAAGAGGCCTTGGCAGCTCCTAGCCATAGAGCTTCCTTTCCAGAA 2160

2161 CCCTTCCACTGCCCAATGTGGAGACAGGGGTTAGTGGGGCTTTCTATGGAGCCATCTGCT 2220

2221 TTGGGGACCTAGACCTCAGGTGGTCTCTTGGTGTTAGTGATGCTGGAGAAGAGAATATTA 2280

2281 CTGGTTTCTACTTTTCTATAAAGGCATTTCTCTATAAAAAAAAAAAAAA 2329

FIG.1C

```
                    .         .         .         .
  3 LAWVQAFLVSNMLLAEAY..GSGGCFWDNGHLYREDQTSPAPGLRCLNW. 49
    ..: .: . |::  ..|:  |.::|:::||  ||:.:. ...| .|| |
191 YVFKAGKYSSEFCSTPACSEGNSDCYFGNGSAYRGTHSLTESGASCLPWN 240

                .         .         .         .         .
 50 ........LDAQSGLASAPVSGAGNHSYCRNPDEDPRGPWCYV....... 84
            ..||.  :||.. | |.|.|||||:|:: |||.|
241 SMILIGKVYTAQN..PSAQALGLGKHNYCRNPDGDAK.PWCHVLKNRRLT 287

                .         .         .         .         .
 85 SGEAGVPEKRPCEDLRCPETTSQALPAFTTEIQE........ASEGPGAD 126
    .: .:||. ..|:  .:.:.  .  .:: .:|..        |.. .:::
288 WEYCDVPSCSTCGLRQYSQPQFRIKGGLFADIASHPWQAAIFAKHRRSPG 337

                .         .         .         .         .
127 E...........VQVFAPANALPARSEAAAVQPVIGISQRVRMNSKEK.. 163
    |           . ::.:|:.:..| .:  : .::| . ||  ...|.
338 ERFLCGGILISSCWILSAAHCFQERFPPHHLTVILGRTYRVVPGEEEQKF 387

                .         .         .         .         .
164 ........KDLGTLGYVLGITMMVIIIAIG....AGIILGYSYKRGKDL. 200
            |:::. .|  :|.:: :  . :    .: ::   : .. ||
388 EVEKYIVHKEFDDDTYDNDIALLQLKSDSSRCAQESSVVRTVCLPPADLQ 437

                .         .         .         .         .
201 .............KEQHDQKVCEREMQRITLPLSAFTNPTCEIVDEKTV. 236
                 |.:   ..:.  :.   :.| : ...|:: : ::||
438 LPDWTECELSGYGKHEALSPFYSERLKEAHVRLYPSSRCTSQHLLNRTVT 487

                .         .
237 ..VVHTSQTPVDPQEGSTPLMGQAGTPGA 263
      :: .::|. :..::. .  .|::..|:
488 DNMLCAGDTRSGGPQANLHDACQGDSGGP 516
```

FIG.2

TUMOR GROWTH OF t-PALP PROTEIN TRANSFECTANTS ON CAM

SEQUENCE LISTING

```
<160> NUMBER OF SEQ ID NOS: 31

<210> SEQ ID NO 1
<211> LENGTH: 2329
<212> TYPE: DNA
<213> ORGANISM: Homo sapiens
```

-continued

```
<220> FEATURE:
<221> NAME/KEY: sig_peptide
<222> LOCATION: (124)..(186)
<220> FEATURE:
<221> NAME/KEY: mat_peptide
<222> LOCATION: (187)..(912)
<220> FEATURE:
<221> NAME/KEY: CDS
<222> LOCATION: (124)..(915)

<400> SEQUENCE: 1

ttaccagaac agcataacaa gggcaggtct gactgcaagc tgggactggg aggcagagcc      60

gccgccaagg gggcctcggt taaacactgg tcgttcaatc acctgcaaga cgaagaggca     120

agg atg ctg ttg gcc tgg gta caa gca ttc ctc gtc agc aac atg ctc       168
    Met Leu Leu Ala Trp Val Gln Ala Phe Leu Val Ser Asn Met Leu
        -20                 -15                 -10

cta gca gaa gcc tat gga tct gga ggc tgt ttc tgg gac aac ggc cac       216
Leu Ala Glu Ala Tyr Gly Ser Gly Gly Cys Phe Trp Asp Asn Gly His
     -5              -1   1               5                  10

ctg tac cgg gag gac cag acc tcc ccc gcg ccg ggc ctc cgc tgc ctc       264
Leu Tyr Arg Glu Asp Gln Thr Ser Pro Ala Pro Gly Leu Arg Cys Leu
                 15                  20                  25

aac tgg ctg gac gcg cag agc ggg ctg gcc tcg gcc ccc gtg tcg ggg       312
Asn Trp Leu Asp Ala Gln Ser Gly Leu Ala Ser Ala Pro Val Ser Gly
             30                  35                  40

gcc ggc aat cac agt tac tgc cga aac ccg gac gag gac ccg cgc ggg       360
Ala Gly Asn His Ser Tyr Cys Arg Asn Pro Asp Glu Asp Pro Arg Gly
         45                  50                  55

ccc tgg tgc tac gtc agt ggc gag gcc ggc gtc cct gag aaa cgg cct       408
Pro Trp Cys Tyr Val Ser Gly Glu Ala Gly Val Pro Glu Lys Arg Pro
     60                  65                  70

tgc gag gac ctg cgc tgt cca gag acc acc tcc cag gcc ctg cca gcc       456
Cys Glu Asp Leu Arg Cys Pro Glu Thr Thr Ser Gln Ala Leu Pro Ala
 75                  80                  85                  90

ttc acg aca gaa atc cag gaa gcg tct gaa ggg cca ggt gca gat gag       504
Phe Thr Thr Glu Ile Gln Glu Ala Ser Glu Gly Pro Gly Ala Asp Glu
                 95                 100                 105

gtg cag gtg ttc gct cct gcc aac gcc ctg ccc gct cgg agt gag gcg       552
Val Gln Val Phe Ala Pro Ala Asn Ala Leu Pro Ala Arg Ser Glu Ala
            110                 115                 120

gca gct gtg cag cca gtg att ggg atc agc cag cgg gtg cgg atg aac       600
Ala Ala Val Gln Pro Val Ile Gly Ile Ser Gln Arg Val Arg Met Asn
        125                 130                 135

tcc aag gag aaa aag gac ctg gga act ctg ggc tac gtg ctg ggc att       648
Ser Lys Glu Lys Lys Asp Leu Gly Thr Leu Gly Tyr Val Leu Gly Ile
    140                 145                 150

acc atg atg gtg atc atc att gcc atc gga gct ggc atc atc ttg ggc       696
Thr Met Met Val Ile Ile Ile Ala Ile Gly Ala Gly Ile Ile Leu Gly
155                 160                 165                 170

tac tcc tac aag agg ggg aag gat ttg aaa gaa cag cat gat cag aaa       744
Tyr Ser Tyr Lys Arg Gly Lys Asp Leu Lys Glu Gln His Asp Gln Lys
                175                 180                 185

gta tgt gag agg gag atg cag cga atc act ctg ccc ttg tct gcc ttc       792
Val Cys Glu Arg Glu Met Gln Arg Ile Thr Leu Pro Leu Ser Ala Phe
            190                 195                 200

acc aac ccc acc tgt gag att gtg gat gag aag act gtc gtg gtc cac       840
Thr Asn Pro Thr Cys Glu Ile Val Asp Glu Lys Thr Val Val Val His
        205                 210                 215

acc agc cag act cca gtt gac cct cag gag ggc agc acc ccc ctt atg       888
Thr Ser Gln Thr Pro Val Asp Pro Gln Glu Gly Ser Thr Pro Leu Met
    220                 225                 230
```

-continued

```
ggc cag gcc ggg act cct ggg gcc tga gcccccccag tgggcaggag           935
Gly Gln Ala Gly Thr Pro Gly Ala
235                 240

cccatgcaga cactggtgca ggacagccca ccctcctaca gctaggagga actaccactt    995

tgtgttctgg ttaaaaccct accactcccc cgctttttg gcgaatccta gtaagagtga   1055

cagaagcagg tggccctgtg ggctgagggt aaggctgggt agggtcctaa cagtgctcct   1115

tgtccatccc ttggagcaga ttttgtctgt ggatggagac agtggcagct cccacagtga   1175

tgctgctgct aagggcttcc aaacattgcc tgcacccctg gaactgaacc agggatagac   1235

ggggagctcc cccaggctcc tctgtgcttt actaagatgg ctcagtctcc actgtgggct   1295

tgagtggcat acactgttat tcatggttaa ggtaaagcag gtcaagggat ggcattgaaa   1355

aaatatattt agtttttaaa atatttggga tggaactccc tactgacctc tgacaactgg   1415

aaacgagttt gtactgaagt cagaactttg ggttgggaat gagatctagg ttgtggctgc   1475

tggtatgctt cagcttgctg gcaatgatgt gccttgacaa ccgtgggcca ggcctgggcc   1535

cagggactct tcctgtttca taaggaaagg aagaattgca ctgagcattc cacttaggaa   1595

gaggatagag aaggatctgc tccgcctttg gccacaggag cagaggcaga cctgggatgc   1655

cccagtttct cttcagggat ggatagtgac ctgtcttcat tttgcacagg taagagagta   1715

gttagctaac ctatgggaat tatactgtgg ggccttgtga gctgcttcta agaggctaac   1775

ctggaaacta agctcagagg caaggtaata aagcacttca gggcttgctc cccaagtggg   1835

cctgatttag caggtggtct gcgggcgtcc aggtcagcac cttcctgtag ggcactgggg   1895

ctagggtcac agcccctaac tcataaagca atcaaagaac cattagaaag ggctcattaa   1955

gccttttgga cacaggaccc cagagaggaa aaagtgactt gcccaaggtc gtaagcaagc   2015

tactggcatg gcaagagccc agcttcctga cggagcgcaa catttctcca ctgcactgtg   2075

ctagcagctc agcagggcct ctaacctgtg atgtcacact caagaggcct tggcagctcc   2135

tagccataga gcttcctttc cagaaccctt ccactgccca atgtggagac aggggttagt   2195

ggggctttct atggagccat ctgctttggg gacctagacc tcaggtggtc tcttggtgtt   2255

agtgatgctg gagaagagaa tattactggt ttctactttt ctataaaggc atttctctat   2315

aaaaaaaaaa aaaa                                                     2329


<210> SEQ ID NO 2
<211> LENGTH: 263
<212> TYPE: PRT
<213> ORGANISM: Homo sapiens

<400> SEQUENCE: 2

Met Leu Leu Ala Trp Val Gln Ala Phe Leu Val Ser Asn Met Leu Leu
    -20                 -15                 -10

Ala Glu Ala Tyr Gly Ser Gly Gly Cys Phe Trp Asp Asn Gly His Leu
-5              -1   1               5                  10

Tyr Arg Glu Asp Gln Thr Ser Pro Ala Pro Gly Leu Arg Cys Leu Asn
            15                  20                  25

Trp Leu Asp Ala Gln Ser Gly Leu Ala Ser Ala Pro Val Ser Gly Ala
        30                  35                  40

Gly Asn His Ser Tyr Cys Arg Asn Pro Asp Glu Asp Pro Arg Gly Pro
     45                  50                  55

Trp Cys Tyr Val Ser Gly Glu Ala Gly Val Pro Glu Lys Arg Pro Cys
 60                  65                  70                  75
```

-continued

```
Glu Asp Leu Arg Cys Pro Glu Thr Thr Ser Gln Ala Leu Pro Ala Phe
                80                  85                  90

Thr Thr Glu Ile Gln Glu Ala Ser Glu Gly Pro Gly Ala Asp Glu Val
            95                  100                 105

Gln Val Phe Ala Pro Ala Asn Ala Leu Pro Ala Arg Ser Glu Ala Ala
        110                 115                 120

Ala Val Gln Pro Val Ile Gly Ile Ser Gln Arg Val Arg Met Asn Ser
    125                 130                 135

Lys Glu Lys Lys Asp Leu Gly Thr Leu Gly Tyr Val Leu Gly Ile Thr
140                 145                 150                 155

Met Met Val Ile Ile Ile Ala Ile Gly Ala Gly Ile Ile Leu Gly Tyr
                160                 165                 170

Ser Tyr Lys Arg Gly Lys Asp Leu Lys Glu Gln His Asp Gln Lys Val
            175                 180                 185

Cys Glu Arg Glu Met Gln Arg Ile Thr Leu Pro Leu Ser Ala Phe Thr
        190                 195                 200

Asn Pro Thr Cys Glu Ile Val Asp Glu Lys Thr Val Val Val His Thr
    205                 210                 215

Ser Gln Thr Pro Val Asp Pro Gln Glu Gly Ser Thr Pro Leu Met Gly
220                 225                 230                 235

Gln Ala Gly Thr Pro Gly Ala
                240


<210> SEQ ID NO 3
<211> LENGTH: 326
<212> TYPE: PRT
<213> ORGANISM: Homo sapiens

<400> SEQUENCE: 3

Tyr Val Phe Lys Ala Gly Lys Tyr Ser Ser Glu Phe Cys Ser Thr Pro
  1               5                  10                  15

Ala Cys Ser Glu Gly Asn Ser Asp Cys Tyr Phe Gly Asn Gly Ser Ala
            20                  25                  30

Tyr Arg Gly Thr His Ser Leu Thr Glu Ser Gly Ala Ser Cys Leu Pro
        35                  40                  45

Trp Asn Ser Met Ile Leu Ile Gly Lys Val Tyr Thr Ala Gln Asn Pro
     50                  55                  60

Ser Ala Gln Ala Leu Gly Leu Gly Lys His Asn Tyr Cys Arg Asn Pro
 65                  70                  75                  80

Asp Gly Asp Ala Lys Pro Trp Cys His Val Leu Lys Asn Arg Arg Leu
                85                  90                  95

Thr Trp Glu Tyr Cys Asp Val Pro Ser Cys Ser Thr Cys Gly Leu Arg
            100                 105                 110

Gln Tyr Ser Gln Pro Gln Phe Arg Ile Lys Gly Gly Leu Phe Ala Asp
        115                 120                 125

Ile Ala Ser His Pro Trp Gln Ala Ala Ile Phe Ala Lys His Arg Arg
    130                 135                 140

Ser Pro Gly Glu Arg Phe Leu Cys Gly Gly Ile Leu Ile Ser Ser Cys
145                 150                 155                 160

Trp Ile Leu Ser Ala Ala His Cys Phe Gln Glu Arg Phe Pro Pro His
                165                 170                 175

His Leu Thr Val Ile Leu Gly Arg Thr Tyr Arg Val Val Pro Gly Glu
            180                 185                 190

Glu Glu Gln Lys Phe Glu Val Glu Lys Tyr Ile Val His Lys Glu Phe
        195                 200                 205
```

-continued

```
Asp Asp Asp Thr Tyr Asp Asn Asp Ile Ala Leu Leu Gln Leu Lys Ser
    210                 215                 220

Asp Ser Ser Arg Cys Ala Gln Glu Ser Ser Val Val Arg Thr Val Cys
225                 230                 235                 240

Leu Pro Pro Ala Asp Leu Gln Leu Pro Asp Trp Thr Glu Cys Glu Leu
                245                 250                 255

Ser Gly Tyr Gly Lys His Glu Ala Leu Ser Pro Phe Tyr Ser Glu Arg
            260                 265                 270

Leu Lys Glu Ala His Val Arg Leu Tyr Pro Ser Ser Arg Cys Thr Ser
        275                 280                 285

Gln His Leu Leu Asn Arg Thr Val Thr Asp Asn Met Leu Cys Ala Gly
    290                 295                 300

Asp Thr Arg Ser Gly Gly Pro Gln Ala Asn Leu His Asp Ala Cys Gln
305                 310                 315                 320

Gly Asp Ser Gly Gly Pro
                325


<210> SEQ ID NO 4
<211> LENGTH: 252
<212> TYPE: DNA
<213> ORGANISM: Homo sapiens
<220> FEATURE:
<221> NAME/KEY: misc_feature
<222> LOCATION: (91)..(91)
<223> OTHER INFORMATION: n equals a, t, g or c
<220> FEATURE:
<221> NAME/KEY: misc_feature
<222> LOCATION: (185)..(185)
<223> OTHER INFORMATION: n equals a, t, g or c

<400> SEQUENCE: 4

attgcactga gcattccact taggaagagg atagagaagg atctgctccg cctttggcca     60

caggagcaga ggcagacctg ggatgcccca ntttctcttc agggatggat agtgacctgt    120

cttcattttg cacaggtaag agagtagtta gctaacctat gggaattata ctgtggggcc    180

ttgtnagctg cttctaagag gctaacctgg aaactaagct cagaggcaag gtaataaagc    240

acttcagggc tt                                                        252


<210> SEQ ID NO 5
<211> LENGTH: 247
<212> TYPE: DNA
<213> ORGANISM: Homo sapiens

<400> SEQUENCE: 5

atagagaaat gcctttatag aaaagtagaa accagtaata ttctcttctc cagcatcact     60

aacaccaaga gaccacctga ggtctaggtc cccaaagcag atggctccat agaaagcccc    120

actaacccgt ctccacattg ggcagtggaa gggttctgga aaggaagctc tatggctagg    180

agctgccaag gcctcttgag tgtgacatca caggttagag gccctgctga gctgctagca    240

cagtgca                                                              247


<210> SEQ ID NO 6
<211> LENGTH: 510
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n equals a, t, g or c
```

-continued

<220> FEATURE:
<221> NAME/KEY: misc_feature
<222> LOCATION: (46)..(46)
<223> OTHER INFORMATION: n equals a, t, g or c
<220> FEATURE:
<221> NAME/KEY: misc_feature
<222> LOCATION: (68)..(68)
<223> OTHER INFORMATION: n equals a, t, g or c
<220> FEATURE:
<221> NAME/KEY: misc_feature
<222> LOCATION: (115)..(115)
<223> OTHER INFORMATION: n equals a, t, g or c
<220> FEATURE:
<221> NAME/KEY: misc_feature
<222> LOCATION: (222)..(222)
<223> OTHER INFORMATION: n equals a, t, g or c
<220> FEATURE:
<221> NAME/KEY: misc_feature
<222> LOCATION: (247)..(247)
<223> OTHER INFORMATION: n equals a, t, g or c
<220> FEATURE:
<221> NAME/KEY: misc_feature
<222> LOCATION: (251)..(251)
<223> OTHER INFORMATION: n equals a, t, g or c
<220> FEATURE:
<221> NAME/KEY: misc_feature
<222> LOCATION: (253)..(253)
<223> OTHER INFORMATION: n equals a, t, g or c
<220> FEATURE:
<221> NAME/KEY: misc_feature
<222> LOCATION: (262)..(262)
<223> OTHER INFORMATION: n equals a, t, g or c
<220> FEATURE:
<221> NAME/KEY: misc_feature
<222> LOCATION: (265)..(265)
<223> OTHER INFORMATION: n equals a, t, g or c
<220> FEATURE:
<221> NAME/KEY: misc_feature
<222> LOCATION: (289)..(290)
<223> OTHER INFORMATION: n equals a, t, g or c
<220> FEATURE:
<221> NAME/KEY: misc_feature
<222> LOCATION: (294)..(294)
<223> OTHER INFORMATION: n equals a, t, g or c
<220> FEATURE:
<221> NAME/KEY: misc_feature
<222> LOCATION: (298)..(299)
<223> OTHER INFORMATION: n equals a, t, g or c
<220> FEATURE:
<221> NAME/KEY: misc_feature
<222> LOCATION: (303)..(303)
<223> OTHER INFORMATION: n equals a, t, g or c
<220> FEATURE:
<221> NAME/KEY: misc_feature
<222> LOCATION: (318)..(318)
<223> OTHER INFORMATION: n equals a, t, g or c
<220> FEATURE:
<221> NAME/KEY: misc_feature
<222> LOCATION: (320)..(320)
<223> OTHER INFORMATION: n equals a, t, g or c
<220> FEATURE:
<221> NAME/KEY: misc_feature
<222> LOCATION: (323)..(323)
<223> OTHER INFORMATION: n equals a, t, g or c
<220> FEATURE:
<221> NAME/KEY: misc_feature
<222> LOCATION: (342)..(343)
<223> OTHER INFORMATION: n equals a, t, g or c
<220> FEATURE:
<221> NAME/KEY: misc_feature
<222> LOCATION: (351)..(351)
<223> OTHER INFORMATION: n equals a, t, g or c
<220> FEATURE:
<221> NAME/KEY: misc_feature
<222> LOCATION: (359)..(359)
<223> OTHER INFORMATION: n equals a, t, g or c -continued
<220> FEATURE:
<221> NAME/KEY: misc_feature
<222> LOCATION: (362)..(363)
<223> OTHER INFORMATION: n equals a, t, g or c
<220> FEATURE:
<221> NAME/KEY: misc_feature
<222> LOCATION: (369)..(369)
<223> OTHER INFORMATION: n equals a, t, g or c
<220> FEATURE:
<221> NAME/KEY: misc_feature
<222> LOCATION: (389)..(390)
<223> OTHER INFORMATION: n equals a, t, g or c
<220> FEATURE:
<221> NAME/KEY: misc_feature
<222> LOCATION: (394)..(395)
<223> OTHER INFORMATION: n equals a, t, g or c
<220> FEATURE:
<221> NAME/KEY: misc_feature
<222> LOCATION: (397)..(398)
<223> OTHER INFORMATION: n equals a, t, g or c
<220> FEATURE:
<221> NAME/KEY: misc_feature
<222> LOCATION: (401)..(401)
<223> OTHER INFORMATION: n equals a, t, g or c
<220> FEATURE:
<221> NAME/KEY: misc_feature
<222> LOCATION: (414)..(414)
<223> OTHER INFORMATION: n equals a, t, g or c
<220> FEATURE:
<221> NAME/KEY: misc_feature
<222> LOCATION: (429)..(429)
<223> OTHER INFORMATION: n equals a, t, g or c
<220> FEATURE:
<221> NAME/KEY: misc_feature
<222> LOCATION: (432)..(433)
<223> OTHER INFORMATION: n equals a, t, g or c
<220> FEATURE:
<221> NAME/KEY: misc_feature
<222> LOCATION: (435)..(435)
<223> OTHER INFORMATION: n equals a, t, g or c
<220> FEATURE:
<221> NAME/KEY: misc_feature
<222> LOCATION: (441)..(441)
<223> OTHER INFORMATION: n equals a, t, g or c
<220> FEATURE:
<221> NAME/KEY: misc_feature
<222> LOCATION: (444)..(444)
<223> OTHER INFORMATION: n equals a, t, g or c
<220> FEATURE:
<221> NAME/KEY: misc_feature
<222> LOCATION: (446)..(446)
<223> OTHER INFORMATION: n equals a, t, g or c
<220> FEATURE:
<221> NAME/KEY: misc_feature
<222> LOCATION: (457)..(457)
<223> OTHER INFORMATION: n equals a, t, g or c
<220> FEATURE:
<221> NAME/KEY: misc_feature
<222> LOCATION: (459)..(459)
<223> OTHER INFORMATION: n equals a, t, g or c
<220> FEATURE:
<221> NAME/KEY: misc_feature
<222> LOCATION: (462)..(462)
<223> OTHER INFORMATION: n equals a, t, g or c
<220> FEATURE:
<221> NAME/KEY: misc_feature
<222> LOCATION: (466)..(466)
<223> OTHER INFORMATION: n equals a, t, g or c
<220> FEATURE:
<221> NAME/KEY: misc_feature
<222> LOCATION: (475)..(475)
<223> OTHER INFORMATION: n equals a, t, g or c
<220> FEATURE:
<221> NAME/KEY: misc_feature
<222> LOCATION: (480)..(480)
<223> OTHER INFORMATION: n equals a, t, g or c
<220> FEATURE:
<221> NAME/KEY: misc_feature
<222> LOCATION: (491)..(491)
<223> OTHER INFORMATION: n equals a, t, g or c
<220> FEATURE:
<221> NAME/KEY: misc_feature
<222> LOCATION: (505)..(505)
<223> OTHER INFORMATION: n equals a, t, g or c

<400> SEQUENCE: 6
aattcggcan agagtaacag cataacaagg gtaggtctga ctgcangctg ggactgggag 60
gcagagcnac gccaaggggg cctcggttaa acactggtcg ttcaatcacc tgcanaacga 120
ggaggcaagg atgctgttgg cctgggtaca gcattcctgg tcagcaacat gctcctagcg 180
taagcctatg gatctggagg ctgtttctgg gacaacggcc anctgtaccc ggaggaccag 240
accttcnccg ngnccggtcc tncgntgcct caactggctg gacgcgcann gggnctgnnc 300
ctngggcccc cttttcgngn tcnaaatttc acagtttact tnncgaaacc ngggacggng 360
gnnccgtgng gggccctggt ggttagttnn tggnngnngt ncgggttttc ttanaaaaag 420
gtttttggng gnncncggtt nttncnggaa ccatttncng gnttgnaatt ttttnagggn 480
aaatttcagg nagtttttta agggnccatt 510

<210> SEQ ID NO 7
<211> LENGTH: 409
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n equals a, t, g or c
<220> FEATURE:
<221> NAME/KEY: misc_feature
<222> LOCATION: (92)..(92)
<223> OTHER INFORMATION: n equals a, t, g or c
<220> FEATURE:
<221> NAME/KEY: misc_feature
<222> LOCATION: (225)..(225)
<223> OTHER INFORMATION: n equals a, t, g or c
<220> FEATURE:
<221> NAME/KEY: misc_feature
<222> LOCATION: (256)..(256)
<223> OTHER INFORMATION: n equals a, t, g or c
<220> FEATURE:
<221> NAME/KEY: misc_feature
<222> LOCATION: (267)..(267)
<223> OTHER INFORMATION: n equals a, t, g or c
<220> FEATURE:
<221> NAME/KEY: misc_feature
<222> LOCATION: (346)..(346)
<223> OTHER INFORMATION: n equals a, t, g or c
<220> FEATURE:
<221> NAME/KEY: misc_feature
<222> LOCATION: (356)..(356)
<223> OTHER INFORMATION: n equals a, t, g or c
<220> FEATURE:
<221> NAME/KEY: misc_feature
<222> LOCATION: (362)..(362)
<223> OTHER INFORMATION: n equals a, t, g or c
<220> FEATURE:
<221> NAME/KEY: misc_feature
<222> LOCATION: (364)..(364)
<223> OTHER INFORMATION: n equals a, t, g or c
<220> FEATURE:
<221> NAME/KEY: misc_feature
<222> LOCATION: (398)..(398)
<223> OTHER INFORMATION: n equals a, t, g or c

<400> SEQUENCE: 7
ggcanagttg cagaactgga aacgagtttg tacagaagtc agaactttgg gttaggaatg 60
agatctaggt tgtggctgct ggtatgcttc anttgctggc aataatgtgc cttgacaacc 120
gtgggccagg cctgggacca gggactcttc ctgtttcata aggaaaggaa gaattgcact 180
gagcattcca cttaggaaga ggatagagca aggaatctgc tccgnctttg gccacaggag 240
cagaggcaga cctggngatg ccccagnttc tctttcaggg atgggatagt gacctgtctt 300
acattttgca caggtaaaga gagttagtta gctaacctat tgggcnttta ttactntggg 360
gncnttgtga gctgcttttt aagaggttaa cctggaanct aaagttcag 409

<210> SEQ ID NO 8
<211> LENGTH: 358
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n equals a, t, g or c
<220> FEATURE:
<221> NAME/KEY: misc_feature
<222> LOCATION: (31)..(31)
<223> OTHER INFORMATION: n equals a, t, g or c
<220> FEATURE:
<221> NAME/KEY: misc_feature
<222> LOCATION: (53)..(54)
<223> OTHER INFORMATION: n equals a, t, g or c
<220> FEATURE:
<221> NAME/KEY: misc_feature
<222> LOCATION: (58)..(58)
<223> OTHER INFORMATION: n equals a, t, g or c
<220> FEATURE:
<221> NAME/KEY: misc_feature
<222> LOCATION: (101)..(101)
<223> OTHER INFORMATION: n equals a, t, g or c
<220> FEATURE:
<221> NAME/KEY: misc_feature
<222> LOCATION: (106)..(106)
<223> OTHER INFORMATION: n equals a, t, g or c
<220> FEATURE:
<221> NAME/KEY: misc_feature
<222> LOCATION: (145)..(145)
<223> OTHER INFORMATION: n equals a, t, g or c
<220> FEATURE:
<221> NAME/KEY: misc_feature
<222> LOCATION: (179)..(179)
<223> OTHER INFORMATION: n equals a, t, g or c
<220> FEATURE:
<221> NAME/KEY: misc_feature
<222> LOCATION: (219)..(219)
<223> OTHER INFORMATION: n equals a, t, g or c
<220> FEATURE:
<221> NAME/KEY: misc_feature
<222> LOCATION: (234)..(234)
<223> OTHER INFORMATION: n equals a, t, g or c
<220> FEATURE:
<221> NAME/KEY: misc_feature
<222> LOCATION: (240)..(240)
<223> OTHER INFORMATION: n equals a, t, g or c
<220> FEATURE:
<221> NAME/KEY: misc_feature
<222> LOCATION: (268)..(268)
<223> OTHER INFORMATION: n equals a, t, g or c
<220> FEATURE:
<221> NAME/KEY: misc_feature
<222> LOCATION: (290)..(290)
<223> OTHER INFORMATION: n equals a, t, g or c
<220> FEATURE:
<221> NAME/KEY: misc_feature
<222> LOCATION: (295)..(295)
<223> OTHER INFORMATION: n equals a, t, g or c -continued
<220> FEATURE:
<221> NAME/KEY: misc_feature
<222> LOCATION: (297)..(299)
<223> OTHER INFORMATION: n equals a, t, g or c
<220> FEATURE:
<221> NAME/KEY: misc_feature
<222> LOCATION: (304)..(304)
<223> OTHER INFORMATION: n equals a, t, g or c
<220> FEATURE:
<221> NAME/KEY: misc_feature
<222> LOCATION: (308)..(308)
<223> OTHER INFORMATION: n equals a, t, g or c
<220> FEATURE:
<221> NAME/KEY: misc_feature
<222> LOCATION: (315)..(315)
<223> OTHER INFORMATION: n equals a, t, g or c
<220> FEATURE:
<221> NAME/KEY: misc_feature
<222> LOCATION: (322)..(323)
<223> OTHER INFORMATION: n equals a, t, g or c
<220> FEATURE:
<221> NAME/KEY: misc_feature
<222> LOCATION: (354)..(354)
<223> OTHER INFORMATION: n equals a, t, g or c

<400> SEQUENCE: 8
taattcggca nagggacagg tctgactgca ngctgggact gggaggcaga gcnncgtnca 60 aggggcctc ggttaaacac tggtcgttca atcacctgca nacgangagg caaggatgct 120
gttggcctgg gtacaagcat tcctngtcag caacatgctc ctagcagaaa gcctatggna 180
tctgggaggc tgtttctggg acaacggcca cctgtaccng gaggaccaga cctnccccgn 240
gccgggcctt ccgtggcctt caattggntt tgacgtggca aaggggcttn gtctngngnn 300
cccntttntg ggggnaaaat tnnacaagtt ttaattgtcc cggaaaacct ggangagg 358

<210> SEQ ID NO 9
<211> LENGTH: 499
<212> TYPE: DNA
<213> ORGANISM: Homo sapiens
<220> FEATURE:
<221> NAME/KEY: misc_feature
<222> LOCATION: (186)..(186)
<223> OTHER INFORMATION: n equals a, t, g or c
<220> FEATURE:
<221> NAME/KEY: misc_feature
<222> LOCATION: (228)..(228)
<223> OTHER INFORMATION: n equals a, t, g or c
<220> FEATURE:
<221> NAME/KEY: misc_feature
<222> LOCATION: (249)..(249)
<223> OTHER INFORMATION: n equals a, t, g or c
<220> FEATURE:
<221> NAME/KEY: misc_feature
<222> LOCATION: (292)..(292)
<223> OTHER INFORMATION: n equals a, t, g or c
<220> FEATURE:
<221> NAME/KEY: misc_feature
<222> LOCATION: (296)..(296)
<223> OTHER INFORMATION: n equals a, t, g or c
<220> FEATURE:
<221> NAME/KEY: misc_feature
<222> LOCATION: (328)..(329)
<223> OTHER INFORMATION: n equals a, t, g or c
<220> FEATURE:
<221> NAME/KEY: misc_feature
<222> LOCATION: (345)..(345)
<223> OTHER INFORMATION: n equals a, t, g or c
<220> FEATURE:
<221> NAME/KEY: misc_feature
<222> LOCATION: (363)..(363)
<223> OTHER INFORMATION: n equals a, t, g or c -continued
<220> FEATURE:
<221> NAME/KEY: misc_feature
<222> LOCATION: (366)..(366)
<223> OTHER INFORMATION: n equals a, t, g or c
<220> FEATURE:
<221> NAME/KEY: misc_feature
<222> LOCATION: (376)..(376)
<223> OTHER INFORMATION: n equals a, t, g or c
<220> FEATURE:
<221> NAME/KEY: misc_feature
<222> LOCATION: (388)..(388)
<223> OTHER INFORMATION: n equals a, t, g or c
<220> FEATURE:
<221> NAME/KEY: misc_feature
<222> LOCATION: (397)..(397)
<223> OTHER INFORMATION: n equals a, t, g or c
<220> FEATURE:
<221> NAME/KEY: misc_feature
<222> LOCATION: (406)..(406)
<223> OTHER INFORMATION: n equals a, t, g or c
<220> FEATURE:
<221> NAME/KEY: misc_feature
<222> LOCATION: (408)..(408)
<223> OTHER INFORMATION: n equals a, t, g or c
<220> FEATURE:
<221> NAME/KEY: misc_feature
<222> LOCATION: (410)..(410)
<223> OTHER INFORMATION: n equals a, t, g or c
<220> FEATURE:
<221> NAME/KEY: misc_feature
<222> LOCATION: (413)..(413)
<223> OTHER INFORMATION: n equals a, t, g or c
<220> FEATURE:
<221> NAME/KEY: misc_feature
<222> LOCATION: (435)..(437)
<223> OTHER INFORMATION: n equals a, t, g or c
<220> FEATURE:
<221> NAME/KEY: misc_feature
<222> LOCATION: (440)..(440)
<223> OTHER INFORMATION: n equals a, t, g or c
<220> FEATURE:
<221> NAME/KEY: misc_feature
<222> LOCATION: (446)..(446)
<223> OTHER INFORMATION: n equals a, t, g or c
<220> FEATURE:
<221> NAME/KEY: misc_feature
<222> LOCATION: (454)..(454)
<223> OTHER INFORMATION: n equals a, t, g or c
<220> FEATURE:
<221> NAME/KEY: misc_feature
<222> LOCATION: (467)..(467)
<223> OTHER INFORMATION: n equals a, t, g or c
<220> FEATURE:
<221> NAME/KEY: misc_feature
<222> LOCATION: (475)..(475)
<223> OTHER INFORMATION: n equals a, t, g or c
<220> FEATURE:
<221> NAME/KEY: misc_feature
<222> LOCATION: (488)..(489)
<223> OTHER INFORMATION: n equals a, t, g or c

<400> SEQUENCE: 9
aattcggcag agggagaggg agatgcagcg aatcactctg cccttgtctg ccttcaccaa 60
ccccacctgt gagattgtgg atgagaagac tgtcgtggtc cacaccagcc agactccagt 120
tgaccctcag gagggcagca ccccccttat gggaccaggc cggggactcc tggggcctga 180
gccccnccag tggggcagga gccatggcag acactggtgc aggacagncc accctcctta 240
cagctaggng ggaactacca ctttgtgttt ctggtttaaa accctaccac tncccnggat 300
tttttggcgg attccttagt taagagtnna cagaagcagg tgggncctat ggcttggagg 360
gtnaanggtg gggtangggt tcctaaanag tgggttnctt ggttgncntn ccntgggagg 420

-continued aagattttgg ttttnnnggn tggggnacag tggncagttt ccacagngtt gttgntgtta 480
aggggttnnc aaaaaattg 499

<210> SEQ ID NO 10
<211> LENGTH: 294
<212> TYPE: DNA
<213> ORGANISM: Homo sapiens
<220> FEATURE:
<221> NAME/KEY: misc_feature
<222> LOCATION: (25)..(25)
<223> OTHER INFORMATION: n equals a, t, g or c
<220> FEATURE:
<221> NAME/KEY: misc_feature
<222> LOCATION: (222)..(222)
<223> OTHER INFORMATION: n equals a, t, g or c
<220> FEATURE:
<221> NAME/KEY: misc_feature
<222> LOCATION: (292)..(292)
<223> OTHER INFORMATION: n equals a, t, g or c

<400> SEQUENCE: 10
gggcacgaga tgaactccaa ggagnaaaaa ggacctggga actctgggta tgacggtccc 60
ccacccctgc ccttgttggg attcatcaag agatgtcatt tgctgattgt ctagggtgtg 120
gctaatggga ccttgtgtcc tatccttggc aggctacgtg ctgggcatta ccatgatggt 180
gatcatcatt gccatcggag ctggcatcat cttgggctac tnctacaaga ggtcagtagc 240
ttctcttctg ggccctctta ggaggagggg aggaaggtac acaaagtcaa anct 294

<210> SEQ ID NO 11
<211> LENGTH: 28
<212> TYPE: DNA
<213> ORGANISM: Artificial sequence
<220> FEATURE:
<223> OTHER INFORMATION: contains an Afl III restriction site

<400> SEQUENCE: 11
ggccgacatg tctggaggct gtttctgg 28

<210> SEQ ID NO 12
<211> LENGTH: 33
<212> TYPE: DNA
<213> ORGANISM: Artificial sequence
<220> FEATURE:
<223> OTHER INFORMATION: contains a Hind III restriction site

<400> SEQUENCE: 12
ggcggaagct tattaggccc caggagtccc ggc 33

<210> SEQ ID NO 13
<211> LENGTH: 36
<212> TYPE: DNA
<213> ORGANISM: Artificial sequence
<220> FEATURE:
<223> OTHER INFORMATION: contains a Bam HI restriction enzyme site and an efficient signal for initiation of translation in eukaryotic cells (Kozak, M., J. Mol. Biol. 196:947-950 (1987))

<400> SEQUENCE: 13
ggccgggatc cgccatcatg ctgttggcct gggtac 36

<210> SEQ ID NO 14
<211> LENGTH: 35
<212> TYPE: DNA
<213> ORGANISM: Artificial sequence
<220> FEATURE:
<223> OTHER INFORMATION: contains an Asp 718 restriction site -continued

<400> SEQUENCE: 14
ggccgggtac cttattaggc cccaggagtc ccggc 35

<210> SEQ ID NO 15
<211> LENGTH: 36
<212> TYPE: DNA
<213> ORGANISM: Artificial sequence
<220> FEATURE:
<223> OTHER INFORMATION: contains a Bam HI site, a Kozak sequence, and an AUG start codon

<400> SEQUENCE: 15
ggccgggatc cgccatcatg ctgttggcct gggtac 36

<210> SEQ ID NO 16
<211> LENGTH: 35
<212> TYPE: DNA
<213> ORGANISM: Artificial sequence
<220> FEATURE:
<223> OTHER INFORMATION: contains an Asp 718 restriction site

<400> SEQUENCE: 16
ggccgggtac cttattaggc cccaggagtc ccggc 35

<210> SEQ ID NO 17
<211> LENGTH: 733
<212> TYPE: DNA
<213> ORGANISM: Homo sapiens

<400> SEQUENCE: 17
gggatccgga gcccaaatct tctgacaaaa ctcacacatg cccaccgtgc ccagcacctg 60
aattcgaggg tgcaccgtca gtcttcctct tcccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 18
<211> LENGTH: 86
<212> TYPE: DNA
<213> ORGANISM: Artificial sequence
<220> FEATURE:
<223> OTHER INFORMATION: contains 18bp of sequence complementary to the SV40 early promoter sequence flanked with an XhoI site

<400> SEQUENCE: 18
gcgcctcgag atttccccga aatctagatt tccccgaaat gatttccccg aaatgatttc 60
cccgaaatat ctgccatctc aattag 86

-continued

<210> SEQ ID NO 19
<211> LENGTH: 27
<212> TYPE: DNA
<213> ORGANISM: Artificial sequence
<220> FEATURE:
<223> OTHER INFORMATION: complementary to the SV40 promoter and flanked with a Hind III site

<400> SEQUENCE: 19
gcggcaagct ttttgcaaag cctaggc 27

<210> SEQ ID NO 20
<211> LENGTH: 271
<212> TYPE: DNA
<213> ORGANISM: Artificial sequence
<220> FEATURE:
<223> OTHER INFORMATION: artificial sequence from B-gal:promoter plasmid

<400> SEQUENCE: 20
ctcgagattt ccccgaaatc tagatttccc cgaaatgatt tccccgaaat gatttccccg 60
aaatatctgc catctcaatt agtcagcaac catagtcccg cccctaactc cgcccatccc 120
gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 21
<211> LENGTH: 32
<212> TYPE: DNA
<213> ORGANISM: Artificial sequence
<220> FEATURE:
<223> OTHER INFORMATION: primer for EGR-1 promoter sequence

<400> SEQUENCE: 21
gcgctcgagg gatgacagcg atagaacccc gg 32

<210> SEQ ID NO 22
<211> LENGTH: 31
<212> TYPE: DNA
<213> ORGANISM: Artificial sequence
<220> FEATURE:
<223> OTHER INFORMATION: primer for EGR-1 promoter sequence

<400> SEQUENCE: 22
gcgaagcttc gcgactcccc ggatccgcct c 31

<210> SEQ ID NO 23
<211> LENGTH: 73
<212> TYPE: DNA
<213> ORGANISM: Artificial sequence
<220> FEATURE:
<223> OTHER INFORMATION: contains four tandem copies of the NF-KappaB binding site, 18 bp of sequence complementary to the 5' end of the SV40 early promoter sequence, and flanked with an XhoI site

<400> SEQUENCE: 23
gcggcctcga ggggactttc ccggggactt tccggggact ttccgggact ttccatcctg 60
ccatctcaat tag 73

<210> SEQ ID NO 24
<211> LENGTH: 256
<212> TYPE: DNA
<213> ORGANISM: Artificial sequence -continued
<220> FEATURE:
<223> OTHER INFORMATION: artificial sequence from pB-gal:promoter
      plasmid

<400> SEQUENCE: 24
ctcgagggga ctttcccggg gactttccgg ggactttccg ggactttcca tctgccatct     60
caattagtca gcaaccatag tcccgcccct aactccgccc atcccgcccc taactccgcc    120
cagttccgcc cattctccgc cccatggctg actaattttt tttatttatg cagaggccga    180
ggccgcctcg gcctctgagc tattccagaa gtagtgagga ggcttttttg gaggcctagg    240
cttttgcaaa aagctt                                                    256

<210> SEQ ID NO 25
<211> LENGTH: 36
<212> TYPE: DNA
<213> ORGANISM: Artificial sequence
<220> FEATURE:
<223> OTHER INFORMATION: contains a BamHI restriction site

<400> SEQUENCE: 25
cgaagaggga tccatgctgt tggcctgggt acaagc                               36

<210> SEQ ID NO 26
<211> LENGTH: 40
<212> TYPE: DNA
<213> ORGANISM: Artificial sequence
<220> FEATURE:
<223> OTHER INFORMATION: contains an XbaI restriction site

<400> SEQUENCE: 26
gccggctcta gatcagacgt agcaccaggg cccgcgcggg                           40

<210> SEQ ID NO 27
<211> LENGTH: 33
<212> TYPE: DNA
<213> ORGANISM: Artificial sequence
<220> FEATURE:
<223> OTHER INFORMATION: contains an XbaI restriction site

<400> SEQUENCE: 27
cactggtcta gatcaggccc caggagtccc ggc                                  33

<210> SEQ ID NO 28
<211> LENGTH: 6
<212> TYPE: PRT
<213> ORGANISM: Artificial sequence
<220> FEATURE:
<223> OTHER INFORMATION: signature pattern of a kringle domain
<220> FEATURE:
<221> NAME/KEY: MISC_FEATURE
<222> LOCATION: (1)
<223> OTHER INFORMATION: Xaa equals Phe or Tyr
<220> FEATURE:
<221> NAME/KEY: MISC_FEATURE
<222> LOCATION: (6)
<223> OTHER INFORMATION: Xaa equals Asp or Asn or Arg

<400> SEQUENCE: 28

Xaa Cys Arg Asn Pro Xaa
  1               5

<210> SEQ ID NO 29
<211> LENGTH: 33
<212> TYPE: DNA
<213> ORGANISM: Artificial sequence -continued

```
<220> FEATURE:
<223> OTHER INFORMATION: primer for subcloning

<400> SEQUENCE: 29

ggctcgcata tgtctggagg ctgtttctgg gac                                33


<210> SEQ ID NO 30
<211> LENGTH: 40
<212> TYPE: DNA
<213> ORGANISM: Artificial sequence
<220> FEATURE:
<223> OTHER INFORMATION: primer for subcloning

<400> SEQUENCE: 30

gcgcatggta ccttattagt ccttttctc cttggagttc                          40


<210> SEQ ID NO 31
<211> LENGTH: 12
<212> TYPE: DNA
<213> ORGANISM: Artificial sequence
<220> FEATURE:
<223> OTHER INFORMATION: NF-KappaB binding site

<400> SEQUENCE: 31

ggggactttc cc                                                       12
```

TISSUE PLASMINOGEN ACTIVATOR-LIKE PROTEASE

This application is a divisional of U.S. application Ser. No. 10/057,951, filed Jan. 29, 2002, now U.S. Pat. No. 6,815,534 which is a divisional of U.S. application Ser. No. 09/411,977, filed Oct. 4, 1999, now U.S. Pat. No. 6,372,473, which is a continuation-in-part of U.S. application Ser. No. 09/084,491, filed May 27, 1998, now abandoned which claims benefit under 35 U.S.C. § 119(e) of U.S. Provisional Application No. 60/048,000, filed on May 28, 1997, each of which, including its corresponding sequence listing(s), is hereby incorporated by reference in its entirety.

FIELD OF THE INVENTION

The present invention relates to a novel human gene encoding a polypeptide which is a homolog of tissue-type plasminogen activator (t-PA). More specifically, isolated nucleic acid molecules are provided encoding a human polypeptide named tissue-plasminogen activator-like protease, hereinafter referred to as "t-PALP". t-PALP polypeptides are also provided, as are vectors, host cells and recombinant methods for producing the same. Also provided are diagnostic methods for detecting disorders related to the circulatory system and therapeutic methods for treating such disorders. The invention further relates to screening methods for identifying agonists and antagonists of t-PALP activity.

BACKGROUND OF THE INVENTION

The plasmin coagulation system is activated in response to vascular injury. Within a few minutes of the injury, prothrombin is activated through the coagulation cascade to give rise to thrombin. Thrombin then converts fibrinogen to insoluble fibrin, which then interdigitates with and strengthens the primary platelet. Abnormal blood clotting can lead to many vascular diseases, such as stroke, deep-vein thrombosis, peripheral arterial occlusion, pulmonary embolism, and myocardiothrombosis, each of which constitutes a major health risk. Such diseases are primarily caused by partial or total occlusion of a blood vessel by a blood clot. Such clots consist essentially of a mass of fibrin and platelets. The prevention of clot formation and the dissolution of existing clots are two major therapeutic avenues frequently used for the treatment of disease states related to blood clots. Prevention of clot formation is primarily achieved through the inhibition of thrombin activity, whereas the dissolution of existing clots is frequently achieved by the activation of plasminogen which dissolves the existing blood clot (thereby affecting the fibrinolysis pathway).

The fibrinolytic system is activated by the deposition of fibrin. The conversion of fibrinogen to fibrin results in the exposure of many lysine residues on the surface of the molecule. A factor released from endothelial cells, termed tissue-type plasminogen activator (t-PA), activates plasminogen. Only upon activation can plasminogen bind to exposed lysine residues on the surface of fibrin, resulting in the degradation of fibrin, and, ultimately, the degradation of the blood clot itself.

In man and other animals, t-PA plays an essential role in the dissolution of fibrin clots (see, e.g., Verstraete and Collen, (1986) *Blood* 67:1425). t-PA is composed of several domains which share sequence homology with other proteins. These are the fibronectin finger-like domain, the epidermal growth factor-like domain, the kringle domain (of which t-PA has two), and the protease domain (Pennica, D., et al., (1983) Nature 301:214–221; Banyai, L., et al., (1983) *FEBS Lett.* 163:37–41). Only the function of the protease domain (residues 276–527) has been unambiguously defined. This finding was first based on the observed sequence homology with other known serine proteases. More recently, limited reduction of the two-chain form of t-PA has allowed the direct isolation and functional characterization of the protease region (Rijken and Groeneveld, (1986) *J. Biol. Chem.,* 261:3098).

In addition to the role played by human t-PA and related protease-like molecules in the fibrinolytic system, this same family of molecules also play important roles in carcinogenesis. On the one hand, numerous studies have implicated the plasminogen activator and/or protease activity of t-PA and related molecules in promoting progression of carcinogenesis and metastasis (for example see: Alizadeh, H., (1995) Curr. Eye Res. 14:449; Yamashita, J., (1993) Br. J. Cancer 68:524; Yamashita, J., (1992) Int. J. Clin. Lab Res. 21:227; Koller, A., (1984) Eur. Urol. 10:389). As such, inhibitors of the plasminogen activator and/or protease activity of t-PA and related molecules may provide useful therapeutics in combating cancer.

On the other hand, there is also now a large body of evidence which shows that specific domains from proteins such as t-PA can actually inhibit tumorigenesis and metastasis by inhibiting endothelial cell-mediated vascularization (i.e. angiogenesis) which is required for tumor growth. The specific domains mediating such anti-angiogenic activity have been identified as "kringle" domains. Kringle domains are triple-looped, disulfide cross-linked domains occurring with varying copy numbers in some serine proteases and plasma proteins. The kringle domain has been found in proteins such as: Apolipoprotein A (38 copies); Blood coagulation factor XII (Hageman factor) (1 copy); Hepatocyte growth factor (HGF) (4 copies); Hepatocyte growth factor-like protein (4 copies); Hepatocyte growth factor activator (1 copy); Plasminogen (5 copies); Thrombin (2 copies); Urokinase-type plasminogen activator (1 copy); and Tissue plasminogen activator (TPA) (2 copies). The signature pattern of a kringle domain is [F/Y]-C-R-N-P-[D/N/R] (SEQ ID NO:28), where C (cysteine) is involved in disulfide bond formation.

Kringle domains appear to be effective inhibitors of endothelial cell angiogenesis, and thus, effective inhibitors of tumorigenesis and metastasis. It has been demonstrated, for example, that a four-kringle domain containing protein called HGF/NK4 inhibits invasion of multiple tumorigenic cell types in both in vitro and in vivo assays (Date, K., et al. (1998) Oncogene 17:3045). Similarly, angiostatin (a fragment of plasminogen containing four kringle domains) has also been shown to inhibit tumor vascularization, growth, and metastasis (O'Reilly M. S., et al., (1994) Cell 79:315; O'Reilly, M. S., et al., (1996) Nat. Med. 2:689). Furthermore, a fragment of plasminogen containing just three kringle domains has been demonstrated to markedly reduce growth of malignant brain tumors in mice (Joe, J. Y., et al., (1999) Int. J. Cancer 82:694). Finally, it has also been demonstrated that a single kringle domain of angiostatin is sufficient to significantly inhibit endothelial cell angiogenesis (Cao, Y., et al., (1996) J. Biol. Chem. 271:29461). Therefore, t-PALP polynucleotides and/or polypeptides of the invention may provide particularly good therapeutic molecules for use in treating cancer and/or tumorigenesis, as well as in therapeutically modulating angiogenesis.

There is a clear need, therefore, for identification and characterization for such enzymes that influence the fibrinolytic system, both normally and in disease states. In particular, there is a need to isolate and characterize additional human tissue plasminogen activator and related protease-like molecules which possess such functions as the activation of plasminogen and may be employed, therefore, for preventing, ameliorating or correcting dysfunctions or disease states or, alternatively, augmenting the positive, natural actions of such enzymes.

SUMMARY OF THE INVENTION

The present invention provides isolated nucleic acid molecules comprising a polynucleotide encoding at least a portion of the t-PALP polypeptide having the complete amino acid sequence shown in SEQ ID NO:2 or the complete amino acid sequence encoded by the cDNA clone deposited as plasmid DNA HMSIB42 (ATCC Deposit Number 209023) on May 8, 1997. The nucleotide sequence determined by sequencing the deposited t-PALP clone, which is shown in FIGS. 1A, 1B, and 1C (SEQ ID NO:1), contains an open reading frame encoding a complete polypeptide of 263 amino acid residues, including an initiation codon encoding an N-terminal methionine at nucleotide positions 124–126, and a predicted molecular weight of about 28.2 kDa. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC Deposit Number 209023, which molecules also can encode additional amino acids fused to the N-terminus of the t-PALP amino acid sequence.

The t-PALP protein of the present invention shares sequence homology with the translation product of the human mRNA for t-PA (FIG. 2) (SEQ ID NO:3), including the following conserved domains: (a) the predicted kringle domain of about 60 amino acids and (b) the predicted protease domain of about 179 amino acids. t-PA is thought to be important in the regulation of blood clotting and disorders related thereto. The homology between t-PA and t-PALP indicates that t-PALP may also be involved in the regulation of normal and abnormal clotting in such conditions including many vascular diseases, such as stroke, deep-vein thrombosis, peripheral arterial occlusion, pulmonary embolism, and myocardiothrombosis.

The encoded polypeptide has a predicted leader sequence of about 21 amino acids underlined in FIGS. 1A, 1B, and 1C. The amino acid sequence of the predicted mature t-PALP protein is also shown in FIGS. 1A, 1B, and 1C, as amino acid residues 22–263 and as residues 1–242 in SEQ ID NO:2.

Thus, one aspect of the invention provides an isolated nucleic acid molecule comprising a polynucleotide having a nucleotide sequence selected from the group consisting of: (a) a nucleotide sequence encoding a full-length t-PALP polypeptide having the complete amino acid sequence in SEQ ID NO:2 excepting the N-terminal methionine (i.e., positions −20 to 242 of SEQ ID NO:2) or the complete amino acid sequence excepting the N-terminal methionine encoded by the cDNA clone contained in the ATCC Deposit No. 209023; (b) a nucleotide sequence encoding a mature t-PALP polypeptide having the amino acid sequence in SEQ ID NO:2 from residue 1 to 242 or as encoded by the cDNA clone contained in the ATCC Deposit No. 209023; (c) a nucleotide sequence encoding the predicted kringle domain of the t-PALP polypeptide having the amino acid sequence at positions 4 to 63 in SEQ ID NO:2 or as encoded by the cDNA clone contained in the ATCC Deposit No. 209023; (d) a nucleotide sequence encoding a polypeptide comprising the predicted protease domain of the t-PALP polypeptide having the amino acid sequence at positions 64 to 242 in SEQ ID NO:2 or as encoded by the cDNA clone contained in the ATCC Deposit No. 209023; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical (or 10% different), and more preferably at least 95%, 96%, 97%, 98% or 99% identical (or 5%, 4%, 3%, 2% or 1% different from), to any of the nucleotide sequences in (a), (b), (c), (d) or (e) above, or a polynucleotide which hybridizes under stringent hybridization conditions to a polynucleotide in (a), (b), (c), (d) or (e) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a t-PALP polypeptide having an amino acid sequence in (a), (b), (c) or (d) above.

The present invention also relates to recombinant vectors, which include the isolated nucleic acid molecules of the present invention, and to host cells containing the recombinant vectors, as well as to methods of making such vectors and host cells and for using them for production of t-PALP polypeptides or peptides by recombinant techniques.

The invention further provides an isolated t-PALP polypeptide comprising an amino acid sequence selected from the group consisting of: (a) the amino acid sequence of the full-length t-PALP polypeptide having the complete amino acid sequence shown in SEQ ID NO:2 excepting the N-terminal methionine (i.e., positions −20 to 242 of SEQ ID NO:2) or the complete amino acid sequence excepting the N-terminal methionine encoded by the cDNA clone contained in the ATCC Deposit No. 209023; (b) the amino acid sequence comprising the mature form of the t-PALP polypeptide having the amino acid sequence at positions 1 to 242 in SEQ ID NO:2 or as encoded by the cDNA clone contained in the ATCC Deposit No. 209023; (c) the amino acid sequence comprising the predicted kringle domain of the t-PALP polypeptide having the amino acid sequence at positions 4 to 63 in SEQ ID NO:2 or as encoded by the cDNA clone contained in the ATCC Deposit No. 209023; and (d) the amino acid sequence comprising the predicted protease domain of the t-PALP polypeptide having the amino acid sequence at positions 64 to 242 in SEQ ID NO:2 or as encoded by the cDNA clone contained in the ATCC Deposit No. 209023. The polypeptides of the present invention also include polypeptides having an amino acid sequence at least 80% identical (that is, 20% different), more preferably at least 90% identical (10% different), and still more preferably 95%, 96%, 97%, 98% or 99% identical to (which also may be expressed as 5%, 4%, 3%, 2% or 1% different from) those described in (a), (b), (c) or (d) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a t-PALP polypeptide having an amino acid sequence described in (a), (b) or (c) above. Peptides or polypeptides having the amino acid sequence of an epitope-bearing portion of a t-PALP polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a t-PALP polypeptide having an amino acid sequence described in (a), (b), (c) or (d) above. The invention further provides methods for isolating antibodies that bind specifically to a t-PALP polypeptide having an amino acid sequence as described herein. Such antibodies are useful diagnostically or therapeutically as described below.

The invention also provides for pharmaceutical compositions comprising t-PALP polypeptides, particularly human t-PALP polypeptides, which may be employed, for instance, to treat many vascular diseases, such as stroke, deep-vein thrombosis, peripheral arterial occlusion, pulmonary embolism, and myocardiothrombosis. Further uses of t-PALP may include induction of growth of hepatocytes and regeneration of liver tissue. Methods of treating individuals in need of t-PALP polypeptides are also provided.

The invention further provides compositions comprising a t-PALP polynucleotide or an t-PALP polypeptide for administration to cells in vitro, to cells ex vivo and to cells in vivo, or to a multicellular organism. In certain particularly preferred embodiments of this aspect of the invention, the compositions comprise a t-PALP polynucleotide for expression of a t-PALP polypeptide in a host organism for treatment of disease. Particularly preferred in this regard is expression in a human patient for treatment of a dysfunction associated with aberrant endogenous activity of a t-PALP The present invention also provides a screening method for identifying compounds capable of enhancing or inhibiting a biological activity of the t-PALP polypeptide, which involves contacting an enzyme which is activated by the t-PALP polypeptide with the candidate compound in the presence of a t-PALP polypeptide, assaying proteolytic activity of the plasminogen-like molecule in the presence of the candidate compound and of t-PALP polypeptide, and comparing the plasminogen-like molecule activity to a standard level of activity, the standard being assayed when contact is made between the plasminogen-like molecule and in the presence of the t-PALP polypeptide and the absence of the candidate compound In this assay, an increase in plasminogen-like molecule activity over the standard indicates that the candidate compound is an agonist of t-PALP activity and a decrease in plasminogen-like molecule activity compared to the standard indicates that the compound is an antagonist of t-PALP activity.

In another aspect, a screening assay for agonists and antagonists is provided which involves determining the effect a candidate compound has on t-PALP binding to a plasminogen-like molecule. In particular, the method involves contacting the plasminogen-like molecule with a t-PALP polypeptide and a candidate compound and determining whether t-PALP polypeptide binding to the plasminogen-like molecule is increased or decreased due to the presence of the candidate compound. In this assay, an increase in binding of t-PALP over the standard binding indicates that the candidate compound is an agonist of t-PALP binding activity and a decrease in t-PALP binding compared to the standard indicates that the compound is an antagonist of t-PALP binding activity.

It has been discovered that t-PALP is expressed not only in activated monocytes, but in a number of other cells and tissues including cerebellum, smooth muscle, resting and PHA-treated T-cells, GM-CSF-treated macrophages, frontal cortex of the brain, breast lymph node, chronic lymphocytic leukemic spleen, and several others. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the circulatory system, significantly higher or lower levels of t-PALP gene expression may be detected in certain tissues (e.g., cancerous and wounded tissues) or bodily fluids (e.g., serum, plasma, urine, synovial fluid or spinal fluid) taken from an individual having such a disorder, relative to a "standard" t-PALP gene expression level, i.e., the t-PALP expression level in healthy tissue from an individual not having the circulatory system disorder. Thus, the invention provides a diagnostic method useful during diagnosis of such a disorder, which involves: (a) assaying t-PALP gene expression level in cells or body fluid of an individual; (b) comparing the t-PALP gene expression level with a standard t-PALP gene expression level, whereby an increase or decrease in the assayed t-PALP gene expression level compared to the standard expression level is indicative of disorder in the circulatory system.

A further aspect of the invention is related to the relative clot-specificities which t-PALP and t-PA may possess. For example, t-PALP may have a higher or lower affinity for exerting its proteolytic activity with respect to a blood clot which localized itself to the lungs than does t-PA. In addition, t-PALP may have a higher or lower affinity for a specific constituent of a given blood clot than does t-PA. Thus, the t-PALP molecule may prove useful as an agent which, directly or indirectly, results in the dissolution of a blood clot with a higher or lower activity than other agents.

An additional aspect of the invention is related to a method for treating an individual in need of an increased level of t-PALP activity in the body comprising administering to such an individual a composition comprising a therapeutically effective amount of an isolated t-PALP polypeptide of the invention or an agonist thereof.

A still further aspect of the invention is related to a method for treating an individual in need of a decreased level of t-PALP activity in the body comprising, administering to such an individual a composition comprising a therapeutically effective amount of an t-PALP antagonist. Preferred antagonists for use in the present invention are t-PALP-specific antibodies.

BRIEF DESCRIPTION OF THE FIGURES

FIGS. 1A, 1B, and 1C show the nucleotide sequence (SEQ ID NO:1) and deduced amino acid sequence (SEQ ID NO:2) of t-PALP.

The predicted leader sequence of about 21 amino acids is underlined. Note that the methionine residue at the beginning of the leader sequence in FIGS. 1A, 1B, and 1C is shown in position number (positive) 1, whereas the leader positions in the corresponding sequence of SEQ ID NO:2 are designated with negative position numbers. Thus, the leader sequence positions 1 to 21 in FIGS. 1A, 1B, and 1C correspond to positions −21 to −1 in SEQ ID NO:2.

FIG. 2 shows the regions of identity between the amino acid sequences of the t-PALP protein and amino acid residues 191 to 516 of the translation product of the human mRNA for t-PA (residues 1–325 in SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters. Conserved regions of identity include from Ser-12 to Gly-21, from Ser-22 to Thr-38, from Ser-39 to Trp-49, from Leu-50 to Ser-62, from Gly-63 to Val-84, from Ser-85 to Glu-97, from Arg-100 to Glu-118, from Ala-119 to Glu-127, from Val-128 to Ala-143, from Val-146 to Lys-163, from Lys-164 to Ile-180, from Ala-186 to Leu-200, from Lys-201 to Leu-220, from Ser-221 to Val-236, from Val-237 to Gln-248, and from Glu-249 to Ala-263 of SEQ ID NO:2. Polynucleotides encoding each of these conserved domains are also encompassed by the invention, as well as combinations of the conserved domains. These conserved domains are preferred embodiments of the present invention.

Figure 3:
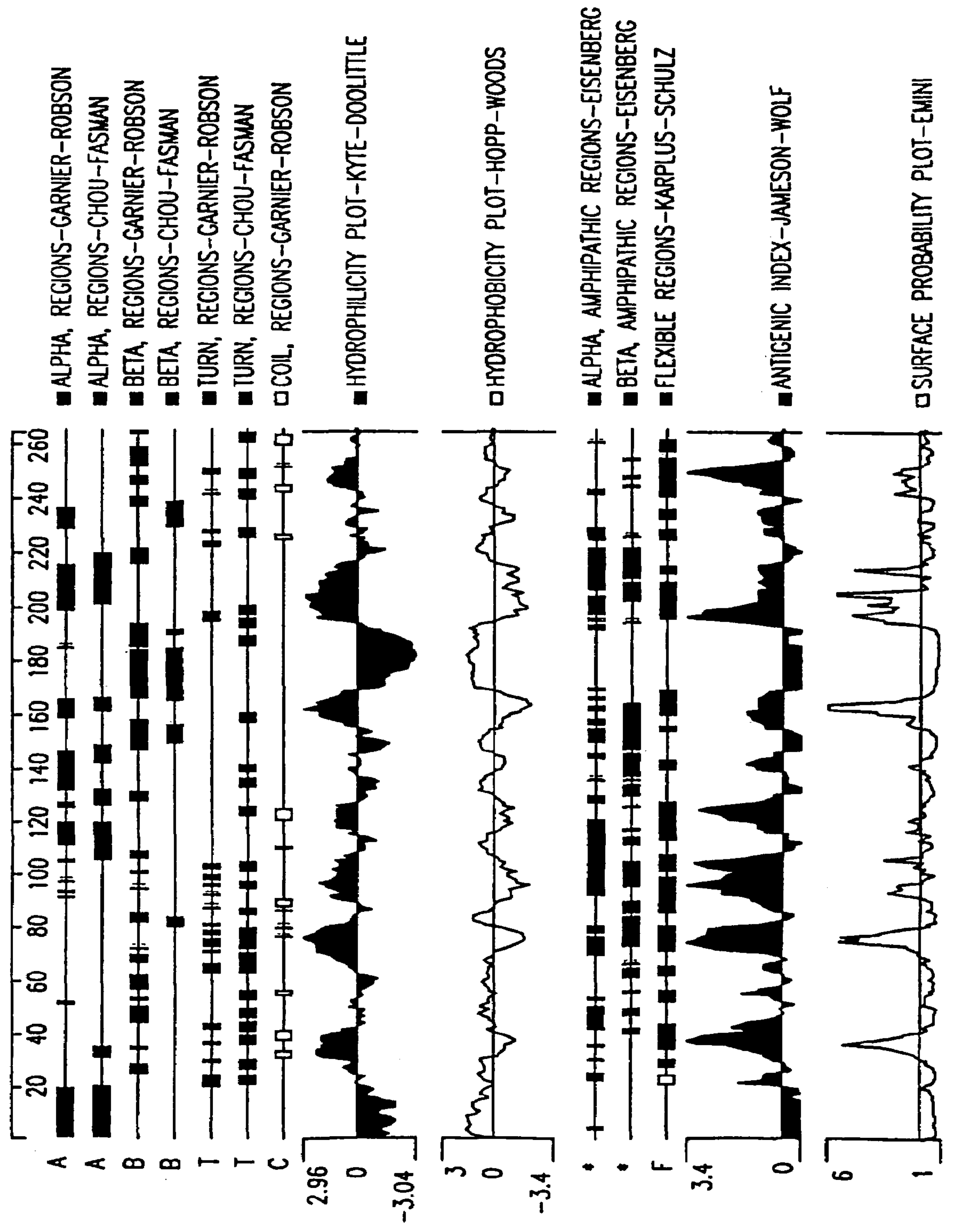

FIG. 3 shows an analysis of the t-PALP amino acid sequence. Alpha, beta, turn and coil regions; hydrophilicity and hydrophobicity; amphipathic regions; flexible regions; antigenic index and surface probability are shown, as predicted for the amino acid sequence of SEQ ID NO:2 using the default parameters of the recited computer programs. In the "Antigenic Index—Jameson-Wolf" graph, the positive peaks indicate locations of the highly antigenic regions of the t-PALP protein, i.e., regions from which epitope-bearing peptides of the invention can be obtained. Antigenic polypeptides include from about Ala-19 to about Gly-24, from about Asn-29 to about Cys-46, from about Ala-52 to about Ala-57, from about Val-61 to about Asn-66, from about Ser-68 to about Trp-81, from about Ser-85 to about Gln-107, from about Glu-115 to about Gln-129, from about Pro-138 to about Ala-145, from about Gln-154 to about Gly-167, from about Tyr-192 to about Arg-215, from about Thr-224 to about Val-236, from about Thr-240 to about Thr-252, and from about Ala-258 to about Ala-263 of the amino acid sequence of SEQ ID NO:2 using the numbering scheme of FIGS. 1A, 1B, and 1C. Polynucleotides encoding these antigenic polypeptides are also encompassed by the invention. These antigenic polypeptides are preferred embodiments of the present invention.

The data presented in FIG. 3 are also represented in tabular form in Table 1 (below). The columns are labeled with the headings "Residue", "Pos. #", and Roman Numerals I–XIV. The column headings refer to the following features of the amino acid sequence in SEQ ID NO:2 using the numbering scheme of FIGS. 1A, 1B, and 1C: "Residue": amino acid residue of t-PALP as shown in and FIGS. 1A, 1B, and 1C; "Pos. #": position of the corresponding residue within SEQ ID NO:2 using the numbering scheme of FIGS. 1A, 1B, and 1C; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Gamier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

Figure 4:
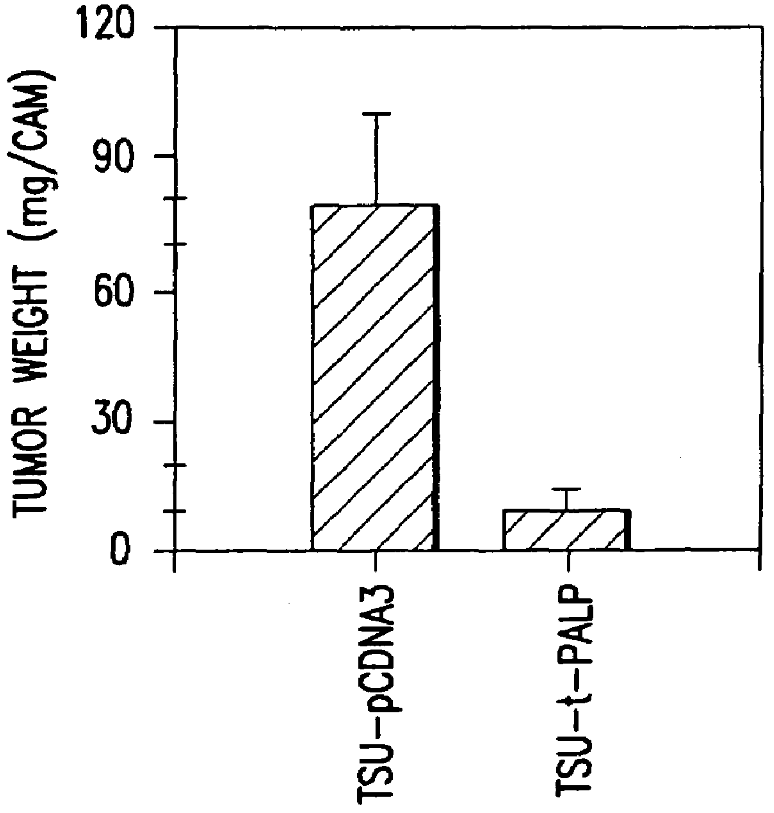

FIG. 4 shows an analysis of tumor growth of TSU cells transfected with t-PALP as determined by a chick chorioallantoic membrane (CAM) assay. Using a protocol based on that of Brooks, et al. (See, *Cell* 79:1157–64 (1994); See also, Brooks, et al., *Cell* 92:391–400 (1998)), the effects of t-PALP on the growth of TSU cells were analyzed in a CAM assay. Fifteen to twenty eggs were used for each treatment and the mean +/− standard error of tumor mass (mg/CAM) was calculated. The resulting data were subjected to the student's t-test for statistical analysis. The figure shows tumor weight (in mg per CAM) plotted against either tumor cells transfected with expression vector (labeled as "TSU-pCDNA3") only or against tumor cells transfected with a t-PALP expression vector (labeled as "TSU-t-PALP").

Figure 5:
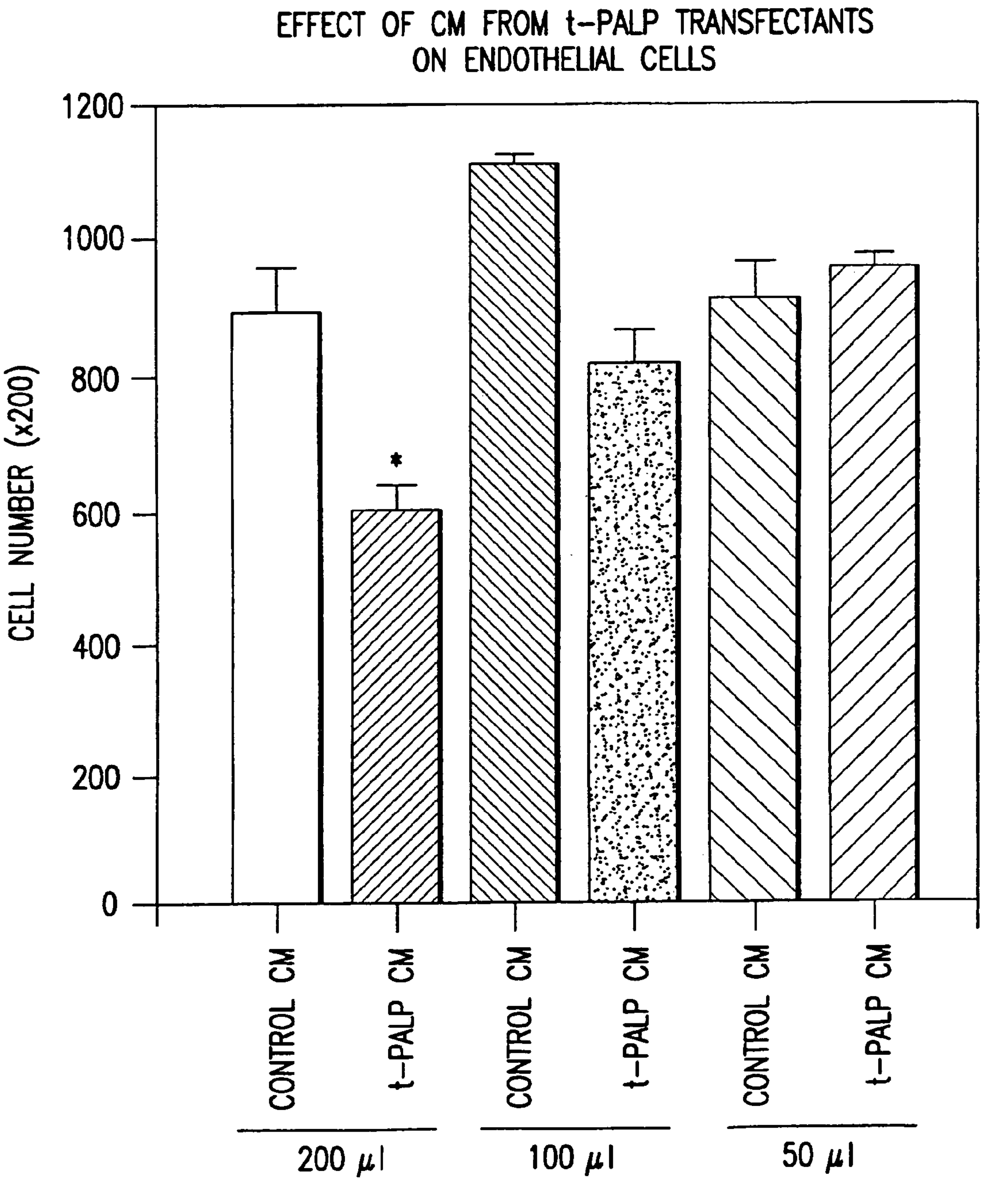

FIG. 5 shows the effect of conditioned medium from TSU cells transiently transfected with a t-PALP expression construct. Cell number was used to assess the effect of t-PALP on endothelial cells. Aliquots of either 50, 100 or 200 microliters of conditioned medium from the transiently transfected TSU cell cultures was added to the culture medium of endothelial cells. Treated cultures were then incubated at 37° C. The number of cells in each culture was then determined.

Results of the experiments are plotted in FIG. 5 as cell number (×200) against 50, 100 or 200 microliters of either the control conditioned medium (labeled as "Control CM") or conditioned medium from t-PALP-transfected TSU cells (labeled as "t-PALP CM"). The data are plotted as the mean +/− standard deviation. Significance according to the student's t-test is indicated by an asterisk.

Figure 6:
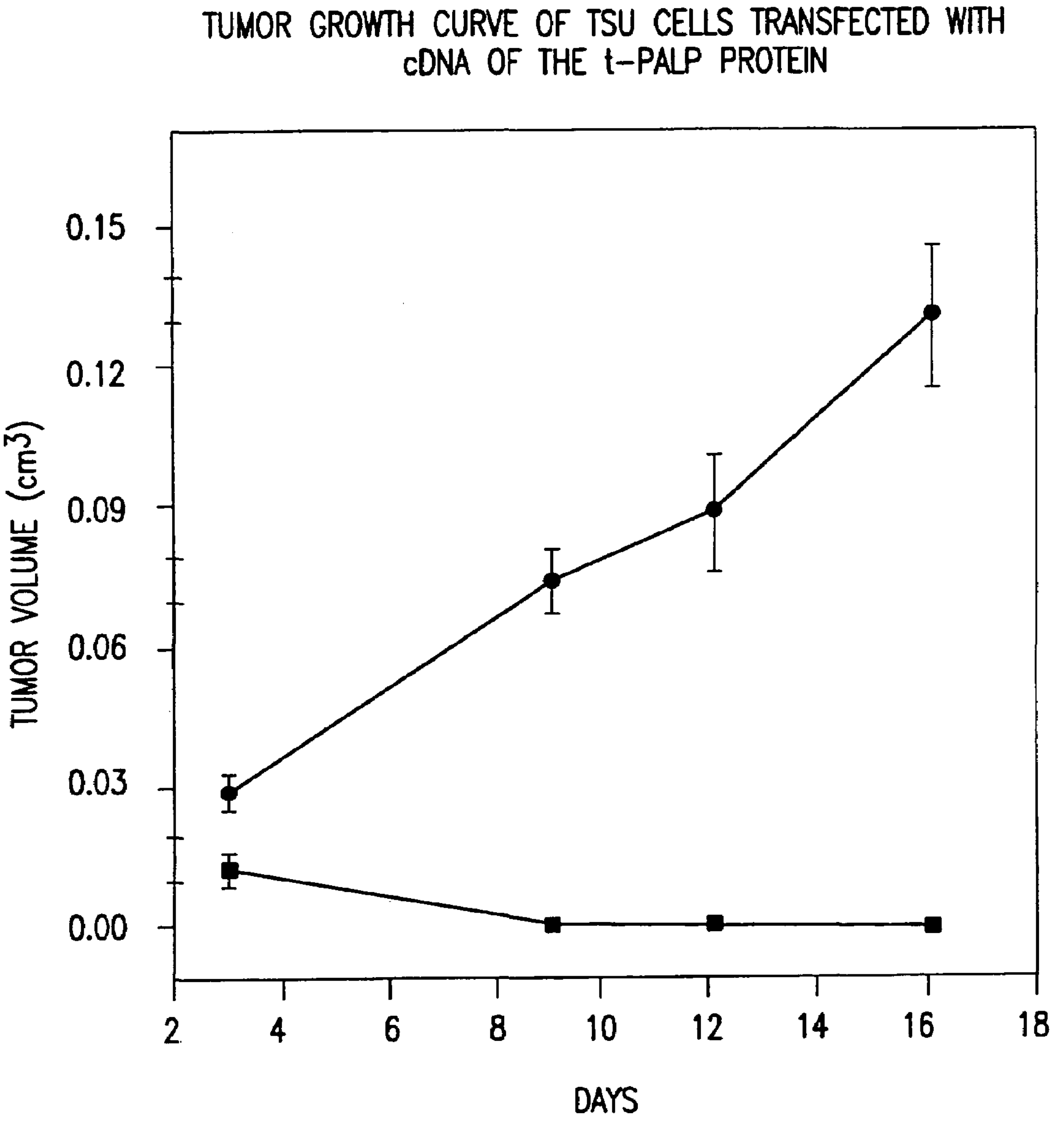

FIG. 6 shows that tumor growth in nude mice is significantly inhibited when the mice are injected with tumorigenic cells transiently transfected with t-PALP cDNA as compared to tumorigenic cells transiently transfected with expression vector only. In this assay, tumorigenic TSU cells were either transfected with expression vector only or transfected with t-PALP cDNA. The cells were then harvested with with 10 mM EDTA-PBS. One million tumor cells suspended in 0.2 ml of DMEM per side were injected subcutaneously into 6 week old nude mice. Five mice were used in each group. The tumor size was measured twice a week. The mice were sacrificed 4 weeks later and the tumors were removed, weighed, and measured. The mean +/− standard error was calculated and subjected to student's t-test. Tumor size of mock transfected cells is indicated by closed circles. Tumor size of t-PALP transfected cells is indicated by closed squares.

TABLE 1

| Residue | Pos. # | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −1.16 | 0.77 | . | . | . | −0.60 | 0.25 |
| Leu | 2 | A | A | . | . | . | . | . | −1.62 | 1.26 | . | . | . | −0.60 | 0.21 |
| Leu | 3 | A | A | . | . | . | . | . | −1.23 | 1.47 | . | . | . | −0.60 | 0.12 |
| Ala | 4 | A | A | . | . | . | . | . | −1.43 | 1.44 | * | . | . | −0.60 | 0.21 |
| Trp | 5 | A | A | . | . | . | . | . | −1.74 | 1.33 | * | . | . | −0.60 | 0.26 |
| Val | 6 | A | A | . | . | . | . | . | −1.96 | 1.43 | . | . | . | −0.60 | 0.27 |
| Gln | 7 | A | A | . | . | . | . | . | −2.00 | 1.43 | . | . | . | −0.60 | 0.22 |

TABLE 1-continued

| Residue | Pos. # | I | II | III | IV | V | VI | VII | VIII | IX | X | XI | XII | XIII | XIV |
|---|---|---|---|---|---|---|---|---|---|---|---|---|---|---|---|
| Ala | 8 | A | A | . | . | . | . | . | −1.49 | 1.57 | . | . | . | −0.60 | 0.16 |
| Phe | 9 | A | A | . | . | . | . | . | −0.90 | 1.04 | . | . | . | −0.60 | 0.28 |
| Leu | 10 | A | A | . | . | . | . | . | −1.21 | 0.80 | . | . | . | −0.60 | 0.26 |
| Val | 11 | A | A | . | . | . | . | . | −1.17 | 1.01 | . | . | . | −0.60 | 0.26 |
| Ser | 12 | A | A | . | . | . | . | . | −1.98 | 1.20 | . | . | . | −0.60 | 0.25 |
| Asn | 13 | A | A | . | . | . | . | . | −1.98 | 1.10 | . | . | . | −0.60 | 0.25 |
| Met | 14 | A | A | . | . | . | . | . | −1.28 | 0.91 | . | . | . | −0.60 | 0.34 |
| Leu | 15 | A | A | . | . | . | . | . | −1.06 | 0.27 | . | . | . | −0.30 | 0.43 |
| Leu | 16 | A | A | . | . | . | . | . | −0.44 | 0.39 | . | . | . | −0.30 | 0.27 |
| Ala | 17 | A | A | . | . | . | . | . | −0.49 | 0.74 | . | . | . | −0.60 | 0.43 |
| Glu | 18 | A | A | . | . | . | . | . | −0.79 | 0.56 | . | . | . | −0.53 | 0.52 |
| Ala | 19 | A | A | . | . | . | . | . | −0.53 | 0.26 | . | . | . | −0.16 | 0.84 |
| Tyr | 20 | . | A | . | . | T | . | . | −0.07 | 0.00 | . | . | . | 0.31 | 0.82 |
| Gly | 21 | . | . | . | . | T | T | . | 0.08 | −0.07 | . | . | F | 1.53 | 0.47 |
| Ser | 22 | . | . | . | . | T | T | . | −0.03 | 0.50 | . | . | F | 0.70 | 0.25 |
| Gly | 23 | . | . | . | . | T | T | . | −0.32 | 0.79 | * | . | F | 0.63 | 0.14 |
| Gly | 24 | . | . | . | . | T | T | . | 0.27 | 0.94 | * | . | F | 0.56 | 0.15 |
| Cys | 25 | . | . | B | . | . | . | . | 0.51 | 0.51 | * | . | . | −0.26 | 0.18 |
| Phe | 26 | . | . | B | . | . | . | . | 0.51 | 0.53 | . | . | . | −0.33 | 0.30 |
| Trp | 27 | . | . | B | . | . | T | . | 0.78 | 0.53 | . | . | . | −0.20 | 0.30 |
| Asp | 28 | . | . | B | . | . | T | . | 0.31 | 0.60 | . | . | F | −0.05 | 0.75 |
| Asn | 29 | . | . | . | . | T | T | . | 0.41 | 0.71 | . | . | F | 0.35 | 0.72 |
| Gly | 30 | . | . | . | . | T | T | . | 1.19 | 0.69 | * | . | F | 0.50 | 1.07 |
| His | 31 | . | A | . | . | . | . | C | 1.89 | −0.23 | . | . | . | 0.65 | 1.26 |
| Leu | 32 | . | A | . | . | . | . | C | 2.18 | −0.23 | . | . | . | 0.65 | 1.35 |
| Tyr | 33 | . | A | . | . | . | . | C | 2.18 | −0.63 | . | . | . | 1.29 | 2.28 |
| Arg | 34 | . | A | B | . | . | . | . | 1.87 | −0.66 | . | . | F | 1.58 | 2.91 |
| Glu | 35 | . | A | B | . | . | . | . | 1.91 | −0.67 | * | . | F | 1.92 | 5.09 |
| Asp | 36 | . | . | . | . | T | T | . | 1.73 | −0.97 | * | . | F | 3.06 | 4.35 |
| Gln | 37 | . | . | . | . | T | T | . | 1.96 | −1.30 | . | . | F | 3.40 | 3.43 |
| Thr | 38 | . | . | . | . | . | T | C | 1.99 | −0.80 | . | . | F | 2.86 | 2.00 |
| Ser | 39 | . | . | . | . | . | T | C | 1.53 | −0.37 | . | . | F | 2.35 | 1.85 |
| Pro | 40 | . | . | . | . | . | . | C | 0.72 | 0.06 | . | * | F | 1.34 | 1.06 |
| Ala | 41 | . | . | . | . | . | T | C | 0.83 | 0.34 | . | * | F | 1.18 | 0.61 |
| Pro | 42 | . | . | . | . | T | T | . | 0.17 | −0.14 | * | * | F | 1.77 | 0.89 |
| Gly | 43 | . | . | . | . | T | T | . | −0.33 | 0.04 | * | . | F | 1.30 | 0.31 |
| Leu | 44 | . | . | B | . | . | T | . | −0.03 | 0.30 | * | . | . | 0.62 | 0.25 |
| Arg | 45 | . | . | B | . | . | . | . | −0.11 | 0.20 | * | . | . | 0.29 | 0.26 |
| Cys | 46 | . | . | B | . | . | T | . | −0.33 | 0.69 | * | . | . | 0.06 | 0.28 |
| Leu | 47 | . | . | B | . | . | T | . | −0.12 | 0.94 | * | * | . | −0.07 | 0.28 |
| Asn | 48 | . | . | B | . | . | T | . | −0.37 | 0.26 | * | * | . | 0.10 | 0.24 |
| Trp | 49 | . | . | B | . | . | T | . | 0.44 | 0.76 | * | * | . | −0.20 | 0.44 |
| Leu | 50 | . | . | B | . | . | . | . | 0.03 | 0.59 | * | . | . | −0.40 | 0.93 |
| Asp | 51 | A | . | . | . | . | . | . | 0.36 | 0.29 | . | . | . | −0.01 | 0.78 |
| Ala | 52 | A | . | . | . | . | . | . | 0.36 | 0.31 | . | . | F | 0.23 | 0.73 |
| Gln | 53 | . | . | B | . | . | T | . | −0.23 | 0.09 | * | . | F | 0.52 | 0.73 |
| Ser | 54 | . | . | . | . | . | T | C | −0.24 | −0.10 | . | . | F | 1.41 | 0.44 |
| Gly | 55 | . | . | . | . | . | T | C | −0.02 | 0.29 | . | * | F | 0.90 | 0.59 |
| Leu | 56 | . | . | . | . | . | T | C | −0.23 | 0.29 | . | * | F | 0.81 | 0.34 |
| Ala | 57 | . | . | B | . | . | . | . | −0.50 | 0.31 | . | . | . | 0.17 | 0.40 |
| Ser | 58 | . | . | B | . | . | . | . | −0.80 | 0.57 | . | . | . | −0.22 | 0.30 |
| Ala | 59 | . | . | B | . | . | . | . | −0.84 | 0.53 | . | . | . | −0.31 | 0.48 |
| Pro | 60 | . | . | B | . | . | . | . | −1.09 | 0.27 | . | . | . | −0.10 | 0.47 |
| Val | 61 | . | . | B | . | . | . | . | −0.62 | 0.27 | . | * | . | −0.10 | 0.36 |
| Ser | 62 | . | . | B | . | . | . | . | −0.03 | 0.31 | . | * | F | 0.05 | 0.35 |
| Gly | 63 | . | . | . | . | T | T | . | 0.23 | 0.21 | . | * | F | 0.65 | 0.36 |
| Ala | 64 | . | . | . | . | T | T | . | 0.52 | 0.29 | . | * | F | 0.65 | 0.67 |
| Gly | 65 | . | . | . | . | T | T | . | 0.49 | 0.03 | . | . | F | 0.65 | 0.67 |
| Asn | 66 | . | . | . | . | T | T | . | 0.68 | 0.40 | . | * | . | 0.35 | 1.05 |
| His | 67 | . | . | B | . | . | T | . | 1.09 | 0.54 | . | . | . | −0.20 | 0.56 |
| Ser | 68 | . | . | B | . | . | T | . | 1.43 | 0.04 | . | . | . | 0.25 | 1.11 |
| Tyr | 69 | . | . | B | . | . | T | . | 1.81 | 0.01 | * | . | . | 0.59 | 1.11 |
| Cys | 70 | . | . | . | . | T | T | . | 2.16 | 0.04 | * | . | . | 1.33 | 1.26 |
| Arg | 71 | . | . | . | . | T | . | . | 2.16 | −0.46 | * | . | F | 2.22 | 1.57 |
| Asn | 72 | . | . | B | . | . | T | . | 2.19 | −0.84 | * | . | F | 2.66 | 1.73 |
| Pro | 73 | . | . | . | . | T | T | . | 2.28 | −1.60 | * | * | F | 3.40 | 5.39 |
| Asp | 74 | . | . | . | . | T | T | . | 2.63 | −1.74 | * | * | F | 3.06 | 4.26 |
| Glu | 75 | . | . | . | . | T | T | . | 2.96 | −1.74 | * | * | F | 2.93 | 5.18 |
| Asp | 76 | . | . | . | . | . | T | C | 2.63 | −1.71 | * | * | F | 2.60 | 3.32 |
| Pro | 77 | . | . | . | . | T | T | . | 2.34 | −1.71 | . | * | F | 2.67 | 3.07 |
| Arg | 78 | . | . | . | . | T | T | . | 1.89 | −0.80 | * | * | F | 2.54 | 1.87 |
| Gly | 79 | . | . | . | . | . | T | C | 1.64 | −0.23 | * | * | F | 2.10 | 0.60 |
| Pro | 80 | . | . | . | B | T | . | . | 0.79 | 0.53 | * | * | F | 0.79 | 0.61 |
| Trp | 81 | . | . | . | B | T | . | . | 0.49 | 0.74 | . | * | . | 0.43 | 0.23 |
| Cys | 82 | . | . | B | B | . | . | . | 0.36 | 1.13 | . | * | . | −0.18 | 0.31 |
| Tyr | 83 | . | . | B | B | . | . | . | 0.24 | 1.13 | . | * | . | −0.39 | 0.20 |
| Val | 84 | . | . | B | . | . | T | . | −0.00 | 0.70 | . | . | . | −0.20 | 0.33 |

TABLE 1-continued

| Residue | Pos. # | I | II | III | IV | V | VI | VII | VIII | IX | X | XI | XII | XIII | XIV |
|---|---|---|---|---|---|---|---|---|---|---|---|---|---|---|---|
| Ser | 85 | . | . | B | . | . | T | . | −0.13 | 0.29 | . | * | F | 0.25 | 0.62 |
| Gly | 86 | . | . | . | . | . | T | C | −0.70 | 0.14 | . | * | F | 0.45 | 0.39 |
| Glu | 87 | . | . | . | . | T | T | . | −0.24 | 0.03 | . | * | F | 0.65 | 0.39 |
| Ala | 88 | . | . | . | . | . | . | C | −0.00 | −0.19 | . | * | F | 0.85 | 0.45 |
| Gly | 89 | . | . | . | . | . | . | C | 0.90 | −0.57 | . | * | F | 1.15 | 0.79 |
| Val | 90 | . | . | . | . | . | . | C | 1.31 | −1.00 | . | . | F | 1.15 | 0.91 |
| Pro | 91 | A | . | . | . | . | . | . | 1.44 | −1.00 | . | . | F | 1.44 | 1.77 |
| Glu | 92 | . | . | . | . | T | . | . | 0.78 | −1.07 | * | . | F | 2.18 | 2.76 |
| Lys | 93 | A | . | . | . | . | . | . | 1.37 | −0.93 | * | . | F | 2.12 | 1.99 |
| Arg | 94 | . | . | B | . | . | T | . | 1.71 | −1.57 | * | . | F | 2.66 | 2.23 |
| Pro | 95 | . | . | . | . | T | T | . | 1.76 | −2.00 | * | * | F | 3.40 | 2.15 |
| Cys | 96 | . | . | . | . | T | T | . | 2.08 | −1.31 | * | * | F | 2.91 | 0.89 |
| Glu | 97 | A | . | . | . | . | T | . | 1.41 | −1.31 | * | * | F | 2.17 | 0.89 |
| Asp | 98 | . | . | . | . | T | . | . | 1.16 | −0.74 | * | * | F | 2.03 | 0.31 |
| Leu | 99 | . | . | . | . | T | . | . | 1.04 | −0.74 | * | * | . | 1.85 | 0.89 |
| Arg | 100 | . | . | B | . | . | . | . | 0.94 | −1.31 | * | * | . | 1.42 | 0.89 |
| Cys | 101 | . | . | B | . | . | T | . | 1.30 | −0.83 | * | * | F | 2.08 | 0.77 |
| Pro | 102 | . | . | . | . | T | T | . | 1.00 | −0.34 | * | * | F | 2.64 | 1.34 |
| Glu | 103 | . | . | . | . | T | T | . | 1.00 | −0.64 | * | * | F | 3.10 | 0.92 |
| Thr | 104 | A | . | . | . | . | T | . | 1.22 | −0.24 | * | * | F | 2.24 | 2.97 |
| Thr | 105 | A | A | . | . | . | . | . | 0.30 | −0.31 | * | . | F | 1.53 | 1.94 |
| Ser | 106 | . | A | B | . | . | . | . | 0.76 | −0.06 | * | . | F | 1.07 | 0.92 |
| Gln | 107 | . | A | B | . | . | . | . | 0.38 | 0.37 | * | . | F | 0.16 | 0.99 |
| Ala | 108 | . | A | B | . | . | . | . | −0.32 | 0.39 | * | . | . | −0.30 | 0.69 |
| Leu | 109 | . | A | . | . | . | . | C | −0.32 | 0.69 | * | . | . | −0.40 | 0.45 |
| Pro | 110 | . | A | . | . | . | . | C | −0.32 | 0.79 | * | . | . | −0.40 | 0.37 |
| Ala | 111 | A | A | . | . | . | . | . | −0.02 | 0.87 | * | * | . | −0.60 | 0.53 |
| Phe | 112 | A | A | . | . | . | . | . | −0.91 | 0.37 | * | * | . | −0.15 | 1.12 |
| Thr | 113 | A | A | . | . | . | . | . | −0.32 | 0.37 | * | * | F | −0.15 | 0.51 |
| Thr | 114 | A | A | . | . | . | . | . | 0.49 | 0.34 | * | . | F | −0.15 | 0.87 |
| Glu | 115 | A | A | . | . | . | . | . | 0.11 | −0.16 | * | . | F | 0.60 | 1.74 |
| Ile | 116 | A | A | . | . | . | . | . | 0.40 | −0.44 | * | * | F | 0.60 | 1.22 |
| Gln | 117 | A | A | . | . | . | . | . | 1.10 | −0.54 | * | * | F | 0.90 | 1.13 |
| Glu | 118 | A | A | . | . | . | . | . | 1.07 | −1.03 | * | . | F | 0.90 | 1.13 |
| Ala | 119 | A | A | . | . | . | . | . | 1.17 | −0.60 | * | . | F | 1.20 | 1.60 |
| Ser | 120 | . | . | . | . | . | . | C | 0.82 | −0.86 | * | . | F | 1.90 | 1.42 |
| Glu | 121 | . | . | . | . | . | . | C | 1.12 | −0.83 | . | . | F | 2.05 | 0.81 |
| Gly | 122 | . | . | . | . | . | T | C | 1.12 | −0.33 | . | . | F | 2.25 | 0.81 |
| Pro | 123 | . | . | . | . | . | T | C | 1.12 | −0.83 | . | . | F | 3.00 | 1.01 |
| Gly | 124 | . | . | . | . | . | T | C | 0.86 | −1.21 | . | . | F | 2.70 | 1.01 |
| Ala | 125 | A | . | . | . | . | T | . | 1.16 | −0.57 | . | * | F | 2.05 | 0.76 |
| Asp | 126 | A | A | . | . | . | . | . | 0.30 | −0.60 | . | . | F | 1.35 | 0.85 |
| Glu | 127 | A | A | . | . | . | . | . | −0.06 | −0.39 | * | . | F | 0.75 | 0.64 |
| Val | 128 | . | A | B | . | . | . | . | −0.43 | −0.03 | * | . | . | 0.30 | 0.55 |
| Gln | 129 | . | A | B | . | . | . | . | −0.30 | −0.03 | * | * | . | 0.30 | 0.33 |
| Val | 130 | . | A | B | . | . | . | . | −0.30 | 0.40 | . | * | . | −0.60 | 0.30 |
| Phe | 131 | . | A | B | . | . | . | . | −0.30 | 0.90 | . | * | . | −0.60 | 0.40 |
| Ala | 132 | A | A | . | . | . | . | . | −0.89 | 0.66 | . | * | . | −0.60 | 0.37 |
| Pro | 133 | A | . | . | . | . | T | . | −0.84 | 0.76 | . | * | . | −0.20 | 0.51 |
| Ala | 134 | A | . | . | . | . | T | . | −1.06 | 0.80 | . | . | . | −0.20 | 0.48 |
| Asn | 135 | A | . | . | . | . | T | . | −0.79 | 0.44 | * | * | . | −0.20 | 0.74 |
| Ala | 136 | A | . | . | . | . | T | . | 0.02 | 0.44 | . | . | . | −0.20 | 0.48 |
| Leu | 137 | A | . | . | . | . | . | . | 0.31 | 0.01 | . | * | . | −0.10 | 0.94 |
| Pro | 138 | A | . | . | . | . | T | . | 0.52 | −0.10 | . | * | . | 0.70 | 0.78 |
| Ala | 139 | A | . | . | . | . | T | . | 0.52 | −0.50 | . | * | F | 1.00 | 1.34 |
| Arg | 140 | A | . | . | . | . | T | . | −0.07 | −0.50 | . | * | F | 1.00 | 1.64 |
| Ser | 141 | A | . | . | . | . | T | . | −0.07 | −0.69 | . | * | F | 1.30 | 1.07 |
| Glu | 142 | A | A | . | . | . | . | . | −0.11 | −0.61 | . | * | F | 0.90 | 1.07 |
| Ala | 143 | A | A | . | . | . | . | . | 0.10 | −0.47 | * | * | . | 0.30 | 0.41 |
| Ala | 144 | A | A | . | . | . | . | . | 0.48 | −0.07 | * | * | . | 0.30 | 0.53 |
| Ala | 145 | A | A | . | . | . | . | . | −0.49 | −0.03 | * | * | . | 0.30 | 0.47 |
| Val | 146 | A | A | . | . | . | . | . | −1.08 | 0.61 | . | . | . | −0.60 | 0.35 |
| Gln | 147 | . | A | B | . | . | . | . | −1.42 | 0.80 | . | . | . | −0.60 | 0.24 |
| Pro | 148 | . | A | B | . | . | . | . | −1.72 | 0.73 | . | * | . | −0.60 | 0.23 |
| Val | 149 | . | . | B | B | . | . | . | −1.43 | 0.91 | * | * | . | −0.60 | 0.22 |
| Ile | 150 | . | . | B | B | . | . | . | −0.84 | 0.66 | * | * | . | −0.60 | 0.17 |
| Gly | 151 | . | . | B | B | . | . | . | 0.12 | 0.66 | * | * | . | −0.60 | 0.19 |
| Ile | 152 | . | . | B | B | . | . | . | −0.73 | 0.23 | * | * | . | −0.30 | 0.51 |
| Ser | 153 | . | . | B | B | . | . | . | −0.41 | 0.23 | * | * | F | −0.15 | 0.54 |
| Gln | 154 | . | . | B | B | . | . | . | −0.16 | −0.46 | * | * | F | 0.60 | 1.06 |
| Arg | 155 | . | . | B | B | . | . | . | 0.73 | −0.27 | . | * | F | 0.60 | 1.50 |
| Val | 156 | . | . | B | B | . | . | . | 0.78 | −0.56 | * | * | . | 0.75 | 1.80 |
| Arg | 157 | . | . | B | . | . | T | . | 1.71 | −0.56 | * | * | . | 1.15 | 1.39 |
| Met | 158 | A | . | . | . | . | T | . | 2.01 | −0.96 | . | * | . | 1.15 | 1.42 |
| Asn | 159 | A | . | . | . | . | T | . | 2.06 | −0.96 | . | * | F | 1.30 | 3.32 |
| Ser | 160 | A | . | . | . | . | T | . | 1.99 | −1.60 | . | * | F | 1.30 | 3.39 |
| Lys | 161 | A | A | . | . | . | . | . | 2.84 | −1.60 | * | * | F | 0.90 | 6.84 |

TABLE 1-continued

| Residue | Pos. # | I | II | III | IV | V | VI | VII | VIII | IX | X | XI | XII | XIII | XIV |
|---|---|---|---|---|---|---|---|---|---|---|---|---|---|---|---|
| Glu | 162 | A | A | . | . | . | . | . | 1.92 | −2.21 | * | * | F | 0.90 | 7.11 |
| Lys | 163 | A | A | . | . | . | . | . | 2.18 | −1.93 | . | * | F | 0.90 | 4.37 |
| Lys | 164 | A | A | . | . | . | . | . | 1.87 | −1.89 | . | . | F | 0.90 | 2.16 |
| Asp | 165 | A | A | . | B | . | . | . | 1.36 | −1.40 | * | . | F | 0.90 | 1.80 |
| Leu | 166 | . | A | B | B | . | . | . | 0.97 | −0.71 | * | . | F | 0.75 | 0.74 |
| Gly | 167 | . | . | B | B | . | . | . | 0.72 | −0.29 | . | . | F | 0.45 | 0.37 |
| Thr | 168 | . | . | B | B | . | . | . | −0.18 | 0.47 | * | . | F | −0.45 | 0.35 |
| Leu | 169 | . | . | B | B | . | . | . | −1.03 | 1.11 | * | . | . | −0.60 | 0.31 |
| Gly | 170 | . | . | B | B | . | . | . | −1.38 | 1.11 | . | . | . | −0.60 | 0.26 |
| Tyr | 171 | . | . | B | B | . | . | . | −1.46 | 1.11 | . | . | . | −0.60 | 0.18 |
| Val | 172 | . | . | B | B | . | . | . | −1.42 | 1.31 | . | . | . | −0.60 | 0.15 |
| Leu | 173 | . | . | B | B | . | . | . | −1.71 | 1.11 | . | . | . | −0.60 | 0.22 |
| Gly | 174 | . | . | B | B | . | . | . | −1.50 | 1.30 | . | . | . | −0.60 | 0.14 |
| Ile | 175 | . | . | B | B | . | . | . | −2.01 | 1.16 | . | . | . | −0.60 | 0.19 |
| Thr | 176 | . | . | B | B | . | . | . | −2.66 | 1.16 | . | . | . | −0.60 | 0.17 |
| Met | 177 | . | . | B | B | . | . | . | −2.69 | 1.16 | . | . | . | −0.60 | 0.12 |
| Met | 178 | . | . | B | B | . | . | . | −2.77 | 1.41 | . | . | . | −0.60 | 0.12 |
| Val | 179 | . | . | B | B | . | . | . | −3.01 | 1.41 | . | . | . | −0.60 | 0.06 |
| Ile | 180 | . | . | B | B | . | . | . | −3.01 | 1.43 | . | . | . | −0.60 | 0.06 |
| Ile | 181 | . | . | B | B | . | . | . | −3.04 | 1.50 | . | . | . | −0.60 | 0.04 |
| Ile | 182 | . | . | B | B | . | . | . | −3.03 | 1.31 | . | . | . | −0.60 | 0.06 |
| Ala | 183 | . | . | B | B | . | . | . | −2.78 | 1.17 | . | . | . | −0.60 | 0.08 |
| Ile | 184 | A | . | . | B | . | . | . | −2.81 | 0.91 | . | . | . | −0.60 | 0.11 |
| Gly | 185 | . | . | B | . | . | T | . | −2.81 | 0.91 | . | . | . | −0.20 | 0.11 |
| Ala | 186 | . | . | B | . | . | T | . | −2.73 | 0.91 | . | . | . | −0.20 | 0.08 |
| Gly | 187 | . | . | B | . | . | T | . | −2.19 | 1.10 | . | . | . | −0.20 | 0.09 |
| Ile | 188 | . | . | B | . | . | T | . | −1.84 | 0.84 | . | . | . | −0.20 | 0.09 |
| Ile | 189 | . | . | B | B | . | . | . | −1.26 | 1.17 | . | . | . | −0.60 | 0.14 |
| Leu | 190 | . | . | B | B | . | . | . | −1.16 | 1.06 | . | . | . | −0.60 | 0.19 |
| Gly | 191 | . | . | B | B | . | . | . | −0.52 | 1.39 | * | . | . | −0.26 | 0.43 |
| Tyr | 192 | . | . | B | . | . | T | . | −0.07 | 0.70 | * | . | . | 0.63 | 1.23 |
| Ser | 193 | . | . | B | . | . | T | . | 0.48 | 0.01 | . | * | . | 1.27 | 2.92 |
| Tyr | 194 | . | . | . | . | T | T | . | 1.41 | −0.24 | * | . | . | 2.61 | 2.92 |
| Lys | 195 | . | . | . | . | T | T | . | 2.22 | −0.67 | * | . | F | 3.40 | 3.73 |
| Arg | 196 | . | . | . | . | T | . | . | 1.76 | −1.43 | . | . | F | 2.86 | 4.65 |
| Gly | 197 | . | . | . | . | T | T | . | 2.04 | −1.13 | * | . | F | 2.72 | 2.45 |
| Lys | 198 | A | . | . | . | . | T | . | 2.34 | −1.89 | * | . | F | 1.98 | 2.45 |
| Asp | 199 | A | . | . | . | . | T | . | 2.59 | −1.89 | * | . | F | 1.64 | 2.16 |
| Leu | 200 | A | . | . | . | . | T | . | 2.51 | −1.49 | * | . | F | 1.30 | 3.79 |
| Lys | 201 | A | A | . | . | . | . | . | 2.40 | −1.41 | * | . | F | 0.90 | 2.58 |
| Glu | 202 | A | A | . | . | . | . | . | 2.74 | −1.41 | * | * | F | 0.90 | 2.58 |
| Gln | 203 | A | A | . | . | . | . | . | 2.74 | −1.01 | * | * | F | 0.90 | 5.41 |
| His | 204 | A | A | . | . | . | . | . | 1.89 | −1.70 | . | * | F | 0.90 | 5.41 |
| Asp | 205 | A | A | . | . | . | . | . | 2.03 | −1.06 | . | .* | F | 0.90 | 2.32 |
| Gln | 206 | A | A | . | . | . | . | . | 1.99 | −0.49 | * | * | F | 0.45 | 0.72 |
| Lys | 207 | A | A | . | . | . | . | . | 2.10 | −0.89 | * | * | F | 0.75 | 0.91 |
| Val | 208 | A | A | . | . | . | . | . | 2.10 | −1.39 | * | * | F | 0.90 | 1.07 |
| Cys | 209 | A | A | . | . | . | . | . | 1.53 | −1.39 | * | . | . | 0.75 | 1.07 |
| Glu | 210 | A | A | . | . | . | . | . | 1.53 | −1.17 | * | * | . | 0.60 | 0.53 |
| Arg | 211 | A | A | . | . | . | . | . | 1.64 | −0.77 | * | * | . | 0.75 | 1.24 |
| Glu | 212 | A | A | . | . | . | . | . | 0.71 | −1.41 | * | * | F | 0.90 | 4.52 |
| Met | 213 | A | A | . | . | . | . | . | 1.26 | −1.30 | * | * | F | 0.90 | 1.83 |
| Gln | 214 | A | A | . | . | . | . | . | 1.11 | −0.81 | * | * | F | 0.90 | 1.35 |
| Arg | 215 | A | A | . | . | . | . | . | 0.90 | −0.13 | * | * | . | 0.30 | 0.64 |
| Ile | 216 | . | A | B | . | . | . | . | −0.02 | 0.30 | * | * | . | −0.15 | 1.00 |
| Thr | 217 | . | A | B | . | . | . | . | −0.32 | 0.37 | * | * | . | −0.30 | 0.48 |
| Leu | 218 | . | A | B | . | . | . | . | −0.31 | 0.36 | * | * | . | −0.30 | 0.33 |
| Pro | 219 | . | A | B | . | . | . | . | −1.01 | 0.86 | * | * | . | −0.60 | 0.47 |
| Leu | 220 | . | . | B | . | . | . | . | −1.43 | 0.96 | * | * | . | −0.40 | 0.28 |
| Ser | 221 | . | . | B | . | . | . | . | −0.54 | 0.96 | * | * | . | −0.40 | 0.49 |
| Ala | 222 | . | . | . | . | T | . | . | −0.44 | 0.67 | . | . | . | 0.00 | 0.51 |
| Phe | 223 | . | . | . | . | T | . | . | 0.06 | 0.67 | . | . | . | 0.00 | 0.96 |
| Thr | 224 | . | . | . | . | . | . | C | −0.40 | 0.47 | * | . | F | 0.10 | 1.04 |
| Asn | 225 | . | . | . | . | . | T | C | 0.41 | 0.66 | * | * | F | 0.15 | 0.55 |
| Pro | 226 | . | . | . | . | . | T | C | −0.18 | 0.16 | * | . | F | 0.60 | 1.10 |
| Thr | 227 | . | . | . | . | T | T | . | −0.44 | 0.06 | * | . | F | 0.65 | 0.54 |
| Cys | 228 | A | . | . | . | . | T | . | 0.26 | 0.21 | * | . | . | 0.10 | 0.25 |
| Glu | 229 | A | . | . | B | . | . | . | 0.57 | −0.19 | . | . | . | 0.30 | 0.27 |
| Ile | 230 | A | . | . | B | . | . | . | 0.61 | −0.61 | . | . | . | 0.60 | 0.32 |
| Val | 231 | A | . | . | B | . | . | . | 0.51 | −1.10 | . | . | . | 0.75 | 1.19 |
| Asp | 232 | A | . | . | B | . | . | . | −0.03 | −1.19 | . | . | F | 0.75 | 1.00 |
| Glu | 233 | A | . | . | B | . | . | . | −0.22 | −0.54 | . | . | F | 0.90 | 1.05 |
| Lys | 234 | A | . | . | B | . | . | . | −1.08 | −0.59 | . | . | F | 0.90 | 1.05 |
| Thr | 235 | A | . | . | B | . | . | . | −0.22 | −0.59 | . | . | F | 0.75 | 0.47 |
| Val | 236 | A | . | . | B | . | . | . | 0.32 | −0.09 | . | . | . | 0.30 | 0.37 |
| Val | 237 | . | . | B | B | . | . | . | 0.02 | 0.40 | . | . | . | −0.30 | 0.27 |
| Val | 238 | . | . | B | B | . | . | . | 0.02 | 0.79 | . | . | . | −0.60 | 0.25 |

TABLE 1-continued

| Residue | Pos. # | I | II | III | IV | V | VI | VII | VIII | IX | X | XI | XII | XIII | XIV |
|---|---|---|---|---|---|---|---|---|---|---|---|---|---|---|---|
| His | 239 | . | . | B | . | . | T | . | −0.33 | 0.70 | . | . | . | −0.20 | 0.58 |
| Thr | 240 | . | . | B | . | . | T | . | −0.23 | 0.54 | . | . | F | 0.10 | 1.12 |
| Ser | 241 | . | . | . | . | T | T | . | −0.23 | 0.33 | * | . | F | 0.80 | 2.33 |
| Gln | 242 | . | . | . | . | . | T | C | 0.62 | 0.33 | * | . | F | 0.60 | 1.27 |
| Thr | 243 | . | . | . | . | . | . | C | 1.27 | −0.17 | . | * | F | 1.00 | 1.47 |
| Pro | 244 | . | . | . | . | . | . | C | 1.30 | −0.23 | . | * | F | 1.34 | 1.70 |
| Val | 245 | . | . | B | . | . | . | . | 1.61 | −0.21 | . | . | F | 1.48 | 1.70 |
| Asp | 246 | . | . | B | . | . | . | . | 1.57 | −0.61 | . | . | F | 2.12 | 2.04 |
| Pro | 247 | . | . | B | . | . | T | . | 1.27 | −0.67 | . | * | F | 2.66 | 1.30 |
| Gln | 248 | . | . | . | . | T | T | . | 1.27 | −0.71 | . | . | F | 3.40 | 2.35 |
| Glu | 249 | . | . | . | . | T | T | . | 1.27 | −0.87 | . | . | F | 3.06 | 2.03 |
| Gly | 250 | . | . | . | . | T | T | . | 1.31 | −0.44 | . | . | F | 2.42 | 2.03 |
| Ser | 251 | . | . | . | . | . | . | C | 0.71 | −0.19 | . | . | F | 1.53 | 0.97 |
| Thr | 252 | . | . | B | . | . | . | . | 0.58 | 0.03 | . | . | F | 0.39 | 0.55 |
| Pro | 253 | . | . | B | . | . | . | . | 0.58 | 0.46 | . | * | F | −0.25 | 0.55 |
| Leu | 254 | . | . | B | . | . | . | . | −0.01 | 0.43 | . | * | F | −0.25 | 0.72 |
| Met | 255 | . | . | B | . | . | . | . | −0.01 | 0.54 | . | . | . | −0.40 | 0.50 |
| Gly | 256 | . | . | B | . | . | . | . | −0.02 | 0.49 | . | . | . | −0.40 | 0.32 |
| Gln | 257 | . | . | B | . | . | . | . | 0.08 | 0.54 | . | . | F | −0.25 | 0.56 |
| Ala | 258 | . | . | B | . | . | . | . | −0.06 | 0.29 | . | . | F | 0.05 | 0.88 |
| Gly | 259 | . | . | . | . | . | . | C | 0.17 | 0.10 | . | . | F | 0.25 | 0.88 |
| Thr | 260 | . | . | . | . | . | T | C | 0.38 | 0.17 | * | . | F | 0.45 | 0.51 |
| Pro | 261 | . | . | . | . | . | T | C | 0.33 | 0.20 | . | . | . | 0.30 | 0.65 |
| Gly | 262 | . | . | . | . | . | T | C | −0.06 | 0.13 | . | . | . | 0.30 | 0.84 |
| Ala | 263 | . | . | B | . | . | T | . | 0.14 | 0.13 | . | . | . | 0.10 | 0.74 |

DETAILED DESCRIPTION

The present invention provides isolated nucleic acid molecules comprising a polynucleotide encoding a t-PALP polypeptide having the amino acid sequence shown in SEQ ID NO:2, which was determined by sequencing a cloned cDNA. The nucleotide sequence shown in FIGS. 1A, 1B, and 1C (SEQ ID NO:1) was obtained by sequencing the HMSIB42 clone, which was deposited on May 8, 1997 at the American Type Culture Collection, 10801 University Drive, Manassas, Va. 20110-2209, and given accession number ATCC 209023. The deposited clone is contained in the pBluescript SK(−) plasmid (Stratagene, La Jolla, Calif.).

The t-PALP protein of the present invention shares sequence homology with the translation product of the human mRNA for t-PA (FIG. 2) (SEQ ID NO:3). t-PA is thought to be an important regulator of the dissolution of fibrin clots in humans and other animals. Abnormal blood clotting can lead to many vascular diseases, such as stroke, deep-vein thrombosis, peripheral arterial occlusion, pulmonary embolism, and myocardiothrombosis, each of which constitutes a major health risk. Such diseases are primarily caused by partial or total occlusion of a blood vessel by a blood clot. Such clots consist essentially of a mass of fibrin and platelets. The dissolution of existing clots is frequently achieved by the activation of plasminogen which dissolves the existing blood clot (thereby affecting the fibrinolysis pathway).

The fibrinolytic system is activated by the deposition of fibrin. t-PA activates plasminogen and, only upon activation, can plasminogen degrade fibrin, and, ultimately, degrade the blood clot itself.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule (these values may also be expressed as at most 10% different, more typically at most about 5% to about 0.1% different from the actual nucleotide sequence of the sequenced DNA molecule). The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A, 1B, and 1C (SEQ ID NO:1), a nucleic acid molecule of the present invention encoding a t-PALP polypeptide may be obtained using standard cloning and screening procedures, such as those for cloning cDNAs using mRNA as starting material. Illustrative of the invention, the nucleic acid molecule described in FIGS. 1A, 1B, and 1C (SEQ ID NO:1) was discovered in a cDNA library derived from activated monocytes.

Additional clones of the same gene were also identified in cDNA libraries from the following tissues: cerebellum, smooth muscle, resting and PHA-treated T-cells, GM-CSF-treated macrophages, frontal cortex of the brain, breast lymph node, chronic lymphocytic leukemic spleen, and several others. Thus, in one embodiment, polynucleotides, polypeptides, and antibodies of the invention may be used to distinguish between tissues. In a preferred embodiment, polynucleotides, polypeptides, and antibodies of the invention may be used to distinguish between tissues recited in the above paragraph and in tissues not recited in the above paragraph.

A Northern blot analysis of the t-PALP clone of FIGS. 1A, 1B, and 1C (SEQ ID NO:1), or the t-PALP clone contained in ATCC Deposit No. 209023, indicated that 2.5 kb t-PALP message is detectable in heart, brain, placenta, lung, liver, skeletal muscle, kidney, pancreas, spleen, thymus, prostate, testis, ovary, small intestine, colon, and peripheral blood leukocytes (see Example 4). Thus, in one embodiment, polynucleotides, polypeptides, and antibodies of the invention may be used to distinguish between tissues. In a preferred embodiment, polynucleotides, polypeptides, and antibodies of the invention may be used to distinguish between tissues recited in the above paragraph and in tissues not recited in the above paragraph. In an additional preferred embodiment, polynucleotides, polypeptides, and antibodies of the invention may be used to distinguish between human and non-human tissues.

The determined nucleotide sequence of the t-PALP cDNA of FIGS. 1A, 1B, and 1C (SEQ ID NO:1) contains an open reading frame encoding a protein of 263 amino acid residues, with an initiation codon at nucleotide positions 124–126 of the nucleotide sequence in FIGS. 1A, 1B, and 1C (SEQ ID NO:1), and a deduced molecular weight of about 28.2 kDa. An in vitro transcription/translation analysis of the t-PALP clone shown in SEQ ID NO:1, or the t-PALP clone contained in ATCC Deposit No. 209023, resulted in the production of a protein product of about 35 kDa. The amino acid sequence of the t-PALP protein shown in SEQ ID NO:2 is about 21.3% identical to human mRNA for t-PA (FIG. 2; Degen, S. J., Rajput, B., and Reich, E. (1986) J. Biol. Chem. 261:6972–6985; GenBank Accession No. K03021).

The open reading frame of the t-PALP gene shares sequence homology with the translation product of the human mRNA for t-PA (FIG. 2) (SEQ ID NO:3), including the following conserved domains: (a) the predicted kringle domain of about 59 amino acids, and (b) the predicted protease domain of about 179 amino acids. t-PA is thought to be important in the regulation of blood clotting and disorders related thereto. The homology between t-PA and t-PALP indicates that t-PALP may also be involved in the regulation of normal and abnormal clotting in such conditions including many vascular diseases, such as stroke, deep-vein thrombosis, peripheral arterial occlusion, pulmonary embolism, and myocardiothrombosis. In an additional embodiment t-PALP is involved in the regulation of angiogenesis and thus, may be useful in the treatment of cancers; for example solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; blood born tumors (such as leukemias); benign tumors, for example hemangiomas, acoustic neuromas, neurofibromas, trachomas, and pyogenic granulomas; artheroscleric plaques; ocular angiogenic diseases, for example diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

As one of ordinary skill would appreciate, due to the possibilities of sequencing errors discussed above, the actual complete t-PALP polypeptide encoded by the deposited cDNA, which comprises about 263 amino acids, may be somewhat longer or shorter. More generally, the actual open reading frame may be anywhere in the range of ±20 amino acids, more likely in the range of ±10 amino acids, of that predicted from the methionine codon at the N-terminus shown in FIGS. 1A, 1B, and 1C (SEQ ID NO:1). It will further be appreciated that, depending on the analytical criteria used for identifying various functional domains, the exact "address" of the kringle and protease domains of the t-PALP polypeptide may differ slightly from the predicted positions above. For example, the exact location of the t-PALP kringle and protease domains in SEQ ID NO:2 may vary slightly (e.g., the address may "shift" by about 1 to about 20 residues, more likely about 1 to about 5 residues) depending on the criteria used to define the domain.

Leader and Mature Sequences

The amino acid sequence of the complete t-PALP protein includes a leader sequence and a mature protein, as shown in SEQ ID NO:2. More in particular, the present invention provides nucleic acid molecules encoding a mature form of the t-PALP protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature t-PALP polypeptide having the amino acid sequence encoded by the cDNA clone contained in the host identified as ATCC Deposit No. 209023. By the "mature t-PALP polypeptide having the amino acid sequence encoded by the cDNA clone in ATCC Deposit No. 209023" is meant the mature form(s) of the t-PALP protein produced by expression in a mammalian cell (e.g., COS cells, as described below) of the complete open reading frame encoded by the human DNA sequence of the clone contained in the vector in the deposited host.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete t-PALP polypeptide was analyzed by a computer program PSORT, available from Dr. Kenta Nakai of the Institute for Chemical Research, Kyoto University (see K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. Thus, the computation analysis described above predicted a single cleavable N-terminal signal sequence within the complete amino acid sequence shown in SEQ ID NO:2.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread", as in a karyotype), is not "isolated" for the purposes of this invention. As discussed further herein, isolated nucleic acid molecules according to the present invention may be produced naturally, recombinantly, or synthetically.

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length. In additional specific embodiments, isolated polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

Isolated nucleic acid molecules of the present invention include DNA molecules comprising an open reading frame (ORF) with an initiation codon at positions 124–126 of the nucleotide sequence shown in FIGS. 1A, 1B, and 1C (SEQ ID NO:1).

Also included are DNA molecules comprising the coding sequence for the predicted mature t-PALP protein shown at positions 1–242 of SEQUENCE ID NO:2.

In addition, isolated nucleic acid molecules of the invention include DNA molecules which comprise a sequence substantially different from those described above but which, due to the degeneracy of the genetic code, still encode the t-PALP protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another embodiment, the invention provides isolated nucleic acid molecules encoding the t-PALP polypeptide having an amino acid sequence encoded by the cDNA clone contained in the plasmid deposited as ATCC Deposit No. 209023 on May 8, 1997.

Preferably, this nucleic acid molecule will encode the mature polypeptide encoded by the above-described deposited cDNA clone.

The invention further provides an isolated nucleic acid molecule having the nucleotide sequence shown in FIGS. 1A, 1B, and 1C (SEQ ID NO:1) or the nucleotide sequence of the t-PALP cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the t-PALP gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–915 of SEQ ID NO:1.

In addition, the invention provides nucleic acid molecules having nucleotide sequences related to extensive portions of SEQ ID NO:1 which have been determined from the following related cDNA clones: HTAAM28R (SEQ ID NO:4), HFKBA12R (SEQ ID NO:5), HAPBL24R (SEQ ID NO:6), HLMFG34R (SEQ ID NO:7), HHPGT42R (SEQ ID NO:8), HSSAX27R (SEQ ID NO:9), and HSSES93R (SEQ ID NO:10).

Further, the invention includes a polynucleotide comprising any portion of at least about 30 nucleotides, preferably at least about 50 nucleotides, of SEQ ID NO:1 from residue 1 to 110 and from 630 to 750. More preferably, the invention includes a polynucleotide comprising nucleotide residues 1 to 2000, 1 to 1500, 1 to 1000, 1 to 500, 1 to 250, 250 to 2000, 250 to 1500, 250 to 1000, 250 to 500, 500 to 2000, 500 to 1500, 500 to 1000, 1000 to 2000, and 1000 to 1500.

Moreover, representative examples of polynucleotide fragments of the invention, include, for example, fragments comprising, or alternatively consisting of, a sequence from about nucleotide number 1–60, 61–123, 1–168, 61–168, 124–168, 169–213, 214–258, 259–303, 304–348, 349–393, 394–438, 439–483, 484–528, 529–573, 574–618, 619–663, 664–708, 709–753, 754–798, 799–843, 844–888, 889–933, 934–978, 979–1023, 1024–1068, 1069–1113, 1114–1158, 1159–1203, 1204–1248, 1249–1293, 1294–1338, 1339–1383, 1384–1428, 1429–1473, 1474–1518, 1519–1563, 1564–1608, 1609–1653, 1654–1698, 1699–1743, 1744–1788, 1789–1833, 1834–1878, 1879–1923, 1924–1968, 1969–2013, 2014–2058, 2059–2103, 2104–2148, 2149–2193, 2194–2238, 2239–2283, 2284–2328, or 2284–2329 of SEQ ID NO:1, or the complementary strand thereto, or the cDNA contained in the deposited clone. In this context "about" includes the particularly recited ranges, and ranges larger or smaller by several (6, 5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

Representative examples of polynucleotide fragments of the invention, also include, for example, fragments comprising, or alternatively consisting of, a sequence from about nucleotide 1-123, 1-186, 1-195, 1-375, 124-186, 124-195, 124-375, 187-261, 196-261, 196-375, 196-912, 259-369, 259-375, 262-306, 262-333, 262-366, 262-375, 307-375, 328-345, 322-351, 376-912, 376-777, 424-750, 748-807, 778-912, and 808-912 of SEQ ID NO:1, or the complementary strand thereto, or the cDNA contained in the deposited clone.

More generally, by a fragment of an isolated nucleic acid molecule having the nucleotide sequence of the deposited cDNA or the nucleotide sequence shown in FIGS. 1A, 1B, and 1C (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A, 1B, and 1C (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A, 1B, and 1C (SEQ ID NO:1). Preferred nucleic acid fragments of the present invention include nucleic acid molecules encoding epitope-bearing portions of the t-PALP polypeptide as identified in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 209023. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 micrograms/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 35, 40, 45, 50, 55, 60, 65) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A, 1B, and 1C (SEQ ID NO:1)). Of course, a polynucleotide which hybridizes only to a poly A sequence (such as the 3' terminal poly(A) tract of the t-PALP cDNA shown in FIGS. 1A, 1B, and 1C (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a t-PALP polypeptide may include, but are not limited to those encoding the amino acid sequence of the predicted kringle domain, by itself, the amino acid sequence of the predicted protease domain, by itself, the amino acid sequence of the mature polypeptide, by itself; and the coding sequence for the mature polypeptide and additional sequences, such as those encoding the about 21 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the t-PALP fused to Fc at the N- or C-terminus.

In a preferred embodiment, the expression vectors pCMVFLAG5a or pFLAG-CMV-1 (available from Sigma, St. Louis, Mo., USA) are used for the expression of t-PALP-FLAG fusion proteins of the invention. See, Andersson, S., et al., *J. Biol. Chem.* 264:8222–29 (1989); Thomsen, D. R., et al., *Proc. Natl. Acad. Sci. USA,* 81:659–63 (1984); and Kozak, M., *Nature* 308:241 (1984) (each of which is hereby incorporated by reference). In this embodiment, t-PALP polynucleotides of the invention are fused to a polynucleotide encoding a "FLAG" polypeptide. Thus, a t-PALP- FLAG fusion protein is encompassed by the present invention. The FLAG antigenic polypeptide may be fused to a t-PALP polypeptide of the invention at either or both the amino- and carboxy-termini of the t-PALP protein. In further preferred embodiments, a t-PALP-FLAG fusion protein is detectable by anti-FLAG monoclonal antibodies (also available from Sigma).

In a further preferred embodiment, the FLAG polypeptide sequence is fused to the amino-terminus of amino acid residues Ser-22 through Ala-263 of the t-PALP amino acid sequence shown in FIGS. 1A, 1B, and 1C (which is identical to residues Ser-1 through Ala-242 of SEQ ID NO:2). This fusion protein is expressed from the pFLAG-CMV-1 expression vector and is designated pFLAGCMV-1:t-PALP.S22-A263. This FLAG-t-PALP expression construct will allow purification of t-PALP protein from the supernatants of transiently transfected cell cultures by virtue of the amino-terminal FLAG tag. Moreover, any carboxy-terminal processing of t-PALP may also be detected and analyzed using this expression construct.

In an additional preferred embodiment, the FLAG polypeptide sequence is fused to the carboxy-terminus of amino acid residues Met-1 through Asp-165 of the t-PALP amino acid sequence shown in FIGS. 1A, 1B, and 1C (which is identical to residues Met-(−21) through Asp-144 of SEQ ID NO:2). This fusion protein is expressed from the pFLAG-CMV-5a expression vector and is designated pFLAGCMV-5a:t-PALP.M1-D165. This FLAG-t-PALP expression construct will allow purification of t-PALP protein from the supernatants of transiently transfected cell cultures by virtue of the amino-terminal FLAG tag. Moreover, use of this expression construct will allow a determination of the predicted processed form of t-PALP by isolation via the FLAG tag and subsequent C-terminal peptide sequencing. Also, use of this expression construct will enable an analysis of biological and/or structural activities of a predicted processed form of t-PALP (i.e., amino acid residues 1–144 of SEQ ID NO:2).

Variant and Mutant Polynucleotides

The present invention further relates to variants of the nucleic acid molecules of the present invention, which encode portions, analogs or derivatives of the t-PALP protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the t-PALP protein or portions thereof. Also especially preferred in this regard are conservative substitutions. For example, conservative amino acid substitutions of t-PALP can be made by site directed changes which replace a particular amino acid with a conservative amino acid. Preferred conservative substitutions include: M1 replaced with A, G, I, L, S, T, or V; L2 replaced with A, G, I, S, T, M, or V; L3 replaced with A, G, I, S, T, M, or V; A4 replaced with G, I, L, S, T, M, or V; W5 replaced with F, or Y; V6 replaced with A, G, I, L, S, T, or M; Q7 replaced with N; A8 replaced with G, I, L, S, T, M, or V; F9 replaced with W, or Y; L10 replaced with A, G, I, S, T, M, or V; V11 replaced with A, G, I, L, S, T, or M; S12 replaced with A, G, I, L, T, M, or V; N13 replaced with Q; M14 replaced with A, G, I, L, S, T, or V; L15 replaced with A, G, I, S, T, M, or V; L16 replaced with A, G, I, S, T, M, or V; A17 replaced with G, I, L, S, T, M, or V; E18 replaced with D; A19 replaced with G, I, L, S, T, M, or V; Y20 replaced with F, or W; G21 replaced with A, I, L, S, T, M, or V; S22 replaced with A, G, I, L, T, M, or V; G23 replaced with A, I, L, S, T, M, or V; G24 replaced with A, I, L, S, T, M, or V; F26 replaced with W, or Y; W27 replaced with F, or Y; D28 replaced with E; N29 replaced with Q; G30 replaced with A, I, L, S, T, M, or V; H31 replaced with K, or R; L32 replaced with A, G, I, S, T, M, or V; Y33 replaced with F, or W; R34 replaced with H, or K; E35 replaced with D; D36 replaced with E; Q37 replaced with N; T38 replaced with A, G, I, L, S, M, or V; S39 replaced with A, G, I, L, T, M, or V; A41 replaced with G, I, L, S, T, M, or V; G43 replaced with A, I, L, S, T, M, or V; L44 replaced with A, G, I, S, T, M, or V; R45 replaced with H, or K; L47 replaced with A, G, I, S, T, M, or V; N48 replaced with Q; W49 replaced with F, or Y; L50 replaced with A, G, I, S, T, M, or V; D51 replaced with E; A52 replaced with G, I, L, S, T, M, or V; Q53 replaced with N; S54 replaced with A, G, I, L, T, M, or V; G55 replaced with A, I, L, S, T, M, or V; L56 replaced with A, G, I, S, T, M, or V; A57 replaced with G, I, L, S, T, M, or V; S58 replaced with A, G, I, L, T, M, or V; A59 replaced with G, I, L, S, T, M, or V; V61 replaced with A, G, I, L, S, T, or M; S62 replaced with A, G, I, L, T, M, or V; G63 replaced with A, I, L, S, T, M, or V; A64 replaced with G, I, L, S, T, M, or V; G65 replaced with A, I, L, S, T, M, or V; N66 replaced with Q; H67 replaced with K, or R; S68 replaced with A, G, I, L, T, M, or V; Y69 replaced with F, or W; R71 replaced with H, or K; N72 replaced with Q; D74 replaced with E; E75 replaced with D; D76 replaced with E; R78 replaced with H, or K; G79 replaced with A, I, L, S, T, M, or V; W81 replaced with F, or Y; Y83 replaced with F, or W; V84 replaced with A, G, I, L, S, T, or M; S85 replaced with A, G, I, L, T, M, or V; G86 replaced with A, I, L, S, T, M, or V; E87 replaced with D; A88 replaced with G, I, L, S, T, M, or V; G89 replaced with A, I, L, S, T, M, or V; V90 replaced with A, G, I, L, S, T, or M; E92 replaced with D; K93 replaced with H, or R; R94 replaced with H, or K; E97 replaced with D; D98 replaced with E; L99 replaced with A, G, I, S, T, M, or V; R100 replaced with H, or K; E103 replaced with D; T104 replaced with A, G, I, L, S, M, or V; T105 replaced with A, G, I, L, S, M, or V; S106 replaced with A, G, I, L, T, M, or V; Q107 replaced with N; A108 replaced with G, I, L, S, T, M, or V; L109 replaced with A, G, I, S, T, M, or V; A111 replaced with G, I, L, S, T, M, or V; F112 replaced with W, or Y; T113 replaced with A, G, I, L, S, M, or V; T114 replaced with A, G, I, L, S, M, or V; E115 replaced with D; I116 replaced with A, G, L, S, T, M, or V; Q117 replaced with N; E118 replaced with D; A119 replaced with G, I, L, S, T, M, or V; S120 replaced with A, G, I, L, T, M, or V; E121 replaced with D; G122 replaced with A, I, L, S, T, M, or V; G124 replaced with A, I, L, S, T, M, or V; A125 replaced with G, I, L, S, T, M, or V; D126 replaced with E; E127 replaced with D; V128 replaced with A, G, I, L, S, T, or M; Q129 replaced with N; V130 replaced with A, G, I, L, S, T, or M; F131 replaced with W, or Y; A132 replaced with G, I, L, S, T, M, or V; A134 replaced with G, I, L, S, T, M, or V; N135 replaced with Q; A136 replaced with G, I, L, S, T, M, or V; L137 replaced with A, G, I, S, T, M, or V; A139 replaced with G, I, L, S, T, M, or V; R140 replaced with H, or K; S141 replaced with A, G, I, L, T, M, or V; E142 replaced with D; A143 replaced with G, I, L, S, T, M, or V; A144 replaced with G, I, L, S, T, M, or V; A145 replaced with G, I, L, S, T, M, or V; V146 replaced with A, G, I, L, S, T, or M; Q147 replaced with N; V149 replaced with A, G, I, L, S, T, or M; I150 replaced with A, G, L, S, T, M, or V; G151 replaced with A, I, L, S, T, M, or V; I152 replaced with A, G, L, S, T, M, or V; S153 replaced with A, G, I, L, T, M, or V; Q154 replaced with N; R155 replaced with H, or K; V156 replaced with A, G, I, L, S, T, or M; R157 replaced with H, or K; M158 replaced with A, G, I, L, S, T, or V; N159 replaced with Q; S160 replaced with A, G, I, L, T, M, or V; K161 replaced with H, or R; E162 replaced with D; K163 replaced with H, or R; K164 replaced with H, or R; D165 replaced with E; L166 replaced with A, G, I, S, T, M, or V; G167 replaced with A, I, L, S, T, M, or V; T168 replaced with A, G, I, L, S, M, or V; L169 replaced with A, G, I, S, T, M, or V; G170 replaced with A, I, L, S, T, M, or V; Y171 replaced with F, or W; V172 replaced with A, G, I, L, S, T, or M; L173 replaced with A, G, I, S, T, M, or V; G174 replaced with A, I, L, S, T, M, or V; I175 replaced with A, G, L, S, T, M, or V; T176 replaced with A, G, I, L, S, M, or V; M177 replaced with A, G, I, L, S, T, or V; M178 replaced with A, G, I, L, S, T, or V; V179 replaced with A, G, I, L, S, T, or M; I180 replaced with A, G, L, S, T, M, or V; I181 replaced with A, G, L, S, T, M, or V; I182 replaced with A, G, L, S, T, M, or V; A183 replaced with G, I, L, S, T, M, or V; I184 replaced with A, G, L, S, T, M, or V; G185 replaced with A, I, L, S, T, M, or V; A186 replaced with G, I, L, S, T, M, or V; G187 replaced with A, I, L, S, T, M, or V; I188 replaced with A, G, L, S, T, M, or V; I189 replaced with A, G, L, S, T, M, or V; L190 replaced with A, G, I, S, T, M, or V; G191 replaced with A, I, L, S, T, M, or V; Y192 replaced with F, or W; S193 replaced with A, G, I, L, T, M, or V; Y194 replaced with F, or W; K195 replaced with H, or R; R196 replaced with H, or K; G197 replaced with A, I, L, S, T, M, or V; K198 replaced with H, or R; D199 replaced with E; L200 replaced with A, G, I, S, T, M, or V; K201 replaced with H, or R; E202 replaced with D; Q203 replaced with N; H204 replaced with K, or R; D205 replaced with E; Q206 replaced with N; K207 replaced with H, or R; V208 replaced with A, G, I, L, S, T, or M; E210 replaced with D; R211 replaced with H, or K; E212 replaced with D; M213 replaced with A, G, I, L, S, T, or V; Q214 replaced with N; R215 replaced with H, or K; I216 replaced with A, G, L, S, T, M, or V; T217 replaced with A, G, I, L, S, M, or V; L218 replaced with A, G, I, S, T, M, or V; L220 replaced with A, G, I, S, T, M, or V; S221 replaced with A, G, I, L, T, M, or V; A222 replaced with G, I, L, S, T, M, or V; F223 replaced with W, or Y; T224 replaced with A, G, I, L, S, M, or V; N225 replaced with Q; T227 replaced with A, G, I, L, S, M, or V; E229 replaced with D; I230 replaced with A, G, L, S, T, M, or V; V231 replaced with A, G, I, L, S, T, or M; D232 replaced with E; E233 replaced with D; K234 replaced with H, or R; T235 replaced with A, G, I, L, S, M, or V; V236 replaced with A, G, I, L, S, T, or M; V237 replaced with A, G, I, L, S, T, or M; V238 replaced with A, G, I, L, S, T, or M; H239 replaced with K, or R; T240 replaced with A, G, I, L, S, M, or V; S241 replaced with A, G, I, L, T, M, or V; Q242 replaced with N; T243 replaced with A, G, I, L, S, M, or V; V245 replaced with A, G, I, L, S, T, or M; D246 replaced with E; Q248 replaced with N; E249 replaced with D; G250 replaced with A, I, L, S, T, M, or V; S251 replaced with A, G, I, L, T, M, or V; T252 replaced with A, G, I, L, S, M, or V; L254 replaced with A, G, I, S, T, M, or V; M255 replaced with A, G, I, L, S, T, or V; G256 replaced with A, I, L, S, T, M, or V; Q257 replaced with N; A258 replaced with G, I, L, S, T, M, or V; G259 replaced with A, I, L, S, T, M, or V; T260 replaced with A, G, I, L, S, M, or V; G262 replaced with A, I, L, S, T, M, or V; or A263 replaced with G, I, L, S, T, M, or V.

The resulting constructs can be routinely screened for activities or functions described throughout the specification and known in the art. Preferably, the resulting constructs have an increased t-PALP activity or function (including dominant negative activities or functions), while the remaining t-PALP activities or functions are maintained. More preferably, the resulting constructs have more than one increased t-PALP activity or function (including dominant negative activities or functions), while the remaining t-PALP activities or functions are maintained.

Besides conservative amino acid substitution, variants of t-PALP include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, t-PALP polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

For example, preferred non-conservative substitutions of t-PALP include: M1 replaced with D, E, H, K, R, N, Q, F, W, Y, P, or C; L2 replaced with D, E, H, K, R, N, Q, F, W, Y, P, or C; L3 replaced with D, E, H, K, R, N, Q, F, W, Y, P, or C; A4 replaced with D, E, H, K, R, N, Q, F, W, Y, P, or C; W5 replaced with D, E, H, K, R, N, Q, A, G, I, L, S, T, M, V, P, or C; V6 replaced with D, E, H, K, R, N, Q, F, W, Y, P, or C; Q7 replaced with D, E, H, K, R, A, G, I, L, S, T, M, V, F, W, Y, P, or C; A8 replaced with D, E, H, K, R, N, Q, F, W, Y, P, or C; F9 replaced with D, E, H, K, R, N, Q, A, G, I, L, S, T, M, V, P, or C; L10 replaced with D, E, H, K, R, N, Q, F, W, Y, P, or C; V11 replaced with D, E, H, K, R, N, Q, F, W, Y, P, or C; S12 replaced with D, E, H, K, R, N, Q, F, W, Y, P, or C; N13 replaced with D, E, H, K, R, A, G, I, L, S, T, M, V, F, W, Y, P, or C; M14 replaced with D, E, H, K, R, N, Q, F, W, Y, P, or C; L15 replaced with D, E, H, K, R, N, Q, F, W, Y, P, or C; L16 replaced with D, E, H, K, R, N, Q, F, W, Y, P, or C; A17 replaced with D, E, H, K, R, N, Q, F, W, Y, P, or C; E18 replaced with H, K, R, A, G, I, L, S, T, M, V, N, Q, F, W, Y, P, or C; A19 replaced with D, E, H, K, R, N, Q, F, W, Y, P, or C; Y20 replaced with D, E, H, K, R, N, Q, A, G, I, L, S, T, M, V, P, or C; G21 replaced with D, E, H, K, R, N, Q, F, W, Y, P, or C; S22 replaced with D, E, H, K, R, N, Q, F, W, Y, P, or C; G23 replaced with D, E, H, K, R, N, Q, F, W, Y, P, or C; G24 replaced with D, E, H, K, R, N, Q, F, W, Y, P, or C; C25 replaced with D, E, H, K, R, A, G, I, L, S, T, M, V, N, Q, F, W, Y, or P; F26 replaced with D, E, H, K, R, N, Q, A, G, I, L, S, T, M, V, P, or C; W27 replaced with D, E, H, K, R, N, Q, A, G, I, L, S, T, M, V, P, or C; D28 replaced with H, K, R, A, G, I, L, S, T, M, V, N, Q, F, W, Y, P, or C; N29 replaced with D, E, H, K, R, A, G, I, L, S, T, M, V, F, W, Y, P, or C; G30 replaced with D, E, H, K, R, N, Q, F, W, Y, P, or C; H31 replaced with D, E, A, G, I, L, S, T, M, V, N, Q, F, W, Y, P, or C; L32 replaced with D, E, H, K, R, N, Q, F, W, Y, P, or C; Y33 replaced with D, E, H, K, R, N, Q, A, G, I, L, S, T, M, V, P, or C; R34 replaced with D, E, A, G, I, L, S, T, M, V, N, Q, F, W, Y, P, or C; E35 replaced with H, K, R, A, G, I, L, S, T, M, V, N, Q, F, W, Y, P, or C; D36 replaced with H, K, R, A, G, I, L, S, T, M, V, N, Q, F, W, Y, P, or C; Q37 replaced with D, E, H, K, R, A, G, I, L, S, T, M, V, F, W, Y, P, or C; T38 replaced with D, E, H, K, R, N, Q, F, W, Y, P, or C; S39 replaced with D, E, H, K, R, N, Q, F, W, Y, P, or C; P40 replaced with D, E, H, K, R, A, G, I, L, S, T, M, V, N, Q, F, W, Y, or C; A41 replaced with D, E, H, K, R, N, Q, F, W, Y, P, or C; P42 replaced with D, E, H, K, R, A, G, I, L, S, T, M, V, N, Q, F, W, Y, or C; G43 replaced with D, E, H, K, R, N, Q, F, W, Y, P, or C; L44 replaced with D, E, H, K, R, N, Q, F, W, Y, P, or C; R45 replaced with D, E, A, G, I, L, S, T, M, V, N, Q, F, W, Y, P, or C; C46 replaced with D, E, H, K, R, A, G, I, L, S, T, M, V, N, Q, F, W, Y, or P; L47 replaced with D, E, H, K, R, N, Q, F, W, Y, P, or C; N48 replaced with D, E, H, K, R, A, G, I, L, S, T, M, V, F, W, Y, P, or C; W49 replaced with D, E, H, K, R, N, Q, A, G, I, L, S, T, M, V, P, or C; L50 replaced with D, E, H, K, R, N, Q, F, W, Y, P, or C; D51 replaced with H, K, R, A, G, I, L, S, T, M, V, N, Q, F, W, Y, P, or C; A52 replaced with D, E, H, K, R, N, Q, F, W, Y, P, or C; Q53 replaced with D, E, H, K, R, A, G, I, L, S, T, M, V, F, W, Y, P, or C; S54 replaced with D, E, H, K, R, N, Q, F, W, Y, P, or C; G55 replaced with D, E, H, K, R, N, Q, F, W, Y, P, or C; L56 replaced with D, E, H, K, R, N, Q, F, W, Y, P, or C; A57 replaced with D, E, H, K, R, N, Q, F, W, Y, P, or C; S58 replaced with D, E, H, K, R, N, Q, F, W, Y, P, or C; A59 replaced with D, E, H, K, R, N, Q, F, W, Y, P, or C; P60 replaced with D, E, H, K, R, A, G, I, L, S, T, M, V, N, Q, F, W, Y, or C; V61 replaced with D, E, H, K, R, N, Q, F, W, Y, P, or C; S62 replaced with D, E, H, K, R, N, Q, F, W, Y, P, or C; G63 replaced with D, E, H, K, R, N, Q, F, W, Y, P, or C; A64 replaced with D, E, H, K, R, N, Q, F, W, Y, P, or C; G65 replaced with D, E, H, K, R, N, Q, F, W, Y, P, or C; N66 replaced with D, E, H, K, R, A, G, I, L, S, T, M, V, F, W, Y, P, or C; H67 replaced with D, E, A, G, I, L, S, T, M, V, N, Q, F, W, Y, P, or C; S68 replaced with D, E, H, K, R, N, Q, F, W, Y, P, or C; Y69 replaced with D, E, H, K, R, N, Q, A, G, I, L, S, T, M, V, P, or C; C70 replaced with D, E, H, K, R, A, G, I, L, S, T, M, V, N, Q, F, W, Y, or P; R71 replaced with D, E, A, G, I, L, S, T, M, V, N, Q, F, W, Y, P, or C; N72 replaced with D, E, H, K, R, A, G, I, L, S, T, M, V, F, W, Y, P, or C; P73 replaced with D, E, H, K, R, A, G, I, L, S, T, M, V, N, Q, F, W, Y, or C; D74 replaced with H, K, R, A, G, I, L, S, T, M, V, N, Q, F, W, Y, P, or C; E75 replaced with H, K, R, A, G, I, L, S, T, M, V, N, Q, F, W, Y, P, or C; D76 replaced with H, K, R, A, G, I, L, S, T, M, V, N, Q, F, W, Y, P, or C; P77 replaced with D, E, H, K, R, A, G, I, L, S, T, M, V, N, Q, F, W, Y, or C; R78 replaced with D, E, A, G, I, L, S, T, M, V, N, Q, F, W, Y, P, or C; G79 replaced with D, E, H, K, R, N, Q, F, W, Y, P, or C; P80 replaced with D, E, H, K, R, A, G, I, L, S, T, M, V, N, Q, F, W, Y, or C; W81 replaced with D, E, H, K, R, N, Q, A, G, I, L, S, T, M, V, P, or C; C82 replaced with D, E, H, K, R, A, G, I, L, S, T, M, V, N, Q, F, W, Y, or P; Y83 replaced with D, E, H, K, R, N, Q, A, G, I, L, S, T, M, V, P, or C; V84 replaced with D, E, H, K, R, N, Q, F, W, Y, P, or C; S85 replaced with D, E, H, K, R, N, Q, F, W, Y, P, or C; G86 replaced with D, E, H, K, R, N, Q, F, W, Y, P, or C; E87 replaced with H, K, R, A, G, I, L, S, T, M, V, N, Q, F, W, Y, P, or C; A88 replaced with D, E, H, K, R, N, Q, F, W, Y, P, or C; G89 replaced with D, E, H, K, R, N, Q, F, W, Y, P, or C; V90 replaced with D, E, H, K, R, N, Q, F, W, Y, P, or C; P91 replaced with D, E, H, K, R, A, G, I, L, S, T, M, V, N, Q, F, W, Y, or C; E92 replaced with H, K, R, A, G, I, L, S, T, M, V, N, Q, F, W, Y, P, or C; K93 replaced with D, E, A, G, I, L, S, T, M, V, N, Q, F, W, Y, P, or C; R94 replaced with D, E, A, G, I, L, S, T, M, V, N, Q, F, W, Y, P, or C; P95 replaced with D, E, H, K, R, A, G, I, L, S, T, M, V, N, Q, F, W, Y, or C; C96 replaced with D, E, H, K, R, A, G, I, L, S, T, M, V, N, Q, F, W, Y, or P; E97 replaced with H, K, R, A, G, I, L, S, T, M, V, N, Q, F, W, Y, P, or C; D98 replaced with H, K, R, A, G, I, L, S, T, M, V, N, Q, F, W, Y, P, or C; L99 replaced with D, E, H, K, R, N, Q, F, W, Y, P, or C; R100 replaced with D, E, A, G, I, L, S, T, M, V, N, Q, F, W, Y, P, or C; C101 replaced with D, E, H, K, R, A, G, I, L, S, T, M, V, N, Q, F, W, Y, or P; P102 replaced with D, E, H, K, R, A, G, I, L, S, T, M, V, N, Q, F, W, Y, or C; E103 replaced with H, K, R, A, G, I, L, S, T, M, V, N, Q, F, W, Y, P, or C; T104 replaced with D, E, H, K, R, N, Q, F, W, Y, P, or C; T105 replaced with D, E, H, K, R, N, Q, F, W, Y, P, or C; S106 replaced with D, E, H, K, R, N, Q, F, W, Y, P, or C; Q107 replaced with D, E, H, K, R, A, G, I, L, S, T, M, V, F, W, Y, P, or C; A108 replaced with D, E, H, K, R, N, Q, F, W, Y, P, or C; L109 replaced with D, E, H, K, R, N, Q, F, W, Y, P, or C; P110 replaced with D, E, H, K, R, A, G, I, L, S, T, M, V, N, Q, F, W, Y, or C; A111 replaced with D, E, H, K, R, N, Q, F, W, Y, P, or C; F112 replaced with D, E, H, K, R, N, Q, A, G, I, L, S, T, M, V, P, or C; T113 replaced with D, E, H, K, R, N, Q, F, W, Y, P, or C; T114 replaced with D, E, H, K, R, N, Q, F, W, Y, P, or C; E115 replaced with H, K, R, A, G, I, L, S, T, M, V, N, Q, F, W, Y, P, or C; I116 replaced with D, E, H, K, R, N, Q, F, W, Y, P, or C; Q117 replaced with D, E, H, K, R, A, G, I, L, S, T, M, V, F, W, Y, P, or C; E118 replaced with H, K, R, A, G, I, L, S, T, M, V, N, Q, F, W, Y, P, or C; A119 replaced with D, E, H, K, R, N, Q, F, W, Y, P, or C; S120 replaced with D, E, H, K, R, N, Q, F, W, Y, P, or C; E121 replaced with H, K, R, A, G, I, L, S, T, M, V, N, Q, F, W, Y, P, or C; G122 replaced with D, E, H, K, R, N, Q, F, W, Y, P, or C; P123 replaced with D, E, H, K, R, A, G, I, L, S, T, M, V, N, Q, F, W, Y, or C; G124 replaced with D, E, H, K, R, N, Q, F, W, Y, P, or C; A125 replaced with D, E, H, K, R, N, Q, F, W, Y, P, or C; D126 replaced with H, K, R, A, G, I, L, S, T, M, V, N, Q, F, W, Y, P, or C; E127 replaced with H, K, R, A, G, I, L, S, T, M, V, N, Q, F, W, Y, P, or C; V128 replaced with D, E, H, K, R, N, Q, F, W, Y, P, or C; Q129 replaced with D, E, H, K, R, A, G, I, L, S, T, M, V, F, W, Y, P, or C; V130 replaced with D, E, H, K, R, N, Q, F, W, Y, P, or C; F131 replaced with D, E, H, K, R, N, Q, A, G, I, L, S, T, M, V, P, or C; A132 replaced with D, E, H, K, R, N, Q, F, W, Y, P, or C; P133 replaced with D, E, H, K, R, A, G, I, L, S, T, M, V, N, Q, F, W, Y, or C; A134 replaced with D, E, H, K, R, N, Q, F, W, Y, P, or C; N135 replaced with D, E, H, K, R, A, G, I, L, S, T, M, V, F, W, Y, P, or C; A136 replaced with D, E, H, K, R, N, Q, F, W, Y, P, or C; L137 replaced with D, E, H, K, R, N, Q, F, W, Y, P, or C; P138 replaced with D, E, H, K, R, A, G, I, L, S, T, M, V, N, Q, F, W, Y, or C; A139 replaced with D, E, H, K, R, N, Q, F, W, Y, P, or C; R140 replaced with D, E, A, G, I, L, S, T, M, V, N, Q, F, W, Y, P, or C; S141 replaced with D, E, H, K, R, N, Q, F, W, Y, P, or C; E142 replaced with H, K, R, A, G, I, L, S, T, M, V, N, Q, F, W, Y, P, or C; A143 replaced with D, E, H, K, R, N, Q, F, W, Y, P, or C; A144 replaced with D, E, H, K, R, N, Q, F, W, Y, P, or C; A145 replaced with D, E, H, K, R, N, Q, F, W, Y, P, or C; V146 replaced with D, E, H, K, R, N, Q, F, W, Y, P, or C; Q147 replaced with D, E, H, K, R, A, G, I, L, S, T, M, V, F, W, Y, P, or C; P148 replaced with D, E, H, K, R, A, G, I, L, S, T, M, V, N, Q, F, W, Y, or C; V149 replaced with D, E, H, K, R, N, Q, F, W, Y, P, or C; I150 replaced with D, E, H, K, R, N, Q, F, W, Y, P, or C; G151 replaced with D, E, H, K, R, N, Q, F, W, Y, P, or C; I152 replaced with D, E, H, K, R, N, Q, F, W, Y, P, or C; S153 replaced with D, E, H, K, R, N, Q, F, W, Y, P, or C; Q154 replaced with D, E, H, K, R, A, G, I, L, S, T, M, V, F, W, Y, P, or C; R155 replaced with D, E, A, G, I, L, S, T, M, V, N, Q, F, W, Y, P, or C; V156 replaced with D, E, H, K, R, N, Q, F, W, Y, P, or C; R157 replaced with D, E, A, G, I, L, S, T, M, V, N, Q, F, W, Y, P, or C; M158 replaced with D, E, H, K, R, N, Q, F, W, Y, P, or C; N159 replaced with D, E, H, K, R, A, G, I, L, S, T, M, V, F, W, Y, P, or C; S160 replaced with D, E, H, K, R, N, Q, F, W, Y, P, or C; K161 replaced with D, E, A, G, I, L, S, T, M, V, N, Q, F, W, Y, P, or C; E162 replaced with H, K, R, A, G, I, L, S, T, M, V, N, Q, F, W, Y, P, or C; K163 replaced with D, E, A, G, I, L, S, T, M, V, N, Q, F, W, Y, P, or C; K164 replaced with D, E, A, G, I, L, S, T, M, V, N, Q, F, W, Y, P, or C; D165 replaced with H, K, R, A, G, I, L, S, T, M, V, N, Q, F, W, Y, P, or C; L166 replaced with D, E, H, K, R, N, Q, F, W, Y, P, or C; G167 replaced with D, E, H, K, R, N, Q, F, W, Y, P, or C; T168 replaced with D, E, H, K, R, N, Q, F, W, Y, P, or C; L169 replaced with D, E, H, K, R, N, Q, F, W, Y, P, or C; G170 replaced with D, E, H, K, R, N, Q, F, W, Y, P, or C; Y171 replaced with D, E, H, K, R, N, Q, A, G, I, L, S, T, M, V, P, or C; V172 replaced with D, E, H, K, R, N, Q, F, W, Y, P, or C; L173 replaced with D, E, H, K, R, N, Q, F, W, Y, P, or C; G174 replaced with D, E, H, K, R, N, Q, F, W, Y, P, or C; I175 replaced with D, E, H, K, R, N, Q, F, W, Y, P, or C; T176 replaced with D, E, H, K, R, N, Q, F, W, Y, P, or C; M177 replaced with D, E, H, K, R, N, Q, F, W, Y, P, or C; M178 replaced with D, E, H, K, R, N, Q, F, W, Y, P, or C; V179 replaced with D, E, H, K, R, N, Q, F, W, Y, P, or C; I180 replaced with D, E, H, K, R, N, Q, F, W, Y, P, or C; I181 replaced with D, E, H, K, R, N, Q, F, W, Y, P, or C; I182 replaced with D, E, H, K, R, N, Q, F, W, Y, P, or C; A183 replaced with D, E, H, K, R, N, Q, F, W, Y, P, or C; I184 replaced with D, E, H, K, R, N, Q, F, W, Y, P, or C; G185 replaced with D, E, H, K, R, N, Q, F, W, Y, P, or C; A186 replaced with D, E, H, K, R, N, Q, F, W, Y, P, or C; G187 replaced with D, E, H, K, R, N, Q, F, W, Y, P, or C; I188 replaced with D, E, H, K, R, N, Q, F, W, Y, P, or C; I189 replaced with D, E, H, K, R, N, Q, F, W, Y, P, or C; L190 replaced with D, E, H, K, R, N, Q, F, W, Y, P, or C; G191 replaced with D, E, H, K, R, N, Q, F, W, Y, P, or C; Y192 replaced with D, E, H, K, R, N, Q, A, G, I, L, S, T, M, V, P, or C; S193 replaced with D, E, H, K, R, N, Q, F, W, Y, P, or C; Y194 replaced with D, E, H, K, R, N, Q, A, G, I, L, S, T, M, V, P, or C; K195 replaced with D, E, A, G, I, L, S, T, M, V, N, Q, F, W, Y, P, or C; R196 replaced with D, E, A, G, I, L, S, T, M, V, N, Q, F, W, Y, P, or C; G197 replaced with D, E, H, K, R, N, Q, F, W, Y, P, or C; K198 replaced with D, E, A, G, I, L, S, T, M, V, N, Q, F, W, Y, P, or C; D199 replaced with H, K, R, A, G, I, L, S, T, M, V, N, Q, F, W, Y, P, or C; L200 replaced with D, E, H, K, R, N, Q, F, W, Y, P, or C; K201 replaced with D, E, A, G, I, L, S, T, M, V, N, Q, F, W, Y, P, or C; E202 replaced with H, K, R, A, G, I, L, S, T, M, V, N, Q, F, W, Y, P, or C; Q203 replaced with D, E, H, K, R, A, G, I, L, S, T, M, V, F, W, Y, P, or C; H204 replaced with D, E, A, G, I, L, S, T, M, V, N, Q, F, W, Y, P, or C; D205 replaced with H, K, R, A, G, I, L, S, T, M, V, N, Q, F, W, Y, P, or C; Q206 replaced with D, E, H, K, R, A, G, I, L, S, T, M, V, F, W, Y, P, or C; K207 replaced with D, E, A, G, I, L, S, T, M, V, N, Q, F, W, Y, P, or C; V208 replaced with D, E, H, K, R, N, Q, F, W, Y, P, or C; C209 replaced with D, E, H, K, R, A, G, I, L, S, T, M, V, N, Q, F, W, Y, or P; E210 replaced with H, K, R, A, G, I, L, S, T, M, V, N, Q, F, W, Y, P, or C; R211 replaced with D, E, A, G, I, L, S, T, M, V, N, Q, F, W, Y, P, or C; E212 replaced with H, K, R, A, G, I, L, S, T, M, V, N, Q, F, W, Y, P, or C; M213 replaced with D, E, H, K, R, N, Q, F, W, Y, P, or C; Q214 replaced with D, E, H, K, R, A, G, I, L, S, T, M, V, F, W, Y, P, or C; R215 replaced with D, E, A, G, I, L, S, T, M, V, N, Q, F, W, Y, P, or C; I216 replaced with D, E, H, K, R, N, Q, F, W, Y, P, or C; T217 replaced with D, E, H, K, R, N, Q, F, W, Y, P, or C; L218 replaced with D, E, H, K, R, N, Q, F, W, Y, P, or C; P219 replaced with D, E, H, K, R, A, G, I, L, S, T, M, V, N, Q, F, W, Y, or C; L220 replaced with D, E, H, K, R, N, Q, F, W, Y, P, or C; S221 replaced with D, E, H, K, R, N, Q, F, W, Y, P, or C; A222 replaced with D, E, H, K, R, N, Q, F, W, Y, P, or C; F223 replaced with D, E, H, K, R, N, Q, A, G, I, L, S, T, M, V, P, or C; T224 replaced with D, E, H, K, R, N, Q, F, W, Y, P, or C; N225 replaced with D, E, H, K, R, A, G, I, L, S, T, M, V, F, W, Y, P, or C; P226 replaced with D, E, H, K, R, A, G, I, L, S, T, M, V, N, Q, F, W, Y, or C; T227 replaced with D, E, H, K, R, N, Q, F, W, Y, P, or C; C228 replaced with D, E, H, K, R, A, G, I, L, S, T, M, V, N, Q, F, W, Y, or P; E229 replaced with H, K, R, A, G, I, L, S, T, M, V, N, Q, F, W, Y, P, or C; I230 replaced with D, E, H, K, R, N, Q, F, W, Y, P, or C; V231 replaced with D, E, H, K, R, N, Q, F, W, Y, P, or C; D232 replaced with H, K, R, A, G, I, L, S, T, M, V, N, Q, F, W, Y, P, or C; E233 replaced with H, K, R, A, G, I, L, S, T, M, V, N, Q, F, W, Y, P, or C; K234 replaced with D, E, A, G, I, L, S, T, M, V, N, Q, F, W, Y, P, or C; T235 replaced with D, E, H, K, R, N, Q, F, W, Y, P, or C; V236 replaced with D, E, H, K, R, N, Q, F, W, Y, P, or C; V237 replaced with D, E, H, K, R, N, Q, F, W, Y, P, or C; V238 replaced with D, E, H, K, R, N, Q, F, W, Y, P, or C; H239 replaced with D, E, A, G, I, L, S, T, M, V, N, Q, F, W, Y, P, or C; T240 replaced with D, E, H, K, R, N, Q, F, W, Y, P, or C; S241 replaced with D, E, H, K, R, N, Q, F, W, Y, P, or C; Q242 replaced with D, E, H, K, R, A, G, I, L, S, T, M, V, F, W, Y, P, or C; T243 replaced with D, E, H, K, R, N, Q, F, W, Y, P, or C; P244 replaced with D, E, H, K, R, A, G, I, L, S, T, M, V, N, Q, F, W, Y, or C; V245 replaced with D, E, H, K, R, N, Q, F, W, Y, P, or C; D246 replaced with H, K, R, A, G, I, L, S, T, M, V, N, Q, F, W, Y, P, or C; P247 replaced with D, E, H, K, R, A, G, I, L, S, T, M, V, N, Q, F, W, Y, or C; Q248 replaced with D, E, H, K, R, A, G, I, L, S, T, M, V, F, W, Y, P, or C; E249 replaced with H, K, R, A, G, I, L, S, T, M, V, N, Q, F, W, Y, P, or C; G250 replaced with D, E, H, K, R, N, Q, F, W, Y, P, or C; S251 replaced with D, E, H, K, R, N, Q, F, W, Y, P, or C; T252 replaced with D, E, H, K, R, N, Q, F, W, Y, P, or C; P253 replaced with D, E, H, K, R, A, G, I, L, S, T, M, V, N, Q, F, W, Y, or C; L254 replaced with D, E, H, K, R, N, Q, F, W, Y, P, or C; M255 replaced with D, E, H, K, R, N, Q, F, W, Y, P, or C; G256 replaced with D, E, H, K, R, N, Q, F, W, Y, P, or C; Q257 replaced with D, E, H, K, R, A, G, I, L, S, T, M, V, F, W, Y, P, or C; A258 replaced with D, E, H, K, R, N, Q, F, W, Y, P, or C; G259 replaced with D, E, H, K, R, N, Q, F, W, Y, P, or C; T260 replaced with D, E, H, K, R, N, Q, F, W, Y, P, or C; P261 replaced with D, E, H, K, R, A, G, I, L, S, T, M, V, N, Q, F, W, Y, or C; G262 replaced with D, E, H, K, R, N, Q, F, W, Y, P, or C; or A263 replaced with D, E, H, K, R, N, Q, F, W, Y, P, or C.

The resulting constructs can be routinely screened for activities or functions described throughout the specification and known in the art. Preferably, the resulting constructs have an increased t-PALP activity or function (including dominant negative activities or functions), while the remaining t-PALP activities or functions are maintained. More preferably, the resulting constructs have more than one increased t-PALP activity or function (including dominant negative activities or functions), while the remaining t-PALP activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, and/or proprotein form of t-PALP protein, as well as the N- and C-terminal deletion mutants, having the general formulae m-n, $m^1$-$n^1$, $m^2$-$n^2$, $m^3$-$n^3$ or $m^4$-$n^4$, listed below.

Most highly preferred are nucleic acid molecules encoding the mature protein having the amino acid sequence shown in SEQ ID NO:2 or the mature t-PALP amino acid sequence encoded by the deposited cDNA clone.

Most highly preferred are nucleic acid molecules encoding the protease domain of the protein having the amino acid sequence shown in SEQ ID NO:2 or the protease domain of the t-PALP amino acid sequence encoded by the deposited cDNA clone.

Thus, one aspect of the invention provides an isolated nucleic acid molecule comprising a polynucleotide having a nucleotide sequence selected from the group consisting of: (a) a nucleotide sequence encoding a full-length t-PALP polypeptide having the complete amino acid sequence in SEQ ID NO:2 excepting the N-terminal methionine (i.e., positions −20 to 242 of SEQ ID NO:2) or the complete amino acid sequence excepting the N-terminal methionine encoded by the cDNA clone contained in the ATCC Deposit No. 209023; (b) a nucleotide sequence encoding the predicted mature form of the t-PALP polypeptide having the amino acid sequence at positions 1 to 242 in SEQ ID NO:2 or as encoded by the cDNA clone contained in the ATCC Deposit No. 209023; (c) a nucleotide sequence encoding the predicted kringle domain of the t-PALP polypeptide having the amino acid sequence at positions 4 to 63 in SEQ ID NO:2 or as encoded by the cDNA clone contained in the ATCC Deposit No. 209023; (d) a nucleotide sequence encoding a polypeptide comprising the predicted protease domain of the t-PALP polypeptide having the amino acid sequence at positions 64 to 242 in SEQ ID NO:2 or as encoded by the cDNA clone contained in the ATCC Deposit No. 209023; and (e) a nucleotide sequence complementary to any of the nucleotide sequences in (a), (b), (c), (d) or (e) above.

Further embodiments of the invention include isolated nucleic acid molecules that comprise a polynucleotide having a nucleotide sequence at least 90% identical, and more preferably at least 95%, 96%, 97%, 98%, 99%, or 100% identical, to any of the nucleotide sequences in (a), (b), (c), (d) or (e) above, or a polynucleotide which hybridizes under stringent hybridization conditions to a polynucleotide in (a), (b), (c), (d) or (e) above. In other words, these embodiments of the invention include isolated nucleic acid molecules that comprise a polynucleotide having a nucleotide sequence which contains at most 10% differences, and more preferably, at most 5%, 4%, 3%, 2%, 1%, or 0% differences, with any of the nucleotide sequences in (a), (b), (c), (d) or (e) above, or a polynucleotide which hybridizes under stringent hybridization conditions to a polynucleotide in (a), (b), (c), (d) or (e) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a t-PALP polypeptide having an amino acid sequence in (a), (b), (c) or (d) above.

The present invention also relates to recombinant vectors, which include the isolated nucleic acid molecules of the present invention, and to host cells containing the recombinant vectors, as well as to methods of making such vectors and host cells and for using them for production of t-PALP polypeptides or peptides by recombinant techniques.

The present application is directed to nucleic acid molecules at least 90%, 95%, 96%, 97%, 98% or 99% identical to (or stated in another way, at most 10%, 5%, 4%, 3%, 2% or 1% different from) the nucleic acid sequence shown in FIGS. 1A, 1B, and 1C (SEQ ID NO: 1) or to the nucleic acid sequence of the deposited cDNA, irrespective of whether they encode a polypeptide having t-PALP activity. This is because even where a particular nucleic acid molecule does not encode a polypeptide having t-PALP activity, one of skill in the art would still know how to use the nucleic acid molecule, for instance, as a hybridization probe or a polymerase chain reaction (PCR) primer. Uses of the nucleic acid molecules of the present invention that do not encode a polypeptide having t-PALP activity include, inter alia, (1) isolating the t-PALP gene or allelic variants thereof in a cDNA library; (2) in situ hybridization (e.g., "FISH") to metaphase chromosomal spreads to provide precise chromosomal location of the t-PALP gene, as described in Verma et al., Human Chromosomes: A Manual of Basic Techniques, Pergamon Press, New York (1988); and Northern Blot analysis for detecting t-PALP mRNA expression in specific tissues.

By a polynucleotide having a nucleotide sequence at least, for example, 95% "identical" to a reference nucleotide sequence encoding a t-PALP polypeptide is intended that the nucleotide sequence of the polynucleotide is identical to the reference sequence except that the polynucleotide sequence may include up to five mismatches per each 100 nucleotides of the reference nucleotide sequence encoding the t-PALP polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire nucleotide sequence encoding t-PALP, as shown in FIGS. 1A and 1B (SEQ ID NO:1), or any t-PALP polynucleotide fragment as described herein.

As a practical matter, whether any particular nucleic acid molecule is at least 90%, 95%, 96%, 97%, 98% or 99% identical to, for instance, the nucleotide sequences shown in FIGS. 1A and 1B or to the nucleotides sequence of the deposited cDNA clone, or fragments thereof, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

Preferred, however, are nucleic acid molecules having sequences at least 90%, 95%, 96%, 97%, 98% or 99% identical to (or 10%, 5%, 4%, 3%, 2% or 1% different from) the nucleic acid sequence shown in FIGS. 1A, 1B, and 1C (SEQ ID NO:1) or to the nucleic acid sequence of the deposited cDNA which do, in fact, encode a polypeptide having t-PALP protein activity. By "a polypeptide having t-PALP activity" is intended polypeptides exhibiting activity similar, but not necessarily identical, to an activity of the mature t-PALP protein of the invention, as measured in a particular biological assay. For example, the t-PALP protein of the present invention binds to fibrin. Such binding is assumed to mediate the stimulation of plasminogen activation and the ultimate lysis of a plasma clot. The ability of t-PALP, or other related proteins, to bind to fibrin may be assayed in an in vitro analysis, as described by Kalyan and colleagues (*J. Biol. Chem.* 263:3971–3978; 1988). Briefly, a fibrin clot is generated by clotting fibrinogen by the addition of thrombin to 1 unit/mL, incubating for 1 h at room temperature, and compacting by centrifugation. The clot is then washed once with 50 mM Tris-HCl (pH 7.4), 38 mM NaCl. Approximately 1000–2000 ng/mL of isolated t-PALP, or another related protein, are then incubated with the above-described plasminogen-free fibrin clot in a binding buffer consisting of 50 mM Tris-HCl (pH 7.4), 38 mM NaCl, 100 micrograms/mL albumin, 1600 micrograms/mL (~5 micromolar) fibrinogen (plasminogen-free) for 1 h at room temperature. Again, the clot is compacted by centrifugation and washed once with 50 mM Tris-HCl (pH 7.4), 38 mM NaCl. The binding of t-PALP, or other related protein, to fibrin is then quantitated by gel elcetrophoresis and fibrin autography. Such fibrin-binding activity is a useful means of quantifying the ability of t-PALP, or a related protein, to bind to fibrin.

In addition, a general amidolytic activity of t-PALP, or another related protein, may also be assessed through the use of a simple biochemical assay also described by Kalyan and colleagues (J. Biol. Chem. 263:3971–3978; 1988). Cleavage of a synthetic chromogenic substrate (S-2288) may be used to assess the general amidolytic activity of t-PALP, or another related protein. Hydrolysis of this compound produces p-nitroaniline which may be easily quantitated spectrophotometrically by its absorbance at 405 nm. Amidolytic reactions contain 150 mM Tris-HCl (ph 8.4), 100 micrograms/mL albumin, 0.01% Tween-80, 4 nM t-PALP, or other related protein, and 0.6 mM S-2288. Reactions are performed in in microtiter plates and the differential absorbance at 405–540 nm are recorded at ten minute intervals up to 1 hour. Results are plotted as absorbance versus time. This analysis can be enhanced with a slight alteration.

Since it is well-known that fibrin greatly enhances plasminogen activation by t-PA and t-PALP, the generation of plasmin so formed can by conveniently measured by the slightly modified amidolytic assay. In this assay, the chromogenic substrate used is S-2251 (D-Val-L-Ile-Lys-p-nitroanalide). Plasminogen activation reactions contain 50 mM Tris-HCl (ph 7.4), 150 mM NaCl, 100 micrograms/mL albumin, 0.01% Tween-80, 0.3 nM t-PALP, or other related protein, 0.6 mM S-2251, 125 micrograms/mL soluble fibrin, and 1.5 micrograms/mL Glu-plasminogen. Reactions are performed in microtiter plates and are initiated by the addition of plasminogen and S-2251. The differential absorbance at 405–540 nm is recorded at 15 minute intervals and plotted as absorbance versus time.

Further, the activity of t-PALP, or another related polypeptide, can be assessed by using a plasma clot lysis assay, essentially as described Kalyan and colleagues (*J. Biol. Chem.* 263:3971–3978; 1988). In this analysis, the ability of t-PALP, or another related polypeptide, to lyse radiolabeled preformed plasma clots are assessed by bathing clots in plasma containing an appropriate concentration of t-PALP, or another related polypeptide, and monitoring the release of degraded, radiolabeled fibrin. In this assay, 100 microliters of human citrated plasma is clotted in the presence of 0.5 microcuries $^{125}$I-fibrinogen by the addition of $CaCl_2$ to 25 micromolar and 2 units/mL thrombin. The clot is allowed to form at room temperature for 24 hours. The radioactively-labeled clot is then bathed in 1 mL of plasma which contains a series of concentrations of t-PALP, or another related polypeptide, (12.5 to 200 ng/mL); The reactions are shaken gently at 37° C. and samples are taken from the reactions at timepoints up to 24 hours. Aliquots of each sample (10 microliters) are counted in a g counter and expressed as the percent of total counts expected from complete clot lysis.

t-PALP protein binds fibrin, has amidolytic activity, and can lyse a plasma clot in a dose-dependent manner in the above-described assays. Thus, "a polypeptide having t-PALP protein activity" includes polypeptides that also exhibit any of the same activities in the above-described assays in a dose-dependent manner. Although the degree of dose-dependent activity need not be identical to that of the t-PALP protein, preferably, "a polypeptide having t-PALP protein activity" will exhibit substantially similar dose-dependence in a given activity as compared to the t-PALP protein (i.e., the candidate polypeptide will exhibit greater activity or not more than about 25-fold less and, preferably, not more than about tenfold less activity relative to the reference t-PALP protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to (or 10%, 5%, 4%, 3%, 2% or 1% different from) the nucleic acid sequence of the deposited cDNA or the nucleic acid sequence shown in FIGS. 1A, 1B, and 1C (SEQ ID NO:1) will encode a polypeptide "having t-PALP protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having t-PALP protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of t-PALP polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art.

Among vectors preferred for use in bacteria include pHE4-5 (ATCC Accession No. 209311) (and/or other related pHE-type vectors) pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof.

In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J Molecular Recognition* 8:52–58 (1995) and K. Johanson et al., *J. Biol. Chem.* 270:9459–9471 (1995).

The t-PALP protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated t-PALP polypeptide having the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of t-PALP polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.,* 268: 2984–2988; 1993) reported modified KGF proteins that had heparin binding activity even if 3, 8, or 27 amino-terminal amino acid residues were missing. In the present case, since the protein of the invention is related to t-PA, deletions of N-terminal amino acids up to the serine at position 64 of SEQ ID NO:2 may retain some proteolytic activity. Polypeptides having further N-terminal deletions including the serine residue in SEQ ID NO:2 would not be expected to retain such biological activities because it is known that this residue in t-PA is in the beginning of the conserved protease domain required for its observed proteolytic activity.

However, even if deletion of one or more amino acids from the N-terminus of a protein results in modification of loss of one or more biological functions of the protein, other functional activities may still be retained (for example, biological activities, ability to catalyze proteolysis, ability to bind t-PALP receptors). Thus, the ability of the shortened protein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that a t-PALP mutein with a large number of deleted N-terminal amino acid residues may retain some biological or immungenic activities. In fact, peptides composed of as few as six t-PALP amino acid residues may often evoke an immune response.

Accordingly, the present invention further provides polypeptides having one or more residues deleted from the amino terminus of the amino acid sequence of the t-PALP shown in SEQ ID NO:2, up to the serine residue at position number 64, and polynucleotides encoding such polypeptides. In particular, the present invention provides polypeptides comprising, or alternatively consisting of, the amino acid sequence of residues $n^1$–242 of SEQ ID NO:2, where $n^1$ is an integer in the range of (−)21 to 64, and 64 is the position of the first residue from the N-terminus of the complete t-PALP polypeptide (shown in SEQ ID NO:2) believed to be required for proteolytic activity of the t-PALP protein.

More in particular, the invention provides polynucleotides encoding polypeptides having the amino acid sequence of residues of 1 to 242, 2 to 242, 3 to 242, 4 to 242, 5 to 242, 6 to 242, 7 to 242, 8 to 242, 9 to 242, 10 to 242, 11 to 242, 12 to 242, 13 to 242, 14 to 242, 15 to 242, 16 to 242, 17 to 242, 18 to 242, 19 to 242, 20 to 242, 21 to 242, 22 to 242, 23 to 242, 24 to 242, 25 to 242, 26 to 242, 27 to 242, 28 to 242, 29 to 242, 30 to 242, 31 to 242, 32 to 242, 33 to 242, 34 to 242, 35 to 242, 36 to 242, 37 to 242, 38 to 242, 39 to 242, 40 to 242, 41 to 242, 42 to 242, 43 to 242, 44 to 242, 45 to 242, 46 to 242, 47 to 242, 48 to 242, 49 to 242, 50 to 242, 51 to 242, 52 to 242, 53 to 242, 54 to 242, 55 to 242, 56 to 242, 57 to 242, 58 to 242, 59 to 242, 60 to 242, 61 to 242, 62 to 242 or 63 to 242 of SEQ ID NO:2. Polynucleotides encoding these polypeptides also are provided.

Moreover, a signal sequence may be added to these N-terminal deletion contructs. For example, amino acids Met(−)21 to Ser(+)1 of SEQ ID NO:2, amino acids Leu(−)20 to Ser(+)1 of SEQ ID NO:2, amino acids Leu(−)19 to Ser(+)1 of SEQ ID NO:2, amino acids Ala(−)18 to Ser(+)1 of SEQ ID NO:2, amino acids Trp(−)17 to Ser(+)1 of SEQ ID NO:2, amino acids Val(−)16 to Ser(+)1 of SEQ ID NO:2, amino acids Gln(−)15 to Ser(+)1 of SEQ ID NO:2, amino acids Ala(−)14 to Ser(+)1 of SEQ ID NO:2, amino acids Phe(−)13 to Ser(+)1 of SEQ ID NO:2, amino acids Leu(−)12 to Ser(+)1 of SEQ ID NO:2, amino acids Val(−)11 to Ser(+)1 of SEQ ID NO:2, amino acids Ser(−)10 to Ser(+)1 of SEQ ID NO:2, amino acids Asn(−)9 to Ser(+)1 of SEQ ID NO:2, amino acids Met(−)8 to Ser(+)1 of SEQ ID NO:2, amino acids Leu(−)7 to Ser(+)1 of SEQ ID NO:2, amino acids Leu(−)6 to Ser(+)1 of SEQ ID NO:2, amino acids Ala(−)5 to Ser(+)1 of SEQ ID NO:2, amino acids Glu(−)4 to Ser(+)1 of SEQ ID NO:2, amino acids Ala(−)3 to Ser(+)1 of SEQ ID NO:2, amino acids Tyr(−)2 to Ser(+)1 of SEQ ID NO:2 or amino acids Gly(−)1 to Ser(+)1 of SEQ ID NO:2 can be added or fused to the N-terminus of each deletion construct listed above.

Similarly, many examples of biologically functional C-terminal deletion muteins are known. For instance, Interferon-gamma shows up to ten times higher activities by deleting 8–10 amino acid residues from the carboxy terminus of the protein (Dobeli et al., (1988) *J Biotechnol.* 7:199–216). In the present case, since the protein of the invention is a member of the serine protease or t-PA polypeptide families, deletions of C-terminal amino acids up to the serine at position 230 of SEQ ID NO:2 may retain some of the observed proteolytic activity of the carboxy-terminal protease domain of t-PA.

However, even if deletion of one or more amino acids from the C-terminus of a protein results in modification of loss of one or more biological functions of the protein, other functional activities may still be retained (for example, biological activities, ability to catalyze proteolysis, ability to bind t-PALP receptors). Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a t-PALP mutein with a large number of deleted C-terminal amino acid residues may retain some biological or immungenic activities. In fact, peptides composed of as few as six t-PALP amino acid residues may often evoke an immune response.

Accordingly, the present invention further provides polypeptides having one or more residues deleted from the carboxy terminus of the amino acid sequence of the t-PALP shown in SEQ ID NO:2, up to the serine residue at position 230 of SEQ ID NO:2, and polynucleotides encoding such polypeptides. In particular, the present invention provides polypeptides having the amino acid sequence of residues $-20$–$m^1$ of the amino acid sequence in SEQ ID NO:2, where $m^1$ is any integer in the range of 230 to 241, and residue serine is the position of the first residue from the C-terminus of the complete t-PALP polypeptide (shown in SEQ ID NO:2) believed to be required for protease activity of the t-PALP protein.

More in particular, the invention provides polynucleotides encoding polypeptides having the amino acid sequence of residues −20–230, −20–231, −20–232, −20–233, −20–234, −20–235, −20–236, −20–237, −20–238, −20–239, −20–240, −20–241, −20–242 of SEQ ID NO:2. Polynucleotides encoding these polypeptides also are provided.

The invention also provides polypeptides having one or more amino acids deleted from both the amino and the carboxyl termini, which may be described generally as having residues $n^1$–$m^1$ of SEQ ID NO:2, where $n^1$ and $m^1$ are integers as described above.

Also included are a nucleotide sequence encoding a polypeptide consisting of a portion of the complete t-PALP amino acid sequence encoded by the cDNA clone contained in ATCC Deposit No. 209023, where this portion excludes any integer of amino acid residues from 1 to about 82 amino acids from the amino terminus of the complete amino acid sequence encoded by the cDNA clone contained in ATCC Deposit No. 209023, or any integer of amino acid residues from 1 to about 13 amino acids from the carboxy terminus, or any combination of the above amino terminal and carboxy terminal deletions, of the complete amino acid sequence encoded by the cDNA clone contained in ATCC Deposit No. 209023. Polynucleotides encoding all of the above deletion mutant polypeptide forms also are provided.

The present application is also directed to proteins containing polypeptides at least 90%, 95%, 96%, 97%, 98% or 99% identical to the t-PALP polypeptide sequence set forth herein as $m^1$–$n^1$. In preferred embodiments, the application is directed to proteins containing polypeptides at least 90%, 95%, 96%, 97%, 98% or 99% identical to polypeptides having the amino acid sequence of the specific t-PALP N- and C-terminal deletions recited herein. Polynucleotides encoding these polypeptides are also encompassed by the invention.

Also included are a nucleotide sequence encoding a polypeptide consisting of a portion of the complete t-PALP amino acid sequence encoded by the cDNA clone contained in ATCC Deposit No. 209023, where this portion excludes from 1 to about 63 amino acids from the amino terminus of the complete amino acid sequence encoded by the cDNA clone contained in ATCC Deposit No. 209023, or from 1 to about 11 amino acids from the carboxy terminus, or any combination of the above amino terminal and carboxy terminal deletions, of the complete amino acid sequence encoded by the cDNA clone contained in ATCC Deposit No. 209023. Polynucleotides encoding all of the above deletion mutant polypeptide forms also are provided.

As mentioned above, even if deletion of one or more amino acids from the N-terminus of a protein results in modification of loss of one or more biological functions of the protein, other functional activities may still be retained (for example, biological activities, ability to catalyze proteolysis, ability to bind t-PALP receptor). Thus, the ability of the shortened t-PALP mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that a t-PALP mutein with a large number of deleted N-terminal amino acid residues may retain some biological or immungenic activities. In fact, peptides composed of as few as six t-PALP amino acid residues may often evoke an immune response.

Accordingly, the present invention further provides polypeptides having one or more residues deleted from the amino terminus of the amino acid sequence of the t-PALP shown in SEQ ID NO:2, up to the alanine residue at position number 258 (numbering as shown in FIGS. 1A, 1B, and 1C; A-258 is A-237 in SEQ ID NO:2), and polynucleotides encoding such polypeptides. In particular, the present invention provides polypeptides comprising the amino acid sequence of residues $n^2$–258 of FIGS. 1A, 1B, and 1C ($n^2$–237 of SEQ ID NO:2), where n is an integer in the range of 2–258 (–21–258 of SEQ ID NO:2), and 258 is the position of the first residue from the N-terminus of the complete t-PALP polypeptide (shown as residue 237 in SEQ ID NO:2) believed to be required for at least immunogenic activity of the t-PALP protein.

More in particular, the invention provides polynucleotides encoding polypeptides comprising, or alternatively consisting of, the amino acid sequence of residues of L-2 to A-263; L-3 to A-263; A-4 to A-263; W-5 to A-263; V-6 to A-263; Q-7 to A-263; A-8 to A-263; F-9 to A-263; L-10 to A-263; V-11 to A-263; S-12 to A-263; N-13 to A-263; M-14 to A-263; L-15 to A-263; L-16 to A-263; A-17 to A-263; E-18 to A-263; A-19 to A-263; Y-20 to A-263; G-21 to A-263; S-22 to A-263; G-23 to A-263; G-24 to A-263; C-25 to A-263; F-26 to A-263; W-27 to A-263; D-28 to A-263; N-29 to A-263; G-30 to A-263; H-31 to A-263; L-32 to A-263; Y-33 to A-263; R-34 to A-263; E-35 to A-263; D-36 to A-263; Q-37 to A-263; T-38 to A-263; S-39 to A-263; P-40 to A-263; A-41 to A-263; P-42 to A-263; G-43 to A-263; L-44 to A-263; R-45 to A-263; C-46 to A-263; L-47 to A-263; N-48 to A-263; W-49 to A-263; L-50 to A-263; D-51 to A-263; A-52 to A-263; Q-53 to A-263; S-54 to A-263; G-55 to A-263; L-56 to A-263; A-57 to A-263; S-58 to A-263; A-59 to A-263; P-60 to A-263; V-61 to A-263; S-62 to A-263; G-63 to A-263; A-64 to A-263; G-65 to A-263; N-66 to A-263; H-67 to A-263; S-68 to A-263; Y-69 to A-263; C-70 to A-263; R-71 to A-263; N-72 to A-263; P-73 to A-263; D-74 to A-263; E-75 to A-263; D-76 to A-263; P-77 to A-263; R-78 to A-263; G-79 to A-263; P-80 to A-263; W-81 to A-263; C-82 to A-263; Y-83 to A-263; V-84 to A-263; S-85 to A-263; G-86 to A-263; E-87 to A-263; A-88 to A-263; G-89 to A-263; V-90 to A-263; P-91 to A-263; E-92 to A-263; K-93 to A-263; R-94 to A-263; P-95 to A-263; C-96 to A-263; E-97 to A-263; D-98 to A-263; L-99 to A-263; R-100 to A-263; C-101 to A-263; P-102 to A-263; E-103 to A-263; T-104 to A-263; T-105 to A-263; S-106 to A-263; Q-107 to A-263; A-108 to A-263; L-109 to A-263; P-110 to A-263; A-111 to A-263; F112 to A-263; T-113 to A-263; T-114 to A-263; E-115 to A-263; I-116 A-263; G-122 to A-263; P-123 to A-263; G-124 to A-263; A-125 to A-263; D-126 to A-263; E-127 to A-263; V-128 to A-263; Q-129 to A-263; V-130 to A-263; F-131 to A-263; A-132 to A-263; P-133 to A-263; A-134 to A-263; N-135 to A-263; A-136 to A-263; L-137 to A-263; P-138 to A-263; A-139 to A-263; R-140 to A-263; S-141 to A-263; E-142 to A-263; A-143 to A-263; A-144 to A-263; A-145 to A-263; V-146 to A-263; Q-147 to A-263; P-148 to A-263; V-149 to A-263; I-150 to A-263; G-151 to A-263; I-152 to A-263; S-153 to A-263; Q-154 to A-263; R-155 to A-263; V-156 to A-263; R-157 to A-263; M-158 to A-263; N-159 to A-263; S-160 to A-263; K-161 to A-263; E-162 to A-263; K-163 to A-263; K-164 to A-263; D-165 to A-263; L-166 to A-263; G-167 to A-263; T-168 to A-263; L-169 to A-263; G-170 to A-263; Y-171 to A-263; V-172 to A-263; L-173 to A-263; G-174 to A-263; I-175 to A-263; T-176 to A-263; M-177 to A-263; M-178 to A-263; V-179 to A-263; I-180 to A-263; I-181 to A-263; I-182 to A-263; A-183 to A-263; I-184 to A-263; G-185 to A-263; A-186 to A-263; G-187 to A-263; I-188 to A-263; I-189 to A-263; L-190 to A-263; G-191 to A-263; Y-192 to A-263; S-193 to A-263; Y-194 to A-263; K-195 to A-263; R-196 to A-263; G-197 to A-263; K-198 to A-263; D-199 to A-263; L-200 to A-263; K-201 to A-263; E-202 to A-263; Q-203 to A-263; H-204 to A-263; D-205 to A-263; Q-206 to A-263; K-207 to A-263; V-208 to A-263; C-209 to A-263; E-210 to A-263; R-211 to A-263; E-212 to A-263; M-213 to A-263; Q-214 to A-263; R-215 to A-263; I-216 to A-263; T-217 to A-263; L-218 to A-263; P-219 to A-263; L-220 to A-263; S-221 to A-263; A-222 to A-263; F-223 to A-263; T-224 to A-263; N-225 to A-263; P-226 to A-263; T-227 to A-263; C-228 to A-263; E-229 to A-263; I-230 to A-263; V-231 to A-263; D-232 to A-263; E-233 to A-263; K-234 to A-263; T-235 to A-263; V-236 to A-263; V-237 to A-263; V-238 to A-263; H-239 to A-263; T-240 to A-263; S-241 to A-263; Q-242 to A-263; T-243 to A-263; P-244 to A-263; V-245 to A-263; D-246 to A-263; P-247 to A-263; Q-248 to A-263; E-249 to A-263; G-250 to A-263; S-251 to A-263; T-252 to A-263; P-253 to A-263; L-254 to A-263; M-255 to A-263; G-256 to A-263; Q-257 to A-263; and A-258 to A-263 of the t-PALP sequence shown in SEQ ID NO:2 using the numbering scheme of FIGS. 1A, 1B, and 1C.

Also as mentioned above, even if deletion of one or more amino acids from the C-terminus of a protein results in modification of loss of one or more biological functions of the protein, other functional activities may still be retained (for example, biological activities, ability to catalyze proteolysis, ability to bind t-PALP receptor). Thus, the ability of the shortened t-PALP mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a t-PALP mutein with a large number of deleted C-terminal amino acid residues may retain some biological or immungenic activities. In fact, peptides composed of as few as six t-PALP amino acid residues may often evoke an immune response.

Accordingly, the present invention further provides polypeptides having one or more residues deleted from the carboxy terminus of the amino acid sequence of the t-PALP shown in SEQ ID NO:2, up to the valine residue at position number 6 (numbering as shown in FIGS. 1A, 1B, and 1C; the valine at position 6 is the valine at position −14 in SEQ ID NO:2), and polynucleotides encoding such polypeptides. In particular, the present invention provides polypeptides comprising the amino acid sequence of residues 1–$m^2$ of FIGS. 1A, 1B, and 1C (−21–$m^2$ of SEQ ID NO:2), where $m^2$ is an integer in the range of 7–263 (−13–242 of SEQ ID NO:2), and 6 is the position of the first residue from the C-terminus of the complete t-PALP polypeptide (shown as residue −14 in SEQ ID NO:2) believed to be required for at least immunogenic activity of the t-PALP protein.

More in particular, the invention provides polynucleotides encoding polypeptides having the amino acid sequence of residues M-1 to G-262; M-1 to P-261; M-1 to T-260; M-1 to G-259; M-1 to A-258; M-1 to Q-257; M-1 to G-256; M-1 to M-255; M-1 to L-254; M-1 to P-253; M-1 to T-252; M-1 to S-251; M-1 to G-250; M-1 to E-249; M-1 to Q-248; M-1 to P-247; M-1 to D-246; M-1 to V-245; M-1 to P-244; M-1 to T-243; M-1 to Q-242; M-1 to S-241; M-1 to T-240; M-1 to H-239; M-1 to V-238; M-1 to V-237; M-1 to V-236; M-1 to T-235; M-1 to K-234; M-1 to E-233; M-1 to D-232; M-1 to V_231; M-1 to I-230; M-1 to E-229; M-1 to C-228; M-1 to T-227; M-1 to P-226; M-1 to N-225; M-1 to T-224; M-1 to F-223; M-1 to A-222; M-1 to S-221; M-1 to L-220; M-1 to P-219; M-1 to L-218; M-1 to T-217; M-1 to I-216; M-1 to R-215; M-1 to Q-214; M-1 to M-213; M-1 to E-212; M-1 to R-211; M-1 to E-210; M-1 to C-209; M-1 to V-208; M-1 to K-207; M-1 to Q-206; M-1 to D-205; M-1 to H-204; M-1 to Q-203; M-1 to E-202; M-1 to K-201; M-1 to L-200; M-1 to D-199; M-1 to K-198; M-1 to G-197; M-1 to R-196; M-1 to K-195; M-1 to Y-194; M-1 to S-193; M-1 to Y-192; M-1 to G-191; M-1 to L-190; M-1 to I-189; M-1 to I-188; M-1 to G-187; M-1 to A-186; M-1 to G-185; M-1 to 1-184; M-1 to A-183; M-1 to 1-182; M-1 to 1-181; M-1 to 1-180; M-1 to V-179; M-1 to M-178; M-1 to M-177; M-1 to T-176; M-1 to 1-175; M-1 to G-174; M-1 to L-173; M-1 to V-172; M-1 to Y-171; M-1 to G-170; M-1 to L-169; M-1 to T-168; M-1 to G-167; M-1 to L-166; M-1 to D-165; M-1 to K-164; M-1 to K-163; M-1 to E-162; M-1 to K-161; M-1 to S-160; M-1 to N-159; M-1 to M-158; M-1 to R-157; M-1 to V-156; M-1 to R-155; M-1 to Q-154; M-1 to S-153; M-1 to I-152; M-1 to G-151; M-1 to I-150; M-1 to V-149; M-1 to P-148; M-1 to Q-147; M-1 to V-146; M-1 to A-145; M-1 to A-144; M-1 to A-143; M-1 to E-142; M-1 to S-141; M-1 to R-140; M-1 to A-139; M-1 to P-138; M-1 to L-137; M-1 to A-136; M-1 to N-135; M-1 to A-134; M-1 to P-133; M-1 to A-132; M-1 to F-131; M-1 to V-130; M-1 to Q-129; M-1 to V-128; M-1 to E-127; M-1 to D-126; M-1 to A-125; M-1 to G-124; M-1 to P-123; M-1 to G-122; M-1 to E-121; M-1 to S-120; M-1 to A-119; M-1 to E-118; M-1 to Q-117; M-1 to I-116; M-1 to E-115; M-1 to T-114; M-1 to T-113; M-1 to F-112; M-1 to A-111; M-1 to P-110; M-1 to L-109; M-1 to A-108; M-1 to Q-107; M-1 to S-106; M-1 to T-105; M-1 to T-104; M-1 to E-103; M-1 to P-102; M-1 to C-101; M-1 to R-100; M-1 to L-99; M-1 to D-98; M-1 to E-97; M-1 to C-96; M-1 to P-95; M-1 to R-94; M-1 to K-93; M-1 to E-92; M-1 to P-91; M-1 to V-90; M-1 to G-89; M-1 to A-88; M-1 to E-87; M-1 to G-86; M-1 to S-85; M-1 to V-84; M-1 to Y-83; M-1 to C-82; M-1 to W-81; M-1 to P-80; M-1 to G-79; M-1 to R-78; M-1 to P-77; M-1 to D-76; M-1 to E-75; M-1 to D-74; M-1 to P-73; M-1 to N-72; M-1 to R-71; M-1 to C-70; M-1 to Y-69; M-1 to S-68; M-1 to H-67; M-1 to N-66; M-1 to G-65; M-1 to A-64; M-1 to G-63; M-1 to S-62; M-1 to V-61; M-1 to P-60; M-1 to A-59; M-1 to S-58; M-1 to A-57; M-1 to L-56; M-1 to G-55; M-1 to S-54; M-1 to Q-53; M-1 to A-52; M-1 to D-51; M-1 to L-50; M-1 to W-49; M-1 to N-48; M-1 to L-47; M-1 to C-46; M-1 to R-45; M-1 to L-44; M-1 to G-43; M-1 to P-42; M-1 to A-41; M-1 to P-40; M-1 to S-39; M-1 to T-38; M-1 to Q-37; M-1 to D-36; M-1 to E-35; M-1 to R-34; M-1 to Y-33; M-1 to L-32; M-1 to H-31; M-1 to G-30; M-1 to N-29; M-1 to D-28; M-1 to W-27; M-1 to F-26; M-1 to C-25; M-1 to G-24; M-1 to G-23; M-1 to S-22; M-1 to G-21; M-1 to Y-20; M-1 to A-19; M-1 to E-18; M-1 to A-17; M-1 to L-16; M-1 to L-15; M-1 to M-14; M-1 to N-13; M-1 to S-12; M-1 to V-11; M-1 to L-10; M-1 to F-9; M-1 to A-8; M-1 to Q-7; and M-1 to V-6 of the t-PALP sequence shown in SEQ ID NO:2 using the numbering scheme of FIGS. 1A, 1B, and 1C. Polynucleotides encoding these polypeptides also are provided.

Moreover, a signal sequence may be added to these C-terminal deletion contructs. For example, amino acids Met(−)21 to Ser(+)1 of SEQ ID NO:2, amino acids Leu(−) 20 to Ser(+)1 of SEQ ID NO:2, amino acids Leu(−)19 to Ser(+)1 of SEQ ID NO:2, amino acids Ala(−)18 to Ser(+)1 of SEQ ID NO:2, amino acids Trp(−)17 to Ser(+)1 of SEQ ID NO:2, amino acids Val(−)16 to Ser(+)1 of SEQ ID NO:2, amino acids Gln(−)15 to Ser(+)1 of SEQ ID NO:2, amino acids Ala(−)14 to Ser(+)1 of SEQ ID NO:2, amino acids Phe(−)13 to Ser(+)1 of SEQ ID NO:2, amino acids Leu(−)12 to Ser(+)1 of SEQ ID NO:2, amino acids Val(−)11 to Ser(+)1 of SEQ ID NO:2, amino acids Ser(−)10 to Ser(+)1 of SEQ ID NO:2, amino acids Asn(−)9 to Ser(+)1 of SEQ ID NO:2, amino acids Met(−)8 to Ser(+)1 of SEQ ID NO:2, amino acids Leu(−)7 to Ser(+)1 of SEQ ID NO:2, amino acids Leu(−)6 to Ser(+)1 of SEQ ID NO:2, amino acids Ala(−)5 to Ser(+)1 of SEQ ID NO:2, amino acids Glu(−)4 to Ser(+)1 of SEQ ID NO:2, amino acids Ala$(-)_3$ to Ser(+)1 of SEQ ID NO:2, amino acids Tyr(−)2 to Ser(+)1 of SEQ ID NO:2, and amino acids Gly(−)1 to Ser(+)1 of SEQ ID NO:2 can be added or fused to the N-terminus of each deletion construct listed above.

The invention also provides polypeptides having one or more amino acids deleted from both the amino and the carboxyl termini, which may be described generally as having residues n to $m^2$ of SEQ ID NO:2, where $n^2$ and $m^2$ are integers as described above.

Also included are a nucleotide sequence encoding a polypeptide consisting of a portion of the complete t-PALP amino acid sequence encoded by the cDNA clone contained in ATCC Deposit No. 209023, where this portion excludes any integer of amino acid residues from 1 to about 232 amino acids from the amino terminus of the complete amino acid sequence encoded by the cDNA clone contained in ATCC Deposit No. 209023, or any integer of amino acid residues from 1 to about 232 amino acids from the carboxy terminus, or any combination of the above amino terminal and carboxy terminal deletions, of the complete amino acid sequence encoded by the cDNA clone contained in ATCC Deposit No. 209023. Polynucleotides encoding all of the above deletion mutant polypeptide forms also are provided.

Accordingly, the present invention further provides polypeptides having one or more residues deleted from the amino terminus of the kringle domain (Ser-1 to Val-63) of t-PALP shown in SEQ ID NO:2, up to the glycine residue at position number 58, and polynucleotides encoding such polypeptides. In particular, the present invention provides polypeptides comprising, or alternatively consisting of, the amino acid sequence of residues $n^3$ to 63 of SEQ ID NO:2, where $n^3$ is an integer in the range of 1 to 58 (SEQ ID NO:2).

More in particular, the invention provides polynucleotides encoding polypeptides having the amino acid sequence of residues 1 to 63; 2 to 63; 3 to 63; 4 to 63; 5 to 63; 6 to 63; 7 to 63; 8 to 63; 9 to 63; 10 to 63; 11 to 63; 12 to 63; 13 to 63; 14 to 63; 15 to 63; 16 to 63; 17 to 63; 18 to 63; 19 to 63; 20 to 63; 21 to 63; 22 to 63; 23 to 63; 24 to 63; 25 to 63; 26 to 63; 27 to 63; 28 to 63; 29 to 63; 30 to 63; 31 to 63; 32 to 63; 33 to 63; 34 to 63; 35 to 63; 36 to 63; 37 to 63; 38 to 63; 39 to 63; 40 to 63; 41 to 63; 42 to 63; 43to 63; 44 to 63; 45 to 63; 46 to 63; 47 to 63; 48 to 63; 48 to 63; 49 to 63; 50 to 63; 51 to 63; 52 to 63; 53 to 63; 54 to 63; 55 to 63; 56 to 63; 57 to 63; and 58 to 63 of SEQ ID NO:2. Polynucleotides encoding these polypeptides also are provided.

Moreover, a signal sequence may be added to these N-terminal deletion contructs. For example, amino acids Met(−)21 to Ser(+)1 of SEQ ID NO:2, amino acids Leu(−) 20 to Ser(+)1 of SEQ ID NO:2, amino acids Leu(−)19 to Ser(+)1 of SEQ ID NO:2, amino acids Ala(−)18 to Ser(+)1 of SEQ ID NO:2, amino acids Trp(−)17 to Ser(+)1 of SEQ ID NO:2, amino acids Val(−)16 to Ser(+)1 of SEQ ID NO:2, amino acids Gln(−)15 to Ser(+)1 of SEQ ID NO:2, amino acids Ala(−)14 to Ser(+)1 of SEQ ID NO:2, amino acids Phe(−)13 to Ser(+)1 of SEQ ID NO:2, amino acids Leu(−)12 to Ser(+)1 of SEQ ID NO:2, amino acids Val(−)11 to Ser(+)1 of SEQ ID NO:2, amino acids Ser(−)10 to Ser(+)1 of SEQ ID NO:2, amino acids Asn(−)9 to Ser(+)1 of SEQ ID NO:2, amino acids Met(−)8 to Ser(+)1 of SEQ ID NO:2, amino acids Leu(−)7 to Ser(+)1 of SEQ ID NO:2, amino acids Leu(−)6 to Ser(+)1 of SEQ ID NO:2, amino acids Ala(−)5 to Ser(+)1 of SEQ ID NO:2, amino acids Glu(−)4 to Ser(+)1 of SEQ ID NO:2, amino acids Ala$(-)_3$ to Ser(+)1 of SEQ ID NO:2, amino acids Tyr(−)2 to Ser(+)1 of SEQ ID NO:2, and amino acids Gly(−)1 to Ser(+)1 of SEQ ID NO:2 can be added or fused to the N-terminus of each deletion construct listed above.

The present invention further provides polypeptides having one or more amino acid residues deleted from the carboxy terminus of the kringle domain (Ser-1 to Val-63) of t-PALP (shown in SEQ ID NO:2), up to the tryptophan residue at position 6 of SEQ ID NO:2, and polynucleotides encoding such polypeptides. In particular, the present invention provides polypeptides having the amino acid sequence of residues 1 to $m^3$ of the amino acid sequence in SEQ ID NO:2, where $m^3$ is any integer in the range of 6 to 63 (shown in SEQ ID NO:2).

More in particular, the invention provides polynucleotides encoding polypeptides having the amino acid sequence of residues S-1 to V-63; S-1 to Y-62; S-1 to C-61; S-1 to W-60; S-1 to P-59; S-1 to G-58; S-1 to R-57; S-1 to P-56; S-1 to D-55; S-1 to E-54; S-1 to D-53; S-1 to P-52; S-1 to N-51; S-1 to R-50; S-1 to C-49; S-1 to Y-48; S-1 to S-47; S-1 to H-46; S-1 to N-45; S-1 to G-44; S-1 to A-43; S-1 to G-42; S-1 to S-41; S-1 to V-40; S-1 to P-39; S-1 to A-38; S-1 to S-37; S-1 to A-36; S-1 to L-35; S-1 to S-33; S-1 to Q-32; S-1 to A-31; S-1 to D-30; S-1 to L-29; S-1 to W-28; S-1 to N-27; S-1 to L-26; S-1 to C-25; S-1 to R-24; S-1 to L-23; S-1 to G-22; S-1 to P-21; S-1 to P-19; S-1 to S-18; S-1 to T-17; S-1 to Q-16; S-1 to D-15; S-1 to E-14; S-1 to Y-12; S-1 to L-11; S-1 to H-10; S-1 to G-9; S-1 to N-8; S-1 to D-7; and S-1 and W-6 of SEQ ID NO:2. Polynucleotides encoding these polypeptides also are provided.

Moreover, a signal sequence may be added to these C-terminal deletion contructs. For example, amino acids Met(−)21 to Ser(+)1 of SEQ ID NO:2, amino acids Leu(−)20 to Ser(+)1 of SEQ ID NO:2, amino acids Leu(−)19 to Ser(+)1 of SEQ ID NO:2, amino acids Ala(−)18 to Ser(+)1 of SEQ ID NO:2, amino acids Trp(−)17 to Ser(+)1 of SEQ ID NO:2, amino acids Val(−)16 to Ser(+)1 of SEQ ID NO:2, amino acids Gln(−)15 to Ser(+)1 of SEQ ID NO:2, amino acids Ala(−)14 to Ser(+)1 of SEQ ID NO:2, amino acids Phe(−)13 to Ser(+)1 of SEQ ID NO:2, amino acids Leu(−)12 to Ser(+)1 of SEQ ID NO:2, amino acids Val(−)11 to Ser(+)1 of SEQ ID NO:2, amino acids Ser(−)10 to Ser(+)1 of SEQ ID NO:2, amino acids Asn(−)9 to Ser(+)1 of SEQ ID NO:2, amino acids Met(−)8 to Ser(+)1 of SEQ ID NO:2, amino acids Leu(−)7 to Ser(+)1 of SEQ ID NO:2, amino acids Leu(−)6 to Ser(+)1 of SEQ ID NO:2, amino acids Ala(−)5 to Ser(+)1 of SEQ ID NO:2, amino acids Glu(−)4 to Ser(+)1 of SEQ ID NO:2, amino acids Ala$(-)_3$ to Ser(+)1 of SEQ ID NO:2, amino acids Tyr(−)2 to Ser(+)1 of SEQ ID NO:2, and amino acids Gly(−)1 to Ser(+)1 of SEQ ID NO:2 can be added or fused to the N-terminus of each deletion construct listed above.

The invention also provides polypeptides having one or more amino acids deleted from both the amino and the carboxyl termini of the kringle domain of t-PALP, which may be described generally as having residues $n^3$–$m^3$ of SEQ ID NO:2, where $n^3$ and $m^3$ are integers as described above.

Also included are a nucleotide sequence encoding a polypeptide consisting of a portion of the complete t-PALP amino acid sequence encoded by the cDNA clone contained in ATCC Deposit No. 209023, where this portion excludes any integer of amino acid residues from 1 to about 58 amino acids from the amino terminus of the complete amino acid sequence encoded by the cDNA clone contained in ATCC Deposit No. 209023, or any integer of amino acid residues from 1 to about 58 amino acids from the carboxy terminus, or any combination of the above amino terminal and carboxy terminal deletions, of the complete amino acid sequence encoded by the cDNA clone contained in ATCC Deposit No. 209023. Polynucleotides encoding all of the above deletion mutant polypeptide forms also are provided.

The present application is also directed to proteins containing polypeptides at least 90%, 95%, 96%, 97%, 98% or 99% identical to the t-PALP polypeptide sequence set forth herein $m^3$–$n^3$. In preferred embodiments, the application is directed to proteins containing polypeptides at least 90%, 95%, 96%, 97%, 98% or 99% identical to polypeptides having the amino acid sequence of the specific t-PALP N- and C-terminal deletions recited herein. Polynucleotides encoding these polypeptides are also encompassed by the invention.

Accordingly, the present invention further provides polypeptides having one or more residues deleted from the amino terminus of the protease domain (Ser-64 to Ala-242) of t-PALP shown in SEQ ID NO:2, up to the alanine residue at position number 237, and polynucleotides encoding such polypeptides. In particular, the present invention provides polypeptides comprising, or alternatively consisting of, the amino acid sequence of residues $n^4$ to 242 of SEQ ID NO:2, where $n^4$ is an integer in the range of 64 to 237 (SEQ ID NO:2).

More in particular, the invention provides polynucleotides encoding polypeptides having the amino acid sequence of residues S-64 to A-242; G-65 to A-242; E-66 to A-242; A-67 to A-242; G-68 to A-242; V-69 to A-242; P-70 to A-242; E-71 to A-242; K-72 to A-242; R-73 to A-242; P-74 to A-242; C-75 to A-242; E-76 to A-242; D-77 to A-242; L-78 to A-242; R-79 to A-242; C-80 to A-242; P-81 to A-242; E-82 to A-242; T-83 to A-242; T-84 to A-242; S-85 to A-242; Q-86 to A-242; A-87 to A-242; L-88 to A-242; P-89 to A-242; A-90 to A-242; F-91 to A-242; T-92 to A-242; T-93 to A-242; E-94 to A-242; I-95 to A-242; Q-96 to A-242; E-97 to A-242; A-98 to A-242; S-99 to A-242; E-100 to A-242; G-101 to A-242; P-102 to A-242; G-103 to A-242; A-104 to A-242; D-105 to A-242; E-106 to A-242; V-107 to A-242; Q-108 to A-242; V-109 to A-242; F-110 to A-242; A-111 to A-242; P-112 to A-242; A-113 to A-242; N-114 to A-242; A-115 to A-242; L-116 to A-242; P-117 to A-242; A-118 to A-242; R-119 to A-242; S-120 to A-242; E-121 to A-242; A-122 to A-242; A-123 to A-242; A-124 to A-242; V-125 to A-242; Q-126 to A-242; P-127 to A-242; V-128 to A-242; I-129 to A-242; G-130 to A-242; I-131 to A-242; S-132 to A-242; Q-133 to A-242; R-134 to A-242; V-135 to A-242; R-136 to A-242; M-137 to A-242; N-138 to A-242; S-139 to A-242; K-140 to A-242; E-141 to A-242; K-142 to A-242; K-143 to A-242; D-144 to A-242; L-145 to A-242; G-146 to A-242; T-147 to A-242; L-148 to A-242; G-149 to A-242; Y-150 to A-242; V-151 to A-242; L-152 to A-242; G-153 to A-242; I-154 to A-242; T-155 to A-242; M-156 to A-242; M-157 to A-242; V-158 to A-242; I-159 to A-242; I-160 to A-242; I-161 to A-242; A-162 to A-242; I-163 to A-242; G-164 to A-242; A-165 to A-242; G-166 to A-242; I-167 to A-242; I-168 to A-242; L-169 to A-242; G-170 to A-242; Y-171 to A-242; S-172 to A-242; Y-173 to A-242; K-174 to A-242; R-175 to A-242; G-176 to A-242; K-177 to A-242; D-178 to A-242; L-179 to A-242; K-180 to A-242; E-181 to A-242; Q-182 to A-242; H-183 to A-242; D-184 to A-242; Q-185 to A-242; K-186 to A-242; V-187 to A-242; C-188 to A-242; E-189 to A-242; R-190 to A-242; E-91 to A-242; M-192 to A-242; Q-193 to A-242; R-194 to A-242; I-195 to A-242; T-196 to A-242; L-197 to A-242; P-198 to A-242; L-199 to A-242; S-200 to A-242; A-201 to A-242; F-202 to A-242; T-203 to A-242; N-204 to A-242; P-205 to A-242; T-206 to A-242; C-207 to A-242; E-208 to A-242; 1-209 to A-242; V-210 to A-242; D-211 to A-242; E-212 to A-242; K-213 to A-242; T-214 to A-242; V-215 to A-242; V-216 to A-242; V-217 to A-242; H-218 to A-242; T-219 to A-242; S-220 to A-242; Q-221 to A-242; T-222 to A-242; P-223 to A-242; V-224 to A-242; D-225 to A-242; P-226 to A-242; Q-227 to A-242; E-228 to A-242; G-229 to A-242; S-230 to A-242; T-231 to A-242; P-232 to A-242; L-233 to A-242; M-234 to A-242; G-235 to A-242; Q-236 to A-242; and A-237 to A-242 of SEQ ID NO:2. Polynucleotides encoding these polypeptides also are provided.

Moreover, a signal sequence may be added to these N-terminal deletion contructs. For example, amino acids Met(−)21 to Ser(+)1 of SEQ ID NO:2, amino acids Leu(−) 20 to Ser(+)1 of SEQ ID NO:2, amino acids Leu(−)19 to Ser(+)1 of SEQ ID NO:2, amino acids Ala(−)18 to Ser(+)1 of SEQ ID NO:2, amino acids Trp(−)17 to Ser(+)1 of SEQ ID NO:2, amino acids Val(−)16 to Ser(+)1 of SEQ ID NO:2, amino acids Gln(−)15 to Ser(+)1 of SEQ ID NO:2, amino acids Ala(−)14 to Ser(+)1 of SEQ ID NO:2, amino acids Phe(−)13 to Ser(+)1 of SEQ ID NO:2, amino acids Leu(−)12 to Ser(+)1 of SEQ ID NO:2, amino acids Val(−)11 to Ser(+)1 of SEQ ID NO:2, amino acids Ser(−)10 to Ser(+)1 of SEQ ID NO:2, amino acids Asn(−)9 to Ser(+)1 of SEQ ID NO:2, amino acids Met(−)8 to Ser(+)1 of SEQ ID NO:2, amino acids Leu(−)7 to Ser(+)1 of SEQ ID NO:2, amino acids Leu(−)6 to Ser(+)1 of SEQ ID NO:2, amino acids Ala(−)5 to Ser(+)1 of SEQ ID NO:2, amino acids Glu(−)4 to Ser(+)1 of SEQ ID NO:2, amino acids Ala(−)3 to Ser(+)1 of SEQ ID NO:2, amino acids Tyr(−)2 to Ser(+)1 of SEQ ID NO:2, and amino acids Gly(−)1 to Ser(+)1 of SEQ ID NO:2 can be added to the N-terminus of each deletion construct listed above.

The present invention further provides polypeptides having one or more amino acid residues deleted from the carboxy terminus of the protease domain (Ser-64 to Ala-242) of t-PALP (shown in SEQ ID NO:2), up to the valine residue at position 69 of SEQ ID NO:2, and polynucleotides encoding such polypeptides. In particular, the present invention provides polypeptides having the amino acid sequence of residues 64 to $m^4$ of the amino acid sequence in SEQ ID NO:2, where $m^4$ is any integer in the range of 69 to 242 (shown in SEQ ID NO:2).

More in particular, the invention provides polynucleotides encoding polypeptides having the amino acid sequence of residues S-64 to A-242; S-64 to G-241; S-64 to P-240; S-64 to T-239; S-64 to G-238; S-64 to A-237; S-64 to Q-236; S-64 to G-235; S-64 to M-234; S-64 L-233; S-64 to P-232; S-64 to T-231; S-64 to S-230; S-64 to G-229; S-64 to E-228; S-64 to Q-227; S-64 to P-226; S-64 to D-225; S-64 to V-224; S-64 to P-223; S-64 to T-222; S-64 to Q-221; S-64 to S-220; S-64 to T-219; S-64 to H-218; S-64 to V-217; S-64 to V-216; S-64 to V-215; S-64 to T-214; S-64 to K-213; S-64 to E-212; S-64 to D-211; S-64 to V-210; S-64 to I-209; S-64 to E-208; S-64 to C-207; S-64 to T-206; S-64 to P-205; S-64 to N-204; S-64 to T-203; S-64 to F-202; S-64 to A-201; S-64 to S-200; S-64 to L-199; S-64 to P-198; S-64 to L-197; S-64 to T-196; S-64 to I-195; S-64 to R-194; S-64 to Q-193; S-64 to M-192; S-64 to E-191; S-64 to R-190; S-64 to E-189; S-64 to C-188; S-64 to V-187; S-64 to K-186; S-64 to Q-185; S-64 to D-184; S-64 to H-183; S-64 to Q-182; S-64 to E-181; S-64 to K-180; S-64 to L-179; S-64 to D-178; S-64 to K-177; S-64 to G-176; S-64 to R-175; S-64 to K-174; S-64 to Y-173; S-64 to S-172; S-64 to Y-171; S-64 to G-170; S-64 to L-169; S-64 to 1-168; S-64 to 1-167; S-64 to G-166; S-64 to A-165; S-64 to G-164; S-64 to 1-163; S-64 to A-162; S-64 to 1-161; S-64 to I-160; S-64 to I-159; S-64 to V-158; S-64 to M-157; S-64 to M-156; S-64 to T-155; S-64 to I-154; S-64 to G-153; S-64 to L-152; S-64 to V-151; S-64 to Y-150; S-64 to G-149; S-64 to L-148; S-64 to T-147; S-64 to G-146; S-64 to L-145; S-64 to D-144; S-64 to K-143; S-64 to K-142; S-64 to E-141; S-64 to K-140; S-64 to S-139; S-64 to N-138; S-64 to M-137; S-64 to R-136; S-64 to V-135; S-64 to R-134; S-64 to Q-133; S-64 to S-132; S-64 to 1-131; S-64 to G-130; S-64 to 1-129; S-64 to V-128; S-64 to P-127; S-64 to Q-126; S-64 to V-125; S-64 to A-124; S-64 to A-123; S-64 to A-122; S-64 to E-121; S-64 to S-120; S-64 to R-119; S-64 to A-118; S-64 to P-117; S-64 to L-116; S-64 to A-115; S-64 to N-114; S-64 to A-113; S-64 to P-112; S-64 to A-111; S-64 to F-110; S-64 to V-109; S-64 to Q-108; S-64 to V-107; S-64 to E-106; S-64 to D-105; S-64 to A-104; S-64 to G-103; S-64 to P-102; S-64 to G-101; S-64 to E-100; S-64 to S-99; S-64 to A-98; S-64 to E-97; S-64 to Q-96; S-64 to I-95; S-64 to E-94; S-64 to T-93; S-64 to T-92; S-64 to F-91; S-64 to A-90; S-64 to P-89; S-64 to L-88; S-64 to A-87; S-64 to Q-86; S-64 to S-85; S-64 to T-84; S-64 to T-83; S-64 to E-82; S-64 to P-81; S-64 to C-80; S-64 to R-79; S-64 to L-78; S-64 to D-77; S-64 to E-76; S-64 to C-75; S-64 to P-74; S-64 to R-73; S-64 to K-72; S-64 to E-71; S-64 to P-70; and provided.

Moreover, a signal sequence may be added to these C-terminal deletion contructs. For example, amino acids Met(−)21 to Ser(+)1 of SEQ ID NO:2, amino acids Leu(−) 20 to Ser(+)1 of SEQ ID NO:2, amino acids Leu(−)19 to Ser(+)1 of SEQ ID NO:2, amino acids Ala(−)18 to Ser(+)1 of SEQ ID NO:2, amino acids Trp(−)17 to Ser(+)1 of SEQ ID NO:2, amino acids Val(−)16 to Ser(+)1 of SEQ ID NO:2, amino acids Gln(−)15 to Ser(+)1 of SEQ ID NO:2, amino acids Ala(−)14 to Ser(+)1 of SEQ ID NO:2, amino acids Phe(−)13 to Ser(+)1 of SEQ ID NO:2, amino acids Leu(−)12 to Ser(+)1 of SEQ ID NO:2, amino acids Val(−)11 to Ser(+)1 of SEQ ID NO:2, amino acids Ser(−)10 to Ser(+)1 of SEQ ID NO:2, amino acids Asn(−)9 to Ser(+)1 of SEQ ID NO:2, amino acids Met(−)8 to Ser(+)1 of SEQ ID NO:2, amino acids Leu(−)7 to Ser(+)1 of SEQ ID NO:2, amino acids Leu(−)6 to Ser(+)1 of SEQ ID NO:2, amino acids Ala(−)5 to Ser(+)1 of SEQ ID NO:2, amino acids Glu(−)4 to Ser(+)1 of SEQ ID NO:2, amino acids Ala(−)3 to Ser(+)1 of SEQ ID NO:2, amino acids Tyr(−)2 to Ser(+)1 of SEQ ID NO:2, and amino acids Gly(−)1 to Ser(+)1 of SEQ ID NO:2 can be added or fused to the N-terminus of each deletion construct listed above.

The invention also provides polypeptides having one or more amino acids deleted from both the amino and the carboxyl termini of the protease domain of t-PALP, which may be described generally as having residues $n^4$–$m^4$ of SEQ ID NO:2, where $n^4$ and $m^4$ are integers as described above.

Also included are a nucleotide sequence encoding a polypeptide consisting of a portion of the complete t-PALP amino acid sequence encoded by the cDNA clone contained in ATCC Deposit No. 209023, where this portion excludes any integer of amino acid residues from 1 to about 178 amino acids from the amino terminus of the complete amino acid sequence encoded by the cDNA clone contained in ATCC Deposit No. 209023, or any integer of amino acid residues from 1 to about 178 amino acids from the carboxy terminus, or any combination of the above amino terminal and carboxy terminal deletions, of the complete amino acid sequence encoded by the cDNA clone contained in ATCC Deposit No. 209023. Polynucleotides encoding all of the above deletion mutant polypeptide forms also are provided.

The present application is also directed to proteins containing polypeptides at least 90%, 95%, 96%, 97%, 98% or 99% identical to the t-PALP polypeptide sequence set forth herein according to the formula $m^4$–$n^4$. In preferred embodiments, the application is directed to proteins containing polypeptides at least 90%, 95%, 96%, 97%, 98% or 99% identical to polypeptides having the amino acid sequence of the specific t-PALP N- and C-terminal deletions recited herein. Polynucleotides encoding these polypeptides are also encompassed by the invention.

The present application is also directed to proteins containing polypeptides at least 90%, 95%, 96%, 97%, 98% or 99% identical to the t-PALP polypeptide sequence set forth herein according to the formulae m–n, n–m, $n^1$–$m^1$, $n^2$–$m^2$, $n^3$–$m^3$, and/or $n^4$–$m^4$. In preferred embodiments, the application is directed to proteins containing polypeptides at least 90%, 95%, 96%, 97%, 98% or 99% identical to polypeptides having the amino acid sequence of the specific t-PALP N- and C-terminal deletions recited herein. Polynucleotides encoding these polypeptides are also encompassed by the invention.

In the present invention, a "polypeptide fragment" refers to an amino acid sequence which is a portion of that contained in SEQ ID NO:2 or encoded by the cDNA contained in the deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number (–)21–(–)1, 1–20, 21–40, 41–60, 61–80, 81–100, 102–120, 121–140, 141–160, 161–180, 181–200, 201–220, or 221 to the end of the coding region (as numbered in SEQ ID NO:2). Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (6, 5, 4, 3, 2, or 1) amino acids, at either extreme or at both extremes. Polynucleotides encoding these polypeptides are also encompassed by the invention.

Even if deletion of one or more amino acids from the N-terminus of a protein results in modification of loss of one or more biological functions of the protein, other functional activities (e.g., biological activities, ability to multimerize, ability to bind t-PALP receptor) may still be retained. For example, the ability of shortened t-PALP muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a t-PALP mutein with a large number of deleted N-terminal amino acid residues may retain some biological or immunogenic activities. In fact, peptides composed of as few as six t-PALP amino acid residues may often evoke an immune response.

Preferred polypeptide fragments include the secreted protein as well as the mature form, the kringle domain, and/or the protease domain. Further preferred polypeptide fragments include the secreted protein, the mature form, the kringle domain, and/or the protease domain having a continuous series of deleted residues from the amino or the carboxy terminus, or both. For example, any number of amino acids, ranging from 1 to 85, can be deleted from the amino terminus of either the secreted t-PALP polypeptide or the mature form. Similarly, any number of amino acids, ranging from 1–200, can be deleted from the carboxy terminus of the secreted t-PALP protein or mature form. Furthermore, any combination of the above amino and carboxy terminus deletions are preferred. Similarly, polynucleotides encoding these polypeptide fragments are also preferred.

The functional activity of t-PALP polypeptides, and fragments, variants derivatives, and analogs thereof, can be assayed by various methods.

For example, in one embodiment where one is assaying for the ability to bind or compete with full-length t-PALP polypeptide for binding to anti-t-PALP antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a t-PALP ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of t-PALP binding to its substrates (signal transduction) can be assayed.

In addition, assays described herein (see Examples) and otherwise known in the art may routinely be applied to measure the ability of t-PALP polypeptides and fragments, variants derivatives and analogs thereof to elicit t-PALP related biological activity (either in vitro or in vivo). Other methods will be known to the skilled artisan and are within the scope of the invention.

Among the especially preferred fragments of the invention are fragments characterized by structural or functional attributes of t-PALP. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) t-PALP (SEQ ID NO:2). Certain preferred regions are those set out in FIG. 3 and include, but are not limited to, regions of the aforementioned types identified by analysis of the amino acid sequence depicted in FIGS. 1A, 1B, and 1C (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of t-PALP. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of t-PALP.

The data representing the structural or functional attributes of t-PALP set forth in FIGS. 1A, 1B, and 1C and/or Table I, as described above, was generated using the various modules and algorithms of the DNA*STAR set on default parameters. In a preferred embodiment, the data presented in columns VIII, IX, XIII, and XIV of Table I can be used to determine regions of t-PALP which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIGS. 1A, 1B, and 1C. As set out in FIG. 3 and in Table 1, such preferred regions include Gamier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Among highly preferred fragments in this regard are those that comprise regions of t-PALP that combine several structural features, such as several of the features set out above.

Other preferred polypeptide fragments are biologically active t-PALP fragments. Biologically active fragments are those exhibiting activity similar, but not necessarily identical, to an activity of the t-PALP polypeptide. The biological activity of the fragments may include an improved desired activity, or a decreased undesirable activity. Polynucleotides encoding these polypeptide fragments are also encompassed by the invention.

However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2315 of SEQ ID NO:1, b is an integer of 15 to 2329 where both a and b correspond to the positions of nucleotide residues shown in SEQ ID NO:1, and where the b is greater than or equal to a +14.

Other Mutants

In addition to terminal deletion forms of the protein discussed above, it also will be recognized by one of ordinary skill in the art that some amino acid sequences of the t-PALP polypeptide can be varied without significant effect of the structure or function of the protein. If such differences in sequence are contemplated, it should be remembered that there will be critical areas on the protein which determine activity.

Thus, the invention further includes variations of the t-PALP polypeptide which show substantial t-PALP polypeptide activity or which include regions of t-PALP protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the t-PALP of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 2).

TABLE 2

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the t-PALP protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).

A number of mutagenesis studies have been performed on the related t-PA polypeptide. The t-PA fibrin-binding activity has been mapped to the amino-terminal finger and EGF domains (Kalyan, N. K., et al., *J. Biol. Chem.* 263:3971–3978; 1988). In addition, in vivo clearance rates have also been mapped to the finger domain of t-PA (Ahern, T. J., et al., *J. Biol. Chem.* 265:5540–5545; 1990) Other studies by Yahara and colleagues (*Thromb. and Haem.*

72(6):893–899; 1994) report an in vivo clearance activity to be located not only in the finger domain, but also in the kringle domain of t-PA. Several mutations were identified in the protease domain which affected t-PA protease activity (Paoni, N. F., et al., *Prot. Eng.* 5:259–266; 1992). Fibrinolytic activity of t-PA was found to be reduced by mutation of one or more highly conserved amino acid residues in the kringle domains (Markland, W., et al., *Prot. Eng.* 3:117–125; 1989). A key study published by Haigwood and colleagues (Prot. Eng. 2:611–620; 1989) provided a detailed analysis of the effects of various insertion, deletion, and substitution mutations on the various activities of the t-PA molecule. The study determined that (1) variants with carbohydrate-depleted kringle domains possessed higher specific activities than wild-type t-PA, (2) a cleavage site variant substituted at Arg275 with Gly had greatly reduced specific activity, (3) two variants substituted at Lys277 exhibited altered interactions with plasminogen activator inhibitor (PAI)-2, (4) the variant with a truncated carboxy-terminus had reduced activity in the absence of fibrin, and (5) no variants had significantly altered half-lives. A molecular biologist skilled in the techniques of protein mutagenesis would infer from these and other studies that, since the various activities of t-PA may be altered by the introduction of various mutations into the molecule, that, by inference, it may be possible to also target specific mutations to the t-PALP molecule in an effort to reproduce similar changes in t-PALP activities. Since t-PALP is a member of the t-PA-related protein family, to modulate rather than completely eliminate biological activities of t-PALP, preferably mutations are made in sequences encoding amino acids in the t-PALP conserved kringle domain, i.e., in positions 4 to 63 of SEQ ID NO:2, more preferably in residues within this region which are not conserved in all members of the t-PA-related protein family. Similarly, preferable mutations are made in sequences encoding amino acids in the t-PALP conserved protease domain, i.e., in positions 64 to 242 of SEQ ID NO:2, more preferably in residues within this region which are not conserved in all members of the t-PA-related protein family. Also forming part of the present invention are isolated polynucleotides comprising nucleic acid sequences which encode the above t-PALP mutants.

The polypeptides of the present invention are preferably provided in an isolated form, and preferably are substantially purified. A recombinantly produced version of the t-PALP polypeptide can be substantially purified by the one-step method described by Smith and Johnson (*Gene* 67:31–40; 1988). Polypeptides of the invention also can be purified from natural or recombinant sources using anti-t-PALP antibodies of the invention in methods which are well known in the art of protein purification.

The invention further provides an isolated t-PALP polypeptide comprising an amino acid sequence selected from the group consisting of: (a) the amino acid sequence of the full-length t-PALP polypeptide having the complete amino acid sequence shown in SEQ ID NO:2 excepting the N-terminal methionine (i.e., positions −20 to 242 of SEQ ID NO:2) or the complete amino acid sequence excepting the N-terminal methionine encoded by the cDNA clone contained in the ATCC Deposit No. 209023; (b) the amino acid sequence comprising the predicted mature form of the t-PALP polypeptide having the amino acid sequence at positions 1 to 242 in SEQ ID NO:2 or as encoded by the cDNA clone contained in the ATCC Deposit No. 209023; (c) the amino acid sequence comprising the predicted kringle domain of the t-PALP polypeptide having the amino acid sequence at positions 4 to 63 in SEQ ID NO:2 or as encoded by the cDNA clone contained in the ATCC Deposit No. 209023; and (d) the amino acid sequence comprising the predicted protease domain of the t-PALP polypeptide having the amino acid sequence at positions 64 to 242 in SEQ ID NO:2 or as encoded by the cDNA clone contained in the ATCC Deposit No. 209023. The polypeptides of the present invention also include polypeptides having an amino acid sequence at least 80% identical (or 20% different), more preferably at least 90% identical (or 10% different), and still more preferably 95%, 96%, 97%, 98% or 99% identical to (or 5%, 4%, 3%, 2% or 1% different from) those described in (a), (b), (c) or (d) above, as well as polypeptides having an amino acid sequence with at least 90% similarity, and more preferably at least 95% similarity, to those above.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a t-PALP polypeptide is intended that the amino acid sequence of the polypeptide is identical to the reference sequence except that the polypeptide sequence may include up to five amino acid alterations per each 100 amino acids of the reference amino acid of the t-PALP polypeptide. In other words, to obtain a polypeptide having an amino acid sequence at least 95% identical to (or 5% different from) a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2, the amino acid sequence encoded by the deposited plasmid DNA HMS1B42 (ATCC Accession No. 209023), or fragments thereof, or, for instance, to the amino acid sequence shown in FIG. 1 (SEQ ID NO:2), the amino acid sequence encoded by the deposited cDNA clone HMS1B42 (ATCC Accession No. 209023), or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

A further embodiment of the invention relates to a peptide or polypeptide which comprises the amino acid sequence of a t-PALP polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a peptide or polypeptide to have an amino acid sequence which comprises the amino acid sequence of a t-PALP polypeptide, which contains at least one, but not more than 10, 9, 8, 7, 6, 5, 4, 3, 2 or 1 conservative amino acid substitutions.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting t-PALP protein expression as described below or as agonists and antagonists capable of enhancing or inhibiting t-PALP protein function. Further, such polypeptides can be used in the yeast two-hybrid system to "capture" t-PALP protein binding proteins which are also candidate agonists and antagonists according to the present invention. The yeast two hybrid system is described in Fields and Song, Nature 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," *Science,* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate t-PALP-specific antibodies include: a polypeptide comprising amino acid residues from about Ser-1 to about His-10 in SEQ ID NO:2; about Glu-14 to about Leu-23 in SEQ ID NO:2; about Arg-50 to about Trp-60 in SEQ ID NO:2; about Pro-70 to about Gln-86 in SEQ ID NO:2; about Ala-98 to about Val-107 in SEQ ID NO:2; about Leu-117 to about Gln-126 in SEQ ID NO:2; about Arg-134 to about Gly-146 in SEQ ID NO:2; about Ser-172 to about Gln-182 in SEQ ID NO:2; about Gln-185 to about Arg-194 in SEQ ID NO:2; about Thr-206 to about Val-216 in SEQ ID NO:2; and about Thr-222 to about Thr-231 in SEQ ID NO:2; These polypeptide fragments have been determined to bear antigenic epitopes of the t-PALP protein by the analysis of the Jameson-Wolf antigenic index, as shown in FIG. 3, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The present invention is also directed to polypeptide fragments comprising, or alternatively consisting of, an epitope of the polypeptide sequence shown in SEQ ID NO:2, or the polypeptide sequence encoded by the cDNA contained in a deposited clone. Polynucleotides encoding these epitopes (such as, for example, the sequence disclosed in SEQ ID NO:1) are also encompassed by the invention, as is the nucleotide sequences of the complementary strand of the polynucleotides encoding these epitopes. And polynucleotides which hybridize to the complementary strand under stringent hybridization conditions or lower stringency conditions.

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least 4, at least 5, at least 6, at least 7, more preferably at least 8, at least 9, at least 10, at least 15, at least 20, at least 25, and most preferably between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. (See, for instance, Wilson et al., Cell 37:767–778 (1984); Sutcliffe et al., Science 219:660–666 (1983).)

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al., Nature, 331:84–86 (1988). Fusion proteins that have a disulfide-linked dimeric structure due to the IgG portion can also be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag to aid in detection and purification of the expressed polypeptide.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides corresponding to SEQ ID NO:2 thereby effectively generating agonists and antagonists of the polypeptides. See, generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S., Trends Biotechnol. 16(2):76–82 (1998); Hansson, L. O., et al., J. Mol. Biol. 287:265–76 (1999); and Lorenzo, M. M. and Blasco, R., Biotechniques 24(2):308–13 (1998) (each of these patents and publications are hereby incorporated by reference). In one embodiment, alteration of polynucleotides corresponding to SEQ ID NO:1 and corresponding polypeptides may be achieved by DNA shuffling. DNA shuffling involves the assembly of two or more DNA segments into a desired molecule corresponding to SEQ ID NO:1 polynucleotides of the invention by homologous, or site-specific, recombination. In another embodiment, polynucleotides corresponding to SEQ ID NO:1 and corresponding polypeptides may be altered by being subjected to random mutagenesis by error-prone PCR, random nucleotide insertion or other methods prior to recombination. In another embodiment, one or more components, motifs, sections, parts, domains, fragments, etc., of coding polynucleotide corresponding to SEQ ID NO:1, or the polypeptide encoded thereby may be recombined with one or more components, motifs, sections, parts, domains, fragments, etc. of one or more heterologous molecules.

Fusion Proteins

As one of skill in the art will appreciate, t-PALP polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric t-PALP protein or protein fragment alone (Fountoulakis et al., J. Biochem. 270:3958–3964 (1995)).

Any t-PALP polypeptide can be used to generate fusion proteins. For example, the t-PALP polypeptide, when fused to a second protein, can be used as an antigenic tag. Antibodies raised against the t-PALP polypeptide can be used to indirectly detect the second protein by binding to the t-PALP. Moreover, because secreted proteins target cellular locations based on trafficking signals, the t-PALP polypeptides can be used as targeting molecules once fused to other proteins.

Examples of domains that can be fused to t-PALP polypeptides include not only heterologous signal sequences, but also other heterologous functional regions. The fusion does not necessarily need to be direct, but may occur through linker sequences.

In certain preferred embodiments, t-PALP proteins of the invention comprise fusion proteins wherein the t-PALP polypeptides are those described above as $n^1$–$m^1$, $n^2$–$m^2$, $n^3$–$m^3$, $n^4$–$m^4$. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Moreover, fusion proteins may also be engineered to improve characteristics of the t-PALP polypeptide. For instance, a region of additional amino acids, particularly charged amino acids, may be added to the N-terminus of the t-PALP polypeptide to improve stability and persistence during purification from the host cell or subsequent handling and storage. Also, peptide moieties may be added to the t-PALP polypeptide to facilitate purification. Such regions may be removed prior to final preparation of the t-PALP polypeptide. The addition of peptide moieties to facilitate handling of polypeptides are familiar and routine techniques in the art.

As one of skill in the art will appreciate, polypeptides of the present invention and the epitope-bearing fragments thereof described above, can be combined with heterologous polypeptide sequences. For example, the polypeptides of the present invention may be fused with heterologous polypeptide sequences, for example, the polypeptides of the present invention may be fused with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the t-PALP polypeptides can be fused to marker sequences, such as a peptide which facilitates purification of t-PALP. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the t-PALP polynucleotides or the polypeptides.

Antibodies t-PALP-protein specific antibodies for use in the present invention can be raised against the intact t-PALP protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to t-PALP protein. Fab and F(ab')2 fragments lack the Fc fragment of intact antibody, clear more rapidly from the circulation, and may have less non-specific tissue binding of an intact antibody (Wahl et al., *J Nucl. Med.* 24:316–325 (1983)). Thus, these fragments are preferred.

The antibodies of the present invention may be prepared by any of a variety of methods. For example, cells expressing the t-PALP protein or an antigenic fragment thereof can be administered to an animal in order to induce the production of sera containing polyclonal antibodies. In a preferred method, a preparation of t-PALP protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or t-PALP protein binding fragments thereof). Such monoclonal antibodies can be prepared using hybridoma technology (Kohler et al.,

*Nature* 256:495 (1975); Köhler et al., *Eur. J. Immunol.* 6:511 (1976); Kohler et al., Eur. J. Immunol. 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a t-PALP protein antigen or, more preferably, with a t-PALP protein-expressing cell. Suitable cells can be recognized by their capacity to bind anti-t-PALP protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the t-PALP protein antigen.

Alternatively, additional antibodies capable of binding to the t-PALP protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, t-PALP-protein specific antibodies are used to immunize an animal, preferably a mouse. The splenocytes of such an animal are then used to produce hybridoma cells, and the hybridoma cells are screened to identify clones which produce an antibody whose ability to bind to the t-PALP protein-specific antibody can be blocked by the t-PALP protein antigen. Such antibodies comprise anti-idiotypic antibodies to the t-PALP protein-specific antibody and can be used to immunize an animal to induce formation of further t-PALP protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, t-PALP protein-binding fragments can be produced through the application of recombinant DNA technology or through synthetic chemistry.

For in vivo use of anti-t-PALP in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and human polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, et al., J. Immunol. 147:60–69 (1991); U.S. Pat. Nos. 5,573,920, 4,474,893, 5,601,819, 4,714,681, 4,925,648; Kostelny et al., J. Immunol. 148:1547–1553 (1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $10^{-9}$M, 5×

$10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu, L. et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura et al., Immunol. Lett. 39:91–99 (1994); U.S. Pat. No. 5,474,981; Gillies et al., PNAS 89:1428–1432 (1992); Fell et al., J.

Immunol. 146:2446–2452(1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi et al., PNAS 88:10535–10539 (1991); Zheng et al., J. Immunol. 154:5590–5600 (1995); and Vil et al., PNAS 89:11337–11341(1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng et al., Blood 92(6):1981–1988 (1998); Chen, et al., Cancer Res. 58(16):3668–3678 (1998); Harrop et al., J. Immunol. 161(4):1786–1794 (1998); Zhu et al., Cancer Res. 58(15):3209–3214 (1998); Yoon, et al., J. Immunol. 160(7):3170–3179 (1998); Prat et al., J. Cell. Sci. 111(Pt2):237–247 (1998); Pitard et al., J. Immunol. Methods 205(2):177–190 (1997); Liautard et al., Cytokinde 9(4): 233–241 (1997); Carlson et al., J. Biol. Chem. 272(17): 11295–11301 (1997); Taryman et al., Neuron 14(4):755–762 (1995); Muller et al., Structure 6(9):1153–1167 (1998); Bartunek et al., Cytokine 8(1):14–20 (1996) (said references incorporated by reference in their entireties).

As discussed above, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to ligand can be used to generate anti-idiotypes that "mimic" the polypeptide mutimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The invention further relates to a diagnostic kit for use in screening serum containing antibodies specific against proliferative and/or cancerous polynucleotides and polypeptides. Such a kit may include a substantially isolated polypeptide antigen comprising an epitope which is specifically immunoreactive with at least one anti-polypeptide antigen antibody. Such a kit also includes means for detecting the binding of said antibody to the antigen. In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labelled anti-human antibody. In this embodiment, binding of the antibody to the polypeptide antigen can be detected by binding of the said reporter-labelled antibody.

The invention further includes a method of detecting proliferative and/or cancerous disorders and conditions in a test subject. This detection method includes reacting serum from a test subject (e.g. one in which proliferative and/or cancerous cells or tissues may be present) with a substantially isolated polypeptide and/or polynucleotide antigen, and examining the antigen for the presence of bound antibody. In a specific embodiment, the method includes a polypeptide antigen attached to a solid support, and the serum is reacted with the support. Subsequently, the support is reacted with a reporter labelled anti-human antibody. The solid support is then examined for the presence of reporter-labelled antibody.

Additionally, the invention includes a proliferative condition vaccine composition. The composition includes a substantially isolated polypeptide and/or polynucleotide antigen, where the antigen includes an epitope which is specifically immunoreactive with at least antibody specific for the epitope. The peptide and/or polynucleotide antigen may be produced according to methods known in the art, including recombinant expression or chemical synthesis. The peptide antigen is preferably present in a pharmacologically effective dose in a pharmaceutically acceptable carrier.

Further, the invention includes a monoclonal antibody that is specifically immunoreactive with polypeptide and/or polynucleotide epitopes. The invention includes a substantially isolated preparation of polyclonal antibodies specifically immunoreactive with polynucleotides and/or polypeptides of the present invention. In a more specific embodiment, such polyclonal antibodies are prepared by affinity chromatography, in addition to, other methods known in the art.

In another embodiment, the invention includes a method for producing antibodies to polypeptide and/or polynucleotide antigens. The method includes administering to a test subject a substantially isolated polypeptide and/or polynucleotide antigen, where the antigen includes an epitope which is specifically immunoreactive with at least one anti-polypeptide and/or polynucleotide antibody. The antigen is administered in an amount sufficient to produce an immune response in the subject.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labelled monoclonal antibody. Alternatively, or in addition, the detecting means may include a labelled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labelled anti-human antibody to bind reporter to the reagent in proportion to the amount of bound anti-antigen antibody on the solid support. The reagent is again washed to remove unbound labelled antibody, and the amount of reporter associated with the reagent is determined. Typically, the reporter is an enzyme which is detected by incubating the solid phase in the presence of a suitable fluorometric or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labelled anti-human antibody for detecting surface-bound anti-antigen antibody.

Circulatory System-Related Disorders

Diagnosis

The present inventors have discovered that t-PALP is expressed in activated monocytes. For a number of circulatory system-related disorders, substantially altered (increased or decreased) levels of t-PALP gene expression can be detected in circulatory system tissue or other cells or bodily fluids (e.g., sera, plasma, urine, synovial fluid or spinal fluid) taken from an individual having such a disorder, relative to a "standard" t-PALP gene expression level, that is, the t-PALP expression level in circulatory system tissues or bodily fluids from an individual not having the circulatory system disorder. Thus, the invention provides a diagnostic method useful during diagnosis of a circulatory system disorder, which involves measuring the expression level of the gene encoding the t-PALP protein in circulatory system tissue or other cells or body fluid from an individual and comparing the measured gene expression level with a standard t-PALP gene expression level, whereby an increase or decrease in the gene expression level compared to the standard is indicative of an circulatory system disorder.

In particular, it is believed that certain tissues in mammals with cancers of the circulatory system express significantly reduced levels of the t-PALP protein and mRNA encoding the t-PALP protein when compared to a corresponding "standard" level. Further, it is believed that altered levels of the t-PALP protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a circulatory system disorder, including cancers of this system, which involves measuring the expression level of the gene encoding the t-PALP protein in the circulatory system tissue or other cells or body fluid from an individual and comparing the measured gene expression level with a standard t-PALP gene expression level, whereby an increase or decrease in the gene expression level compared to the standard is indicative of a circulatory system disorder.

Where a diagnosis of a disorder in the circulatory system including diagnosis of a cancer has already been made according to conventional methods, the present invention is useful as a prognostic indicator, whereby patients exhibiting enhanced or depressed t-PALP gene expression will experience a worse clinical outcome relative to patients expressing the gene at a level nearer the standard level.

By "assaying the expression level of the gene encoding the t-PALP protein" is intended qualitatively or quantitatively measuring or estimating the level of the t-PALP protein or the level of the mRNA encoding the t-PALP protein in a first biological sample either directly (e.g., by determining or estimating absolute protein level or mRNA level) or relatively (e.g., by comparing to the t-PALP protein level or mRNA level in a second biological sample). Preferably, the t-PALP protein level or mRNA level in the first biological sample is measured or estimated and compared to a standard t-PALP protein level or mRNA level, the standard being taken from a second biological sample obtained from an individual not having the disorder or being determined by averaging levels from a population of individuals not having a disorder of the circulatory system. As will be appreciated in the art, once a standard t-PALP protein level or mRNA level is known, it can be used repeatedly as a standard for comparison.

By "biological sample" is intended any biological sample obtained from an individual, body fluid, cell line, tissue culture, or other source which contains t-PALP protein or mRNA. As indicated, biological samples include body fluids (such as sera, plasma, urine, synovial fluid and spinal fluid) which contain free t-PALP protein, circulatory system tissue, and other tissue sources found to express complete or mature t-PALP or a t-PALP receptor. Methods for obtaining tissue biopsies and body fluids from mammals are well known in the art. Where the biological sample is to include mRNA, a tissue biopsy is the preferred source.

The present invention is useful for diagnosis or treatment of various circulatory system-related disorders in mammals, preferably humans. Such disorders include any disregulation of circulatory cell function including, but not limited to, diseases related to thrombosis, which is characterized by hypercoagulation of blood cells. t-PALP may be employed to prevent proximal extension of deep-venous thrombosis or the recurrence of pulmonary embolisms, which are characterized by lodging of a blood clot in a pulmonary artery with subsequent obstruction of blood supply to the lung parenchyma. t-PALP may also be employed to help prevent the recurrence of cerebral or other systemic embolisms. The enzyme of the present invention may also be used to treat high risk patients, such as those who have congestive heart failure, acute myocardial infarction or cardiomyopathy to prevent the development of deep-vein thrombosis or pulmonary embolism. t-PALP may also be employed as a long-term therapy for the occasional patient who has recurrent thrombosis or embolism while on the drug Warfarin.

Total cellular RNA can be isolated from a biological sample using any suitable technique such as the single-step guanidinium-thiocyanate-phenol-chloroform method described in Chomczynski and Sacchi, *Anal. Biochem.* 162: 156–159 (1987). Levels of mRNA encoding the t-PALP protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying t-PALP protein levels in a biological sample can occur using antibody-based techniques. For example, t-PALP protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting t-PALP protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying t-PALP protein levels in a biological sample obtained from an individual, t-PALP protein can also be detected in vivo by imaging. Antibody labels or markers for in vivo imaging of t-PALP protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A t-PALP protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain t-PALP protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

As noted above, t-PALP polynucleotides and polypeptides are useful for diagnosis of conditions involving abnormally high or low expression of t-PALP activities. Given the cells and tissues where t-PALP is expressed as well as the activities modulated by t-PALP, it is readily apparent that a substantially altered (increased or decreased) level of expression of t-PALP in an individual compared to the standard or "normal" level produces pathological conditions related to the bodily system(s) in which t-PALP is expressed and/or is active.

It will also be appreciated by one of ordinary skill that, since the t-PALP protein of the invention is related to t-PA the mature secreted form of the protein may be released in soluble form from the cells which express the t-PALP by proteolytic cleavage. Therefore, when t-PALP mature form is added from an exogenous source to cells, tissues or the body of an individual, the protein will exert its physiological activities on its target cells of that individual.

Therefore, it will be appreciated that conditions caused by a decrease in the standard or normal level of t-PALP activity in an individual, particularly disorders of the circulatory system, can be treated by administration of t-PALP polypeptide (in the form of the mature, secreted protein). Thus, the invention also provides a method of treatment of an individual in need of an increased level of t-PALP activity comprising administering to such an individual a pharmaceutical composition comprising an amount of an isolated t-PALP polypeptide of the invention, particularly a mature form of the t-PALP protein of the invention, effective to increase the t-PALP activity level in such an individual.

t-PALP may also be employed in combinations, compositions, and methods for treating thrombic disease. For example, the enzyme of the present invention may be combined with a thrombolytic agent to work in a complementary fashion to dissolve blood clots, resulting in decreased reperfusion times and increased reocclusion times in patients. The thrombolytic agent dissolves the clot while t-PALP prevents thrombin from regenerating the clot. This combination allows the administration of a thrombolytic agent at a considerably lower dosage than if given alone, therefore, allowing the prevention of undesirable side-effects associated with the use of a high level of thrombolytic agent, for example, bleeding complications.

Formulations

The t-PALP polypeptide composition will be formulated and dosed in a fashion consistent with good medical practice, taking into account the clinical condition of the individual patient (especially the side effects of treatment with t-PALP polypeptide alone), the site of delivery of the t-PALP polypeptide composition, the method of administration, the scheduling of administration, and other factors known to practitioners. The "effective amount" of t-PALP polypeptide for purposes herein is thus determined by such considerations.

As a general proposition, the total pharmaceutically effective amount of t-PALP polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the t-PALP polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the t-PALP of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The t-PALP polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release t-PALP polypeptide compositions also include liposomally entrapped t-PALP polypeptide. Liposomes containing t-PALP polypeptide are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal t-PALP polypeptide therapy.

For parenteral administration, in one embodiment, the t-PALP polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the t-PALP polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The t-PALP polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of t-PALP polypeptide salts.

t-PALP polypeptide to be used for therapeutic administration must be sterile. Sterility is readily accomplished by filtration through sterile filtration membranes (e.g., 0.2 micron membranes). Therapeutic t-PALP polypeptide compositions generally are placed into a container having a sterile access port, for example, an intravenous solution bag or vial having a stopper pierceable by a hypodermic injection needle.

t-PALP polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous t-PALP polypeptide solution, and the resulting mixture is lyophilized. The infusion solution is prepared by reconstituting the lyophilized t-PALP polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of t-PALP on cells, such as its interaction with t-PALP-binding molecules. An agonist is a compound which increases the natural biological functions of t-PALP or which functions in a manner similar to t-PALP, while antagonists decrease or eliminate such functions.

In another aspect of this embodiment the invention provides a method for identifying a protein which binds specifically to a t-PALP polypeptide. For example, the t-PALP polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds t-PALP. The preparation is incubated with labeled t-PALP in the absence or the presence of a candidate molecule which may be a t-PALP agonist or antagonist. The ability of the candidate molecule to bind the binding molecule is reflected in decreased binding of the labeled ligand. Molecules which bind gratuitously, i.e., without inducing the effects of t-PALP on binding the t-PALP binding molecule, are most likely to be good antagonists. Molecules that bind well and elicit effects that are the same as or closely related to t-PALP are agonists.

t-PALP-like effects of potential agonists and antagonists may by measured, for instance, by determining activity of a second messenger system following interaction of the candidate molecule with a cell or appropriate cell preparation, and comparing the effect with that of t-PALP or molecules that elicit the same effects as t-PALP. Second messenger systems that may be useful in this regard include but are not limited to AMP guanylate cyclase, ion channel or phosphoinositide hydrolysis second messenger systems.

Another example of an assay for t-PALP antagonists is a competitive assay that combines t-PALP and a potential antagonist with recombinant t-PALP receptor molecules under appropriate conditions for a competitive inhibition assay. t-PALP can be labeled, such as by radioactivity, such that the number of t-PALP molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing t-PALP-induced activities, thereby preventing the action of t-PALP by excluding t-PALP from binding.

Other potential antagonists include antisense molecules. Antisense technology can be used to control gene expression through antisense DNA or RNA or through triple-helix formation. Antisense techniques are discussed, for example, in Okano, *J. Neurochem.* 56: 560 (1991); "Oligodeoxynucleotides as Antisense Inhibitors of Gene Expression." CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of t-PALP. The antisense RNA oligonucleotide hybridizes to the mRNA in vivo and blocks translation of the mRNA molecule into t-PALP polypeptide. The oligonucleotides described above can also be delivered to cells such that the antisense RNA or DNA may be expressed in vivo to inhibit production of t-PALP protein.

The agonists and antagonists may be employed in a composition with a pharmaceutically acceptable carrier, e.g., as described above.

The antagonists may be employed for instance to inhibit t-PALP activities such as fibrin binding. By inhibition of fibrin binding, a t-PALP antagonist may decrease the efficacy of t-PALP enzymatic activity. Such an inhibition may of interest if it is desirable to negatively alter t-PALP activity in an indirect manner. Rather than directly targeting the active site of the t-PALP enzyme, it may be of interest to alter the activity of the enzyme by targeting its fibrin-binding activity. Furthermore, t-PALP may be of use in regulating the proteolytic activity plasminogen. An antagonist which functions by directly binding to the t-PALP active site may reduce the local concentration of functional plasminogen in a given system. Such a capability may desired as an effective means of ameliorating a current treatment procedure which has artificially increased the effective concentration of plasminogen. In addition, the use of such a t-PALP antagonist may be used effectively to treat a system which has a congenitally increased level of t-PALP, and in turn, plasminogen activity. Similarly, antibodies against t-PALP may be employed to bind to and inhibit t-PALP activity to treat the same or a related condition. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a t-PALP protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

Uses of the t-PALP Polynucleotides t-PALP polynucleotides and/or polypeptides of the present invention, and agonists thereof, can be used as anti-angiogenesis, anti-tumorigenesis, and/or anti-cancer agents. As detailed in Examples 40, 52, and 53, t-PALP polynucleotides and polypeptides of the invention were used to inhibit the growth of TSU cells in two different tumor model systems. Despite the high tumorigenicity of TSU cells, treatment with t-PALP of the present invention resulted in a marked inhibition of tumor masses grown on chick embryo chorioallantoic membranes (CAM); see Example 40. Additionally, t-PALP of the present invention also resulted in a marked inhibition on the growth rate of TSU cell xenograft tumors in athymic nude mice (Examples 51 and 52). t-PALP, and/or a mutein thereof, and/or an agonist, and/or an antagonist thereof, of the present invention, can be used to treat a number of cancers including, but not limited to, breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, adenoma, and the like.

The t-PALP polynucleotides identified herein can be used in numerous ways as reagents. The following description should be considered exemplary and utilizes known techniques.

There exists an ongoing need to identify new chromosome markers, since few chromosome marking reagents, based on actual sequence data (repeat polymorphisms), are presently available.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human t-PALP gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the t-PALP polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the t-PALP polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the t-PALP polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the t-PALP polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the t-PALP polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using t-PALP polynucleotides. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31'mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferrably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The US Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°–20° C., vs. 4°–16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative disorders are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative disorders of hematopoietic cells and tissues, in light of the numerous cells and cell types of varying origins which are known to exhibit proliferative phenotypes.

In addition to the foregoing, a t-PALP polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988).

Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

t-PALP polynucleotides are also useful in gene therapy. One goal of gene therapy is to insert a normal gene into an organism having a defective gene, in an effort to correct the genetic defect. t-PALP offers a means of targeting such genetic defects in a highly accurate manner. Another goal is to insert a new gene that was not present in the host genome, thereby producing a new trait in the host cell.

The t-PALP polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The t-PALP polynucleotides can be used as additional DNA markers for RFLP.

The t-PALP polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, t-PALP polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from t-PALP sequences. Panels of such reagents can identify tissue by species and/or by organ type. In a similar fashion, these reagents can be used to screen tissue cultures for contamination.

Because t-PALP is found expressed in cerebellum, smooth muscle, resting and PHA-treated T-cells, GM-CSF-treated macrophages, frontal cortex of the brain, breast lymph node, chronic lymphocytic leukemic spleen, and several other tissues, t-PALP polynucleotides are useful as hybridization probes for differential identification of the tissue(s) or cell type(s) present in a biological sample. Similarly, polypeptides and antibodies directed to t-PALP polypeptides are useful to provide immunological probes for differential identification of the tissue(s) or cell type(s). In addition, for a number of disorders of the above tissues or cells, particularly of the circulatory system, significantly higher or lower levels of t-PALP gene expression may be detected in certain tissues (e.g., cancerous and wounded tissues) or bodily fluids (e.g., serum, plasma, urine, synovial fluid or spinal fluid) taken from an individual having such a disorder, relative to a "standard" t-PALP gene expression level, i.e., the t-PALP expression level in healthy tissue from an individual not having the circulatory system disorder.

Thus, the invention provides a diagnostic method of a disorder, which involves: (a) assaying t-PALP gene expression level in cells or body fluid of an individual; (b) comparing the t-PALP gene expression level with a standard t-PALP gene expression level, whereby an increase or decrease in the assayed t-PALP gene expression level compared to the standard expression level is indicative of a disorder in the circulatory system.

In the very least, the t-PALP polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of t-PALP Polypeptides t-PALP polypeptides can be used in numerous ways. The following description should be considered exemplary and utilizes known techniques.

t-PALP polypeptides can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99 mTc), and fluorescent labels, such as fluorescein and rhodamine, and biotin.

In addition to assaying protein levels in a biological sample, proteins can also be detected in vivo by imaging.

Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of t-PALP polypeptide in cells or body fluid of an individual; (b) comparing the level of gene expression with a standard gene expression level, whereby an increase or decrease in the assayed t-PALP polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, t-PALP polypeptides can be used to treat disease. For example, patients can be administered t-PALP polypeptides in an effort to replace absent or decreased levels of the t-PALP polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to t-PALP polypeptides can also be used to treat disease. For example, administration of an antibody directed to a t-PALP polypeptide can bind and reduce overproduction of the polypeptide. Similarly, administration of an antibody can activate the polypeptide, such as by binding to a polypeptide bound to a membrane (receptor).

At the very least, the t-PALP polypeptides can be used as molecular weight markers on SDS-PAGE gels or on molecular sieve gel filtration columns using methods well known to those of skill in the art. t-PALP polypeptides can also be used to raise antibodies, which in turn are used to measure protein expression from a recombinant cell, as a way of assessing transformation of the host cell. Moreover, t-PALP polypeptides can be used to test the following biological activities.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the t-PALP polypeptide of the present invention. This method requires a polynucleotide which codes for a t-PALP polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a t-PALP polynucleotide ex vivo, with the engineered cells then being provided to a patient to be treated with the polypeptide. Such methods are well-known in the art. For example, see Belldegrun, A., et al., J. Natl. Cancer Inst. 85: 207–216 (1993); Ferrantini, M. et al., Cancer Research 53: 1107–1112 (1993); Ferrantini, M. et al., J. Immunology 153: 4604–4615 (1994); Kaido, T., et al., Int. J. Cancer 60: 221–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the t-PALP polynucleotide constructs can be delivered by any method that delivers injectable materials to the cells of an animal, such as, injection into the interstitial space of tissues (heart, muscle, skin, lung, liver, and the like). The t-PALP polynucleotide constructs may be delivered in a pharmaceutically acceptable liquid or aqueous carrier.

In one embodiment, the t-PALP polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the t-PALP polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The t-PALP polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of t-PALP polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for t-PALP.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The t-PALP polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked t-PALP DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the t-PALP polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255: 10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding t-PALP. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14×, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding t-PALP. Such retroviral vector particles then may be employed, to transduce eukaryotic cells, either in vitro or in vivo. The transduced eukaryotic cells will express t-PALP.

In certain other embodiments, cells are engineered, ex vivo or in vivo, with t-PALP polynucleotide contained in an adenovirus vector. Adenovirus can be manipulated such that it encodes and expresses t-PALP, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis.109: 233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252: 431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Imunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The t-PALP polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the t-PALP polynucleotide construct. These viral particles are then used to transduce eukaryotic cells, either ex vivo or in vivo. The transduced cells will contain the t-PALP polynucleotide construct integrated into its genome, and will express t-PALP.

Another method of gene therapy involves operably associating heterologous control regions and endogenous polynucleotide sequences (e.g. encoding t-PALP) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the t-PALP desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous t-PALP sequence is placed under the control of the promoter. The promoter then drives the expression of the endogenous t-PALP sequence.

The polynucleotides encoding t-PALP may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding t-PALP contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities of t-PALP t-PALP polynucleotides or polypeptides, or agonists or antagonists of t-PALP, can be used in assays to test for one or more biological activities. If t-PALP polynucleotides or polypeptides, or agonists or antagonists of t-PALP, do exhibit activity in a particular assay, it is likely that t-PALP may be involved in the diseases associated with the biological activity. Therefore, t-PALP could be used to treat the associated disease.

Immune Activity t-PALP polynucleotides or polypeptides, or agonists or antagonists of t-PALP, may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, t-PALP polynucleotides or polypeptides, or agonists or antagonists of t-PALP, can be used as a marker or detector of a particular immune system disease or disorder.

t-PALP polynucleotides or polypeptides, or agonists or antagonists of t-PALP, may be useful in treating or detecting deficiencies or disorders of hematopoietic cells. t-PALP polynucleotides or polypeptides, or agonists or antagonists of t-PALP, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, t-PALP polynucleotides or polypeptides, or agonists or antagonists of t-PALP, can also be used to modulate hemostatic (the stopping of bleeding) or thrombolytic activity (clot formation). For example, by increasing hemostatic or thrombolytic activity, t-PALP polynucleotides or polypeptides, or agonists or antagonists of t-PALP, could be used to treat blood coagulation disorders (e.g., afibrinogenemia, factor deficiencies), blood platelet disorders (e.g. thrombocytopenia), or wounds resulting from trauma, surgery, or other causes. Alternatively, t-PALP polynucleotides or polypeptides, or agonists or antagonists of t-PALP, that can decrease hemostatic or thrombolytic activity could be used to inhibit or dissolve clotting. These molecules could be important in the treatment of heart attacks (infarction), strokes, or scarring.

t-PALP polynucleotides or polypeptides, or agonists or antagonists of t-PALP, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of t-PALP polynucleotides or polypeptides, or agonists or antagonists of t-PALP, that can inhibit an immune response, particularly the proliferation, differentiation, or chemotaxis of T-cells, may be an effective therapy in preventing autoimmune disorders.

Examples of autoimmune disorders that can be treated or detected include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by t-PALP polynucleotides or polypeptides, or agonists or antagonists of t-PALP. Moreover, these molecules can be used to treat anaphylaxis, hypersensitivity to an antigenic molecule, or blood group incompatibility.

t-PALP polynucleotides or polypeptides, or agonists or antagonists of t-PALP, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of t-PALP polynucleotides or polypeptides, or agonists or antagonists of t-PALP, that inhibits an immune response, particularly the proliferation, differentiation, or chemotaxis of T-cells, may be an effective therapy in preventing organ rejection or GVHD.

Similarly, t-PALP polynucleotides or polypeptides, or agonists or antagonists of t-PALP, may also be used to modulate inflammation. For example, t-PALP polynucleotides or polypeptides, or agonists or antagonists of t-PALP, may inhibit the proliferation and differentiation of cells involved in an inflammatory response. These molecules can be used to treat inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders t-PALP polynucleotides or polypeptides, or agonists or antagonists of t-PALP, can be used to treat or detect hyperproliferative disorders, including neoplasms. t-PALP polynucleotides or polypeptides, or agonists or antagonists of t-PALP, may inhibit the proliferation of the disorder through direct or indirect interactions. Alternatively, t-PALP polynucleotides or polypeptides, or agonists or antagonists of t-PALP, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by t-PALP polynucleotides or polypeptides, or agonists or antagonists of t-PALP, include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by t-PALP polynucleotides or polypeptides, or agonists or antagonists of t-PALP. Examples of such hyperproliferative disorders include, but are not limited to:

hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative disorders by inserting into an abnormally proliferating cell a polynucleotide of the present invention, wherein said polynucleotide represses said expression.

Another embodiment of the present invention provides a method of treating cell-proliferative disorders in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more preferrably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described disorders. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation disorders as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragements thereof, of the present invention. Such antibodies, fragments, or regions, will preferably have an affinity for polynucleotides or polypeptides, including fragements thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et. al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses.50(5):423–33 (1998), Chem Biol Interact. April 24;111–112:23–34 (1998), J Mol Med.76(6):402–12 (1998), Int J Tissue React;20(1): 3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol hnmunol 1998;231: 125–41, which is hereby incorporated by reference). Such thereapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or prodrugs) to targeted cells expressing the polypeptide of the present invention. Polypeptides or polypeptide antibodes of the invention may be associated with with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders t-PALP polynucleotides or polypeptides, or agonists or antagonists of t-PALP, encoding t-PALP may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

t-PALP polynucleotides or polypeptides, or agonists or antagonists of t-PALP, are especially effective for the treatment of critical limb ischemia and coronary disease.

t-PALP polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. t-PALP polypeptides may be administered as part of a Therapeutic, described in more detail below. Methods of delivering t-PALP polynucleotides are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.,* 333: 1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat a cancer or tumor. Cancers which may be treated with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, Ocular disorders associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, disorders which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele *minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter “d group” transition metals.

Lighter “d group” transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha, alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate (“GST”; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or “CCA”; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated or detected by t-PALP polynucleotides or polypeptides, as well as antagonists or agonists of t-PALP, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi’s sarcoma and ovarian cancer); autoimmune disorders (such as, multiple sclerosis, Sjogren’s syndrome, Hashimoto’s thyroiditis, biliary cirrhosis, Behcet’s disease, Crohn’s disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, t-PALP polynucleotides, polypeptides, and/or antagonists of the invention are used to inhibit growth, progression, and/or metasis of cancers, in particular those listed above.

Additional diseases or conditions associated with increased cell survival that could be treated or detected by t-PALP polynucleotides or polypeptides, or agonists or antagonists of t-PALP, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin’s disease and non-Hodgkin’s disease), multiple myeloma, Waldenstrom’s macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by t-PALP polynucleotides or polypeptides, as well as agonists or antagonists of t-PALP, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing t-PALP polynucleotides or polypeptides, as well as agonists or antagonists of t-PALP, for therapeutic purposes, for example, to stimulate epithelial cell proliferation and basal keratinocytes for the purpose of wound healing, and to stimulate hair follicle production and healing of dermal wounds. t-PALP polynucleotides or polypeptides, as well as agonists or antagonists of t-PALP, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. t-PALP polynucleotides or polypeptides, as well as agonists or antagonists of t-PALP, could be used to promote dermal reestablishment subsequent to dermal loss t-PALP polynucleotides or polypeptides, as well as agonists or antagonists of t-PALP, could be used to increase the adherence of skin grafts to a wound bed and to stimulate re-epithelialization from the wound bed. The following are types of grafts that t-PALP polynucleotides or polypeptides, agonists or antagonists of t-PALP, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. t-PALP polynucleotides or polypeptides, as well as agonists or antagonists of t-PALP, can be used to promote skin strength and to improve the appearance of aged skin.

It is believed that t-PALP polynucleotides or polypeptides, as well as agonists or antagonists of t-PALP, will also produce changes in hepatocyte proliferation, and epithelial cell proliferation in the lung, breast, pancreas, stomach, small intesting, and large intestine. t-PALP polynucleotides or polypeptides, as well as agonists or antagonists of t-PALP, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. t-PALP polynucleotides or polypeptides, agonists or antagonists of t-PALP, may promote proliferation of endothelial cells, keratinocytes, and basal keratinocytes.

t-PALP polynucleotides or polypeptides, as well as agonists or antagonists of t-PALP, could also be used to reduce the side effects of gut toxicity that result from radiation, chemotherapy treatments or viral infections. t-PALP polynucleotides or polypeptides, as well as agonists or antagonists of t-PALP, may have a cytoprotective effect on the small intestine mucosa. t-PALP polynucleotides or polypeptides, as well as agonists or antagonists of t-PALP, may also stimulate healing of mucositis (mouth ulcers) that result from chemotherapy and viral infections.

t-PALP polynucleotides or polypeptides, as well as agonists or antagonists of t-PALP, could further be used in full regeneration of skin in full and partial thickness skin defects, including burns, (i.e., repopulation of hair follicles, sweat glands, and sebaceous glands), treatment of other skin defects such as psoriasis. t-PALP polynucleotides or polypeptides, as well as agonists or antagonists of t-PALP, could be used to treat epidermolysis bullosa, a defect in adherence of the epidermis to the underlying dermis which results in frequent, open and painful blisters by accelerating reepithelialization of these lesions. t-PALP polynucleotides or polypeptides, as well as agonists or antagonists of t-PALP, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, t-PALP polynucleotides or polypeptides, as well as agonists or antagonists of t-PALP, could be used to promote the resurfacing of the mucosal surface to aid more rapid healing and to prevent progression of inflammatory bowel disease. Treatment with t-PALP polynucleotides or polypeptides, agonists or antagonists of t-PALP, is expected to have a significant effect on the production of mucus throughout the gastrointestinal tract and could be used to protect the intestinal mucosa from injurious substances that are ingested or following surgery. t-PALP polynucleotides or polypeptides, as well as agonists or antagonists of t-PALP, could be used to treat diseases associate with the under expression of t-PALP.

Moreover, t-PALP polynucleotides or polypeptides, as well as agonists or antagonists of t-PALP, could be used to prevent and heal damage to the lungs due to various pathological states. A growth factor such as t-PALP polynucleotides or polypeptides, as well as agonists or antagonists of t-PALP, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using t-PALP polynucleotides or polypeptides, agonists or antagonists of t-PALP. Also, t-PALP polynucleotides or polypeptides, as well as agonists or antagonists of t-PALP, could be used to stimulate the proliferation of and differentiation of type II pneumocytes, which may help treat or prevent disease such as hyaline membrane diseases, such as infant respiratory distress syndrome and bronchopulmonary displasia, in premature infants.

t-PALP polynucleotides or polypeptides, as well as agonists or antagonists of t-PALP, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, t-PALP polynucleotides or polypeptides, as well as agonists or antagonists of t-PALP, could be used treat or prevent the onset of diabetes mellitus. In patients with newly diagnosed Types I and II diabetes, where some islet cell function remains, t-PALP polynucleotides or polypeptides, as well as agonists or antagonists of t-PALP, could be used to maintain the islet function so as to alleviate, delay or prevent permanent manifestation of the disease. Also, t-PALP polynucleotides or polypeptides, as well as agonists or antagonists of t-PALP, could be used as an auxiliary in islet cell transplantation to improve or promote islet cell function.

Neurological Diseases

In accordance with yet a further aspect of the present invention, there is provided a process for utilizing polynucleotides or polypeptides, as well as agonists or antagonists of the present invention, for therapeutic purposes, for example, to stimulate neurological cell proliferation and/or differentiation. Therefore, polynucleotides, polypeptides, agonists and/or antagonists of the invention may be used to treat and/or detect neurologic diseases. Moreover, polynucleotides or polypeptides, or agonists or antagonists of the invention, can be used as a marker or detector of a particular nervous system disease or disorder.

Examples of neurologic diseases which can be treated or detected with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis, cerebrovascular disorders (such as carotid artery diseases which include carotid artery thrombosis, carotid stenosis and Moyamoya Disease, cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache, migraine, dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, Hallervorden-Spatz Syndrome, hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, cerebral malaria, meningitis such as arachnoiditis, aseptic meningtitis such as viral meningtitis which includes lymphocytic choriomeningitis. Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie) cerebral toxoplasmosis, central nervous system neoplasms such as brain neoplasms that include cerebellear neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffiann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta, hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Horner's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, ophthalmoplegia such as Duane's Syndrome, Horner's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, Diabetic neuropathies such as diabetic foot, nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Infectious Disease t-PALP polynucleotides or polypeptides, or agonists or antagonists of t-PALP, can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, t-PALP polynucleotides or polypeptides, or agonists or antagonists of t-PALP, may also directly inhibit the infectious agent, without necessarily eliciting an immune response.

Viruses are one example of an infectious agent that can cause disease or symptoms that can be treated or detected by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat or detect any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat AIDS.

Similarly, bacterial or fungal agents that can cause disease or symptoms and that can be treated or detected by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., *Anthrax, Clostridium*), Bacteroidaceae, Blastomycosis, *Bordetella, Borrelia* (e.g., *Borrelia burgdorferi*, Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter, Legionellosis, Leptospirosis, Listeria, Mycoplasmatales, Mycobacterium leprae, Vibrio cholerae*, Neisseriaceae (e.g., *Acinetobacter, Gonorrhea, Menigococcal*), *Meisseria meningitidis*, Pasteurellacea Infections (e.g., *Actinobacillus, Heamophilus* (e.g., *Heamophilus influenza* type B), *Pasteurella*), *Pseudomonas,* Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat or detect any of these symptoms or diseases. In specific embodiments, Ppolynucleotides, polypeptides, agonists or antagonists of the invention are used to treat: tetanus, Diptheria, botulism, and/or meningitis type B.

Moreover, parasitic agents causing disease or symptoms that can be treated or detected by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and *Trichomonas* and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat or detect any of these symptoms or diseases. In specific embodiments, polynucleotides, polypeptides, or agonists or antagonists of the invention are used to treat malaria.

Preferably, treatment using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration t-PALP polynucleotides or polypeptides, or agonists or antagonists of t-PALP, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, t-PALP polynucleotides or polypeptides, or agonists or antagonists of t-PALP, may increase regeneration of tissues difficult to heal. For example, increased tendon/ligament regeneration would quicken recovery time after damage. t-PALP polynucleotides or polypeptides, or agonists or antagonists of t-PALP, of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using t-PALP polynucleotides or polypeptides, or agonists or antagonists of t-PALP, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the t-PALP polynucleotides or polypeptides, or agonists or antagonists of t-PALP.

Chemotaxis t-PALP polynucleotides or polypeptides, or agonists or antagonists of t-PALP, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

t-PALP polynucleotides or polypeptides, or agonists or antagonists of t-PALP, may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that t-PALP polynucleotides or polypeptides, or agonists or antagonists of t-PALP, may inhibit chemotactic activity. These molecules could also be used to treat disorders. Thus, t-PALP polynucleotides or polypeptides, or agonists or antagonists of t-PALP, could be used as an inhibitor of chemotaxis.

Binding Activity t-PALP polypeptides may be used to screen for molecules that bind to t-PALP or for molecules to which t-PALP binds. The binding of t-PALP and the molecule may activate (agonist), increase, inhibit (antagonist), or decrease activity of the t-PALP or the molecule bound. Examples of such molecules include antibodies, oligonucleotides, proteins (e.g., receptors), or small molecules.

Preferably, the molecule is closely related to the natural ligand of t-PALP, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which t-PALP binds, or at least, a fragment of the receptor capable of being bound by t-PALP (e.g., active site). In either case, the molecule can be rationally designed using known techniques.

Preferably, the screening for these molecules involves producing appropriate cells which express t-PALP, either as a secreted protein or on the cell membrane. Preferred cells include cells from mammals, yeast, *Drosophila*, or *E. coli*. Cells expressing t-PALP(or cell membrane containing the expressed polypeptide) are then preferably contacted with a test compound potentially containing the molecule to observe binding, stimulation, or inhibition of activity of either t-PALP or the molecule.

The assay may simply test binding of a candidate compound tot-PALP, wherein binding is detected by a label, or in an assay involving competition with a labeled competitor. Further, the assay may test whether the candidate compound results in a signal generated by binding to t-PALP.

Alternatively, the assay can be carried out using cell-free preparations, polypeptide/molecule affixed to a solid support, chemical libraries, or natural product mixtures. The assay may also simply comprise the steps of mixing a candidate compound with a solution containing t-PALP, measuring t-PALP/molecule activity or binding, and comparing the t-PALP/molecule activity or binding to a standard.

Preferably, an ELISA assay can measure t-PALP level or activity in a sample (e.g., biological sample) using a monoclonal or polyclonal antibody. The antibody can measure t-PALP level or activity by either binding, directly or indirectly, to t-PALP or by competing with t-PALP for a substrate.

Additionally, the receptor to which t-PALP binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of t-PALP thereby effectively generating agonists and antagonists of t-PALP. See generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S. *Trends Biotechnol.* 16(2): 76–82 (1998); Hansson, L. O., et al., *J. Mol. Biol.* 287: 265–76 (1999); and Lorenzo, M. M. and Blasco, R. *Biotechniques* 24(2):308–13 (1998) (each of these patents and publications are hereby incorporated by reference). In one embodiment, alteration of t-PALP polynucleotides and corresponding polypeptides may be achieved by DNA shuffling. DNA shuffling involves the assembly of two or more DNA segments into a desired t-PALP molecule by homologous, or site-specific, recombination. In another embodiment, t-PALP polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of t-PALP may be recombined with one or more components, motifs, sections, parts, domains, fragments, etc. of one or more heterologous molecules. In preferred embodiments, the heterologous molecules are t-PA and related protease-like molecules which possess such functions as the activation of plasminogen family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active t-PALP fragments. Biologically active fragments are those exhibiting activity similar, but not necessarily identical, to an activity of the t-PALP polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^{3}$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3 [H] thymidine in each case. The amount of fibroblast cell proliferation is measured by liquid scintillation chromatography which measures the incorporation of $^{3}$ [H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the t-PALP receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to t-PALP comprising the steps of: (a) incubating a candidate binding compound with t-PALP; and (b) determining if binding has occurred. Moreover, the invention includes a method of identifying agonists/antagonists comprising the steps of: (a) incubating a candidate compound with t-PALP, (b) assaying a biological activity, and (b) determining if a biological activity of t-PALP has been altered.

Also, one could identify molecules bind t-PALP experimentally by using the beta-pleated sheet regions disclosed in FIG. 3 and Table 1. Accordingly, specific embodiments of the invention are directed to polynucleotides encoding polypeptides which comprise, or alternatively consist of, the amino acid sequence of each beta pleated sheet regions disclosed in FIG. 3/Table 1. Additional embodiments of the invention are directed to polynucleotides encoding t-PALP polypeptides which comprise, or alternatively consist of, any combination or all of the beta pleated sheet regions disclosed in FIG. 3/Table 1. Additional preferred embodiments of the invention are directed to polypeptides which comprise, or alternatively consist of, the t-PALP amino acid sequence of each of the beta pleated sheet regions disclosed in FIG. 3/Table 1. Additional embodiments of the invention are directed to t-PALP polypeptides which comprise, or alternatively consist of, any combination or all of the beta pleated sheet regions disclosed in FIG. 3/Table 1.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxy-acetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense And Ribozyme (Antagonists)

In specific embodiments, antagonists according to the present invention are nucleic acids corresponding to the sequences contained in SEQ ID NO:1, or the complementary strand thereof, and/or to nucleotide sequences contained in the deposited clone 209023. In one embodiment, antisense sequence is generated internally, by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251: 1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcOR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the t-PALP antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the t-PALP antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding t-PALP, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a t-PALP gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded t-PALP antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a t-PALP RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of t-PALP shown in FIGS. 1A–B could be used in an antisense approach to inhibit translation of endogenous t-PALP mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of t-PALP mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the t-PALP coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy t-PALP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of t-PALP (FIGS. 1A–B). Preferably, the ribozyme is engineered so that the cleavage recognition site is located near the 5' end of the t-PALP mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express t-PALP in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous t-PALP messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating disorders or diseases, including but not limited to the disorders or diseases listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Other Activities

A polypeptide, polynucleotide, agonist, or antagonist of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

A polypeptide, polynucleotide, agonist, or antagonist of the present invention may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

A polypeptide, polynucleotide, agonist, or antagonist of the present invention may also be employed stimulate neuronal growth and to treat and prevent neuronal damage which occurs in certain neuronal disorders or neuro-degenerative conditions such as Alzheimer's disease, Parkinson's disease, and AIDS-related complex. A polypeptide, polynucleotide, agonist, or antagonist of the present invention may have the ability to stimulate chondrocyte growth, therefore, they may be employed to enhance bone and periodontal regeneration and aid in tissue transplants or bone grafts.

A polypeptide, polynucleotide, agonist, or antagonist of the present invention may be also be employed to prevent skin aging due to sunburn by stimulating keratinocyte growth.

A polypeptide, polynucleotide, agonist, or antagonist of the present invention may also be employed for preventing hair loss, since FGF family members activate hair-forming cells and promotes melanocyte growth. Along the same lines, a polypeptide, polynucleotide, agonist, or antagonist of the present invention may be employed to stimulate growth and differentiation of hematopoietic cells and bone marrow cells when used in combination with other cytokines.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

A polypeptide, polynucleotide, agonist, or antagonist of the present invention may also be used to modulate mammalian characteristics, such as body height, weight, hair color, eye color, skin, percentage of adipose tissue, pigmentation, size, and shape (e.g., cosmetic surgery). Similarly, a polypeptide, polynucleotide, agonist, or antagonist of the present invention may be used to modulate mammalian metabolism affecting catabolism, anabolism, processing, utilization, and storage of energy.

A polypeptide, polynucleotide, agonist, or antagonist of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide, polynucleotide, agonist, or antagonist of the present invention may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

EXAMPLES

Example 1

Expression and Purification of "His-tagged" t-PALP in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion of the t-PALP protein comprising the mature form of the t-PALP amino acid sequence is amplified from the deposited cDNA clone using PCR oligonucleotide primers which anneal to the amino terminal sequences of the desired portion of the t-PALP protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature form of the t-PALP protein, the 5' primer has the sequence 5' GGC CGACATGTC TGG AGG CTG TTT CTG G 3' (SEQ ID NO:11) containing the underlined Afl III restriction site followed by 17 nucleotides of the amino terminal coding sequence of the mature t-PALP sequence in SEQ ID NO:2. One of ordinary skill in the art would appreciate, of course, that the point in the protein coding sequence where the 5' primer begins may be varied to amplify a DNA segment encoding any desired portion of the complete t-PALP protein shorter or longer than the mature form of the protein. The 3' primer has the sequence 5' GGC GGAAGCTTATTA GGC CCC AGG AGT CCC GGC 3' (SEQ ID NO:12) containing the underlined Hind III restriction site followed by 22 nucleotides complementary to the 3' end of the coding sequence of the t-PALP DNA sequence in FIGS. 1A, 1B, and 1C.

The amplified t-PALP DNA fragment and the vector pQE9 are digested with Afl III and Hind III and the digested DNAs are then ligated together. Insertion of the t-PALP DNA into the restricted pQE9 vector places the t-PALP protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual,* 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing t-PALP protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 m ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the t-PALP is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIA expressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the t-PALP is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify t-PALP expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the t-PALP polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded t-PALP polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the t-PALP polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the t-PALP polypeptide (determined, for instance, by 16% SDS-PAGE) are then pooled.

The resultant t-PALP polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

In an additional preferred embodiment, amino acid residues Ser-122 through Asp-165 of the t-PALP sequence shown in FIGS. 1A, 1B, and 1C (which is identical to residues Ser-1 through Asp-144 of SEQ ID NO:2) is expressed using the pHE-4 bacterial expression vector (ATCC Accession No. 209311). In this embodiment, residues Ser-1 through Asp-144 of the t-PALP amino acid sequence shown in SEQ ID NO:2 is expressed in *E. coli* using essentially the protocol described in this Example. A polynucleotide encoding amino acid residues Ser-1 through Asp-144 of the t-PALP amino acid sequence shown in SEQ ID NO:2 is subcloned cloned into the 5' Nde I and 3' Asp 718 restriction endonuclease sites of the pHE-4 bacterial expression vector. One of skill in the art could easily design appropriate primers to achieve such subcloning. For example, a 5' and 3' primer pair which has been used successfully to generate the desired subclone is as follows: 5' primer: 5'-GGC TCG CAT ATG TCT GGA GGC TGT TTC TGG GAC-3' (SEQ ID NO:29) and 3' primer: 5'-GCG CAT GGT ACC TTA TTA GTC CTT TTT CTC CTT GGA GTT C-3' (SEQ ID NO:30).

Example 2

Cloning and Expression of t-PALP Protein in a Baculovirus Expression System

In this illustrative example, the plasmid shuttle vector pA2 is used to insert the cloned DNA encoding complete protein, including its naturally associated secretory signal (leader) sequence, into a baculovirus to express the mature t-PALP protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length t-PALP protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' GGC CGGGATCCG CCA TCA TGC TGT TGG CCT GGG TAC 3' (SEQ ID NO:13) containing the underlined Bam HI restriction enzyme site, an efficient signal for initiation of translation in eukaryotic cells, as described by Kozak, M., J. *Mol. Biol.* 196:947–950 (1987), followed by 25 of nucleotides of the sequence of the complete t-PALP protein shown in FIGS. 1A, 1B, and 1C, beginning with the AUG initiation codon. The 3' primer has the sequence 5' GGC CGGGTACCT TAT TAG GCC CCA GGA GTC CCG GC 3' (SEQ ID NO:14) containing the underlined Asp 718 restriction site followed by 24 nucleotides complementary to the 3' noncoding sequence in FIGS. 1A, 1B, and 1C.

The amplified fragment is isolated from a 1% agarose gel using a commercially available kit ("Geneclean," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human t-PALP gene by digesting DNA from individual colonies using Bam HI and Asp 718 and then analyzing the digestion product by gel electrophoresis. The sequence of the cloned fragment is confirmed by DNA sequencing. This plasmid is designated herein pA2t-PALP.

Five μg of the plasmid pA2t-PALP is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). One μg of BaculoGold™ virus DNA and 5 μg of the plasmid pA2t-PALP are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-t-PALP.

To verify the expression of the t-PALP gene Sf9 cells are grown in Grace's medium supplemented with 10% heat-inactivated FBS. The cells are infected with the recombinant baculovirus V-t-PALP at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the t-PALP protein and thus the cleavage point and length of the naturally associated secretory signal peptide.

Example 3

Cloning and Expression of t-PALP in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J* 227:277–279 (1991); Bebbington et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology,* 438–447 (March, 1985)) plus a fragment of the CMV-enhancer (Boshart et al., *Cell* 41:521–530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

The expression plasmid, pt-PALPHA, is made by cloning a portion of the cDNA encoding the mature form of the t-PALP protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope. pcDNAIII contains, in addition, the selectable neomycin marker.

Example 3(a)

Cloning and Expression in COS Cells

A DNA fragment encoding the complete t-PALP polypeptide is cloned into the polylinker region of the vector so that recombinant protein expression is directed by the CMV promoter. The plasmid construction strategy is as follows.

The t-PALP cDNA of the deposited clone is amplified using primers that contain convenient restriction sites, much as described above for construction of vectors for expression of t-PALP in *E. coli*. Suitable primers include the following, which are used in this example. The 5' primer, containing the underlined Bam HI site, a Kozak sequence, an AUG start codon, and 25 nucleotides of the 5' coding region of the complete t-PALP polypeptide, has the following sequence: 5' GGC CGGGATCCG CCA TCA TGC TGT TGG CCT GGG TAC 3' (SEQ ID NO:15). The 3' primer, containing the underlined Asp 718 and 24 of nucleotides complementary to the 3' coding sequence immediately before the stop codon, has the following sequence: 5' GGC CGG GTA CCT TAT TAG GCC CCA GGA GTC CCG GC 3' (SEQ ID NO:16).

The PCR amplified DNA fragment and the vector, pcDNAI/Amp, are digested with Bam HI and Asp 718 and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the complete t-PALP polypeptide For expression of recombinant t-PALP, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of t-PALP by the vector.

Expression of the t-PALP-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of t-PALP polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the t-PALP polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel.

The DNA sequence encoding the t-PALP polypeptide is amplified using PCR oligonucleotide primers corresponding to the 5' and 3' sequences of the desired portion of the gene. The 5' primer containing the underlined Bam HI site, a Kozak sequence, an AUG start codon, and 25 nucleotides of the 5' coding region of the t-PALP polypeptide, has the following sequence: 5' GGC CGGGATCCG CCA TCA TGC TGT TGG CCT GGG TAC 3' (SEQ ID NO:15). The 3' primer, containing the underlined Asp 718 and 24 of nucleotides complementary to the 3' coding sequence immediately before the stop codon as shown in FIGS. 1A, 1B, and 1C (SEQ ID NO:1), has the following sequence: 5' GGC CG GGTACCT TAT TAG GCC CCA GGA GTC CCG GC 3' (SEQ ID NO:16).

The amplified fragment is digested with the endonucleases Bam HI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2- neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue Distribution of t-PALP mRNA Expression

Northern blot analysis was carried out to examine t-PALP gene expression in human tissues using methods described by, among others, Sambrook et al., cited above. A cDNA probe containing the entire nucleotide sequence of the t-PALP protein (SEQ ID NO:1) was labeled with $^{32}P$ using the rediprime™ DNA labeling system (Amersham Life Science), according to manufacturer's instructions. After labeling, the probe was purified using a TE Select-D G50 spin column (5 prime-3 prime, Inc.) according to manufacturer's recommendations. The purified labeled probe was then used to examine various human tissues for t-PALP mRNA.

Multiple Tissue Northern (MTN) blots containing various human tissues (H) or human immune system tissues (IM) were obtained from Clontech and were examined with the labeled probe using ExpressHyb™ hybridization solution (Clontech) according to manufacturer's protocol number PT1190-1. Following hybridization and washing, the blots were mounted and exposed to film at −70° C. overnight, and films developed according to standard procedures.

The Northern blot experiments described above indicated expression of 2.5 kb t-PALP message in the following tissues: heart, brain, placenta, lung, liver, skeletal muscle, kidney, pancreas, spleen, thymus, prostate, testis, ovary, small intestine, colon, and peripheral blood leukocytes.

Example 5

Isolation of t-PALP Genomic Clones

A human genomic P1 library (Genomic Systems, Inc.) is screened by PCR using primers selected for the cDNA sequence corresponding to SEQ ID NO:1, according to the method described in Example 1. (See also, Sambrook.)

Example 6

Chromosomal Mapping of t-PALP

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 7

Construction of N-Terminal and/or C-Terminal Deletion Mutants

The following general approach may be used to clone a N-terminal or C-terminal deletion t-PALP deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired t-PALP polynucleotide fragment. An initiation and stop codon are added to the 5' and 3' primers respectively, if necessary, to express the t-PALP polypeptide fragment encoded by the polynucleotide fragment. Preferred t-PALP polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the t-PALP polynucleotide fragment in a desired vector may also be added to the 5' and 3' primer sequences. The t-PALP polynucleotide fragment is amplified from genomic DNA or from the deposited cDNA clone using the appropriate PCR oligonucleotide primers and conditions discussed herein or known in the art. The t-PALP polypeptide fragments encoded by the t-PALP polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the t-PALP polypeptide fragment C-4 to V-63 of SEQ ID NO:2 is amplified and cloned as follows: A 5' primer is generated comprising a restriction enzyme site followed by an initiation codon in frame with the polynucleotide sequence encoding the N-terminal portion of the polypeptide fragment beginning with C-4 of SEQ ID NO:2. A complementary 3' primer is generated comprising a restriction enzyme site followed by a stop codon in frame with the polynucleotide sequence encoding C-terminal portion of the t-PALP polypeptide fragment ending with V-63 of SEQ ID NO:2.

The amplified polynucleotide fragment and the expression vector are digested with restriction enzymes which recognize the sites in the primers. The digested polynucleotides are then ligated together. The t-PALP polynucleotide fragment is inserted into the restricted expression vector, preferably in a manner which places the t-PALP polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 8

Protein Fusions of t-PALP t-PALP polypeptides are preferably fused to other proteins. These fusion proteins can be used for a variety of applications. For example, fusion of t-PALP polypeptides to His-tag, HA-tag, protein A, IgG domains, and maltose binding protein facilitates purification. (See EP A 394,827; Traunecker, et al., Nature 331:84–86 (1988).) Similarly, fusion to IgG-1, IgG-3, and albumin increases the halflife time in vivo. Nuclear localization signals fused to t-PALP polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a t-PALP polynucleotide is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

```
Human IgG Fc region:
GGGATCCGGAGCCCAAATCTTCTGACAAAACTCACA (SEQ ID NO:17)

CATGCCCACCGTGCCCAGCACCTGAATTCGAGGGTG

CACCGTCAGTCTTCCTCTTCCCCCCAAAACCCAAGG

ACACCCTCATGATCTCCCGGACTCCTGAGGTCACAT

GCGTGGTGGTGGACGTAAGCCACGAAGACCCTGAGG

TCAAGTTCAACTGGTACGTGGACGGCGTGGAGGTGC

ATAATGCCAAGACAAAGCCGCGGGAGGAGCAGTACA

ACAGCACGTACCGTGTGGTCAGCGTCCTCACCGTCC

TGCACCAGGACTGGCTGAATGGCAAGGAGTACAAGT

GCAAGGTCTCCAACAAAGCCCTCCCAACCCCCATCG

AGAAAACCATCTCCAAAGCCAAAGGGCAGCCCCGAG

AACCACAGGTGTACACCCTGCCCCCATCCCGGGATG

AGCTGACCAAGAACCAGGTCAGCCTGACCTGCCTGG

TCAAAGGCTTCTATCCAAGCGACATCGCCGTGGAGT
```

-continued

```
GGGAGAGCAATGGGCAGCCGGAGAACAACTACAAGA

CCACGCCTCCCGTGCTGGACTCCGACGGCTCCTTCT

TCCTCTACAGCAAGCTCACCGTGGACAAGAGCAGGT

GGCAGCAGGGGAACGTCTTCTCATGCTCCGTGATGC

ATGAGGCTCTGCACAACCACTACACGCAGAAGAGCC

TCTCCCTGTCTCCGGGTAAATGAGTGCGACGGCCGC

GACTCTAGAGGAT
```

Example 9

Production of an Antibody

Hybridoma Technology

The antibodies of the present invention can be prepared by a variety of methods. (See, Current Protocols, Chapter 2.) As one example of such methods, cells expressing t-PALP is administered to an animal to induce the production of sera containing polyclonal antibodies. In a preferred method, a preparation of t-PALP protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with t-PALP polypeptide or, more preferably, with a secreted t-PALP polypeptide-expressing cell. Such cells may be cultured in any suitable tissue culture medium; however, it is preferable to culture cells in Earle's modified Eagle's medium supplemented with 10% fetal bovine serum (inactivated at about 56 degree C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the t-PALP polypeptide.

Alternatively, additional antibodies capable of binding to t-PALP polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the t-PALP protein-specific antibody can be blocked byt-PALP. Such antibodies comprise anti-idiotypic antibodies to the t-PALP protein-specific antibody and can be used to immunize an animal to induce formation of further t-PALP protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted t-PALP protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed Against t-PALP from a Library of scFvs.

Naturally occuring V-genes isolated from human PBLs are constructed into a large library of antibody fragments which contain reactivities against t-PALP to which the donor may or may not have been exposed (see e.g., U.S. Pat. No. 5,885,793 incorporated herein in its entirety by reference).

Rescue of the Library. A library of scFvs is constructed from the RNA of human PBLs as described in WO92/01047. To rescue phage displaying antibody fragments, approximately $10^9$ *E. coli* harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2\times10^8$ TU of delta gene 3 helper (M13 delta gene III, see WO92/01047) are added and the culture incubated at 37 degree C. for 45 minutes without shaking and then at 37 degree C. for 45 minutes with shaking. The culture is centrifuged at 4000 r.p.m. for 10 min. and the pellet resuspended in 2 liters of of 2×TY containing 100 ug/ml ampicillin and 50 ug/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37 degree C. without shaking and then for a further hour at 37 degree C. with shaking. Cells are spun down (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library. Immunotubes (Nunc) are coated overnight in PBS with 4 ml of either 100 ug/ml or 10 ug/ml of a polypeptide of the present invention. Tubes are blocked with 2% Marvel-PBS for 2 hours at 37 degree C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37 degree C. The *E. coli* are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 10

Production of t-PALP Protein for High-Throughput Screening Assays

The following protocol produces a supernatant containing t-PALP polypeptide to be tested. This supernatant can then be used in the Screening Assays described in Examples 12–19.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1× Penstrep(17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 7–8, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37 degree C. for 6 hours.

While cells are incubating, prepare appropriate media, either 1% BSA in DMEM with 1× penstrep, or HGS CHO-5 media (116.6 mg/L of $CaCl_2$ (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1× penstrep. (BSA (81-068-3 Bayer) 100 gm dissolved in IL DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 12–19.

It is specifically understood that when activity is obtained in any of the assays described below using a supernatant, the activity originates from either the t-PALP polypeptide directly (e.g., as a secreted protein) or by t-PALP inducing expression of other proteins, which are then secreted into the supernatant. Thus, the invention further provides a method of identifying the protein in the supernatant characterized by an activity in a particular assay.

Example 11

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:5)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs tyk2 | Jak1 | Jak2 | Jak3 | STATS | GAS (elements) or ISRE |
|---|---|---|---|---|---|---|
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1, 3 | |
| gp130 family | | | | | | |
| IL-6 (Pleiotrohic) | + | + | + | ? | 1, 3 | GAS (IRF1 > Lys6 > IFP) |
| Il-11(Pleiotrohic) | ? | + | ? | ? | 1, 3 | |
| OnM(Pleiotrohic) | ? | + | + | ? | 1, 3 | |
| LIF(Pleiotrohic) | ? | + | + | ? | 1, 3 | |
| CNTF(Pleiotrohic) | −/+ | + | + | ? | 1, 3 | |
| G-CSF(Pleiotrohic) | ? | + | ? | ? | 1, 3 | |
| IL-12(Pleiotrohic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS(B-CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is: 5'-GCG CCT CGA GAT TTC CCC GAA ATC TAG ATT TCC CCG AAA TGA TTT CCC CGA AAT GAT TTC CCC GAA ATA TCT GCC ATC TCA ATT AG-3' (SEQ ID NO:18)

The downstream primer is complementary to the SV40 promoter and is flanked with a Hind III site: 5'-GCG GCA AGC TTT TTG CAA AGC CTA GGC-3' (SEQ ID NO:19).

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

```
5':CTCGAGATTTCCCCGAAATCTAGATTTCCCCGA (SEQ ID NO:20)

AATGATTTCCCCGAAATGATTTCCCCGAAATATCTG
```

-continued

```
CCATCTCAATTAGTCAGCAACCATAGTCCCGCCCCT

AACTCCGCCCATCCCGCCCCTAACTCCGCCCAGTTC

CGCCCATTCTCCGCCCCATGGCTGACTAATTTTTTT

TATTTATGCAGAGGCCGAGGCCGCCTCGGCCTCTGA

GCTATTCCAGAAGTAGTGAGGAGGCTTTTTTGGAGG

CCTAGGCTTTTGCAAAAAGCTT:3'.
```

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 12–13.

Other constructs can be made using the above description and replacing GAS with a different promoter sequence. For example, construction of reporter molecules containing NF-kappaB and EGR promoter sequences are described in Examples 14 and 15. However, many other promoters can be substituted using the protocols described in these Examples. For instance, SRE, IL-2, NFAT, or Osteocalcin promoters can be substituted, alone or in combination (e.g., GAS/NF-KappaB/EGR, GAS/NF-KappaB, Il-2/NFAT, or NF-KappaB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 12

High-Throughput Screening Assay for T-cell Activity

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 13. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15-45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37 degree C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing t-PALP polypeptides or t-PALP induced polypeptides as produced by the protocol described in Example 10.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degree C. until SEAP assays are performed according to Example 18. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 13

High-Throughput Screening Assay Identifying Myeloid Activity

The following protocol is used to assess myeloid activity of t-PALP by determining whether t-PALP proliferates and/or differentiates myeloid cells. Myeloid cell activity is assessed using the GAS/SEAP/Neo construct produced in Example 11. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 10, a DEAE-Dextran method (Kharbanda et. al., 1994, Cell Growth & Differentiation, 5:259–265) is used. First, harvest $2\times10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4$. $7H_2O$, 1 mM $MgCl_2$, and 675 uM $CaCl_2$. Incubate at 37 degrees C. for 45 min.

Wash the cells with RPMI 1640 medium containing 10% FBS and then resuspend in 10 ml complete medium and incubate at 37 degree C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 12. Incubate at 37 degee C for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 18.

Example 14

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by t-PALP.

Particularly, the following protocol is used to assess neuronal activity in PC12 cell lines. PC12 cells (rat pheno-chromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by t-PALP can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers: 5'-GCG CTC GAG GGA TGA CAG CGA TAG AAC CCC GG-3' (SEQ ID NO:21); and 5'-GCG AAG CTT CGC GAC TCC CCG GAT CCG CCT C-3' (SEQ ID NO:22).

Using the GAS:SEAP/Neo vector produced in Example 13, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIO-SCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 10. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 10, 37 degree C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 16.

Example 15

High-Throughput Screening Assay for T-cell Activity

NF-KappaB (Nuclear Factor Kappa B) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KappaB regulates the expression of genes involved in immune cell activation, control of apoptosis (NF-KappaB appears to shield cells from apoptosis), B and T-cell development, anti-viral and antimicrobial responses, and multiple stress responses.

In non-stimulated conditions, NF-KappaB is retained in the cytoplasm with I-KappaB (Inhibitor Kappa B). However, upon stimulation, I-KappaB is phosphorylated and degraded, causing NF-KappaB to shuttle to the nucleus, thereby activating transcription of target genes. Target genes activated by NF-KappaB include IL-2, IL-6, GM-CSF, ICAM-1 and class 1 MHC.

Due to its central role and ability to respond to a range of stimuli, reporter constructs utilizing the NF-KappaB promoter element are used to screen the supernatants produced in Example 10. Activators or inhibitors of NF-KappaB would be useful in treating diseases. For example, inhibitors of NF-KappaB could be used to treat those diseases related to the acute or chronic activation of NF-KappaB, such as rheumatoid arthritis.

To construct a vector containing the NF-KappaB promoter element, a PCR based strategy is employed. The upstream primer contains four tandem copies of the NF-KappaB binding site (GGG GAC TTT CCC) (SEQ ID NO:31), 18 bp of sequence complementary to the 5' end of the SV40 early promoter sequence, and is flanked with an XhoI site: 5'-GCG GCC TCG AGG GGA CTT TCC CGG GGA CTT TCC GGG GAC TTT CCG GGA CTT TCC ATC CTG CCA TCT CAA TTA G-3' (SEQ ID NO:23).

The downstream primer is complementary to the 3' end of the SV40 promoter and is flanked with a Hind III site: 5'-GCG GCA AGC TTT TTG CAA AGC CTA GGC-3' (SEQ ID NO:19).

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence: 5'-

```
CTCGAGGGGACTTTCCCGGGGACTTTCCGGGGACTT (SEQ ID NO:24)
TCCGGGACTTTCCATCTGCCATCTCAATTAGTCAGC
AACCATAGTCCCGCCCCTAACTCCGCCCATCCCGCC
CCTAACTCCGCCCAGTTCCGCCCATTCTCCGCCCCA
TGGCTGACTAATTTTTTTTATTTATGCAGAGGCCGA
GGCCGCCTCGGCCTCTGAGCTATTCCAGAAGTAGTG
AGGAGGCTTTTTTGGAGGCCTAGGCTTTTGCAAAAA
GCTT:3'.
```

Next, replace the SV40 minimal promoter element present in the pSEAP2-promoter plasmid (Clontech) with this NF-KappaB/SV40 fragment using XhoI and HindIII. However, this vector does not contain a neomycin resistance gene, and therefore, is not preferred for mammalian expression systems.

In order to generate stable mammalian cell lines, the NF-KappaB/SV40/SEAP cassette is removed from the above NF-KappaB/SEAP vector using restriction enzymes SalI and NotI, and inserted into a vector containing neomycin resistance. Particularly, the NF-KappaB/SV40/SEAP cassette was inserted into pGFP-1 (Clontech), replacing the GFP gene, after restricting pGFP-1 with SalI and NotI.

Once NF-KappaB/SV40/SEAP/Neo vector is created, stable Jurkat T-cells are created and maintained according to the protocol described in Example 12. Similarly, the method for assaying supernatants with these stable Jurkat T-cells is also described in Example 14. As a positive control, exogenous TNF alpha (0.1, 1, 10 ng) is added to wells H9, H10, and H11, with a 5–10 fold activation typically observed.

Example 16

Assay for SEAP Activity

As a reporter molecule for the assays described in Examples 12–15, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 17

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to 2–5×$10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30–60 min. The cells are washed twice with HBSS, resuspended to 1×$10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 mm; and (6) Sample addition is 50 ul. Increased emission at 530 nm indicates an extracellular signaling event caused by the a molecule, either t-PALP or a molecule induced by t-PALP, which has resulted in an increase in the intracellular Ca++ concentration.

Example 18

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether t-PALP or a molecule induced by t-PALP is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 10, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 mM ATP/50 mM $MgCl_2$), then 10 ul of 5× Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30 degree C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degree C. for 20 min. This allows the streptavadin coated 96 well plate to associate with the biotinylated peptide. Wash the MTP module with 300 µl/well of PBS four times. Next add 75 ul of anti-phospotyrosine antibody conjugated to horse radish peroxidase (anti-P-Tyr-POD(0.5 u/ml)) to each well and incubate at 37 degree C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 19

High-Throughput Screening Assay Identifying Phosphorylation Activity

As a potential alternative and/or compliment to the assay of protein tyrosine kinase activity described in Example 18, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), RAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 12 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (lug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by t-PALP or a molecule induced by t-PALP.

Example 20

Method of Determining Alterations in the t-PALP Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degree C. for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of t-PALP is also determined and genomic PCR products analyzed to confirm the results. PCR products harboring suspected mutations in t-PALP is then cloned and sequenced to validate the results of the direct sequencing.

PCR products of t-PALP are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in t-PALP not present in unaffected individuals.

Genomic rearrangements are also observed as a method of determining alterations in a gene corresponding to t-PALP. Genomic clones isolated according to Example 4 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the t-PALP genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of t-PALP (hybridized by the probe) are identified as insertions, deletions, and translocations. These t-PALP alterations are used as a diagnostic marker for an associated disease.

Example 21

Method of Detecting Abnormal Levels of t-PALP in a Biological Sample t-PALP polypeptides can be detected in a biological sample, and if an increased or decreased level of t-PALP is detected, this polypeptide is a marker for a particular phenotype. Methods of detection are numerous, and thus, it is understood that one skilled in the art can modify the following assay to fit their particular needs.

For example, antibody-sandwich ELISAs are used to detect t-PALP in a sample, preferably a biological sample. Wells of a microtiter plate are coated with specific antibodies to t-PALP, at a final concentration of 0.2 to 10 ug/ml. The antibodies are either monoclonal or polyclonal and are produced by the method described in Example 11. The wells are blocked so that non-specific binding of t-PALP to the well is reduced.

The coated wells are then incubated for >2 hours at RT with a sample containing t-PALP. Preferably, serial dilutions of the sample should be used to validate results. The plates are then washed three times with deionized or distilled water to remove unbounded t-PALP.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot t-PALP polypeptide concentration on the X-axis (log scale) and fluorescence or absorbance of the Y-axis (linear scale). Interpolate the concentration of the t-PALP in the sample using the standard curve.

Example 22

Formulation

The invention also provides methods of treatment and/or prevention of diseases or disorders (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrastemal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1 alpha, IL-1 beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, Il-20, and IL- 21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (P1GF), as disclosed in International Publication Number WO 92/06194; Placental Growth Factor-2 (P1GF-2), as disclosed in Hauser et al., Gorwth Factors, 4:259–268 (1993); Vascular Endothelial Growth Factor (VEGF), as disclosed in International Publication Number WO 90/13649;, Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B 186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKNE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 23

Method of Treating Decreased Levels of t-PALP

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of t-PALP in an individual can be treated by administering t-PALP, preferably in the secreted form. Thus, the invention also provides a method of treatment of an individual in need of an increased level of t-PALP polypeptide comprising administering to such an individual a Therapeutic comprising an amount of t-PALP to increase the activity level of t-PALP in such an individual.

For example, a patient with decreased levels of t-PALP polypeptide receives a daily dose 0.1–100 ug/kg of the polypeptide for six consecutive days. Preferably, the polypeptide is in the secreted form. The exact details of the dosing scheme, based on administration and formulation, are provided in Example 22.

Example 24

Method of Treating Increased Levels of t-PALP

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of t-PALP. This technology is one example of a method of decreasing levels of t-PALP polypeptide, preferably a secreted form, due to a variety of etiologies, such as cancer.

For example, a patient diagnosed with abnormally increased levels of t-PALP is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 22.

Example 25

Method of Treatment Using Gene Therapy—Ex Vivo

One method of gene therapy transplants fibroblasts, which are capable of expressing t-PALP polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcORI and HindIII and subsequently treated with calf intestinal phosphatase. The linear vector is fractionated on agarose gel and purified, using glass beads.

The cDNA encoding t-PALP can be amplified using PCR primers which correspond to the 5' and 3' end sequences respectively as set forth in Example 1. Preferably, the 5' primer contains an EcORI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted t-PALP.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the t-PALP gene is then added to the media and the packaging cells transduced with the vector. The packaging cells now produce infectious viral particles containing the t-PALP gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether t-PALP protein is produced.

The engineered fibroblasts are then transplanted onto the host, either alone or after having been grown to confluence on cytodex 3 microcarrier beads.

Example 26

Gene Therapy Using Endogenous t-PALP Gene

Another method of gene therapy according to the present invention involves operably associating the endogenous t-PALP sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous t-PALP, flanking the promoter. The targeting sequence will be sufficiently near the 5' end of t-PALP so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous t-PALP sequence. This results in the expression of t-PALP in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2$ $HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the t-PALP locus, plasmid pUC18 (MBI Fermentas, Amherst, N.Y.) is digested with HindIII. The CMV promoter is amplified by PCR with an XbaI site on the 5' end and a BamHI site on the 3' end. Two t-PALP non-coding sequences are amplified via PCR: one t-PALP non-coding sequence (t-PALP fragment 1) is amplified with a HindIII site at the 5' end and an Xba site at the 3' end; the other t-PALP non-coding sequence (t-PALP fragment 2) is amplified with a BamHI site at the 5'end and a HindIII site at the 3'end. The CMV promoter and t-PALP fragments (1 and 2) are digested with the appropriate enzymes (CMV promoter—XbaI and BamHI; t-PALP fragment 1—XbaI; t-PALP fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5\times10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 27

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) t-PALP sequences into an animal to increase or decrease the expression of the t-PALP polypeptide. The t-PALP polynucleotide may be operatively linked to a promoter or any other genetic elements necessary for the expression of the t-PALP polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The t-PALP polynucleotide constructs may be delivered by any method that delivers injectable materials to the cells of an animal, such as, injection into the interstitial space of tissues (heart, muscle, skin, lung, liver, intestine and the like). The t-PALP polynucleotide constructs can be delivered in a pharmaceutically acceptable liquid or aqueous carrier.

The term “naked” polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the t-PALP polynucleotides may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The t-PALP polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The t-PALP polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked t-PALP polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked t-PALP polynucleotide constructs can be delivered to arteries during angioplasty by the catheter used in the procedure.

The dose response effects of injected t-PALP polynucleotide in muscle in vivo is determined as follows. Suitable t-PALP template DNA for production of mRNA coding for t-PALP polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The t-PALP template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for t-PALP protein expression. A time course for t-PALP protein expression may be done in a similar fashion except that quadriceps from different mice are harvested at different times. Persistence of t-PALP DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using t-PALP naked DNA.

Example 28 t-PALP Transgenic Animals

The t-PALP polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Any of the t-PALP polypeptides disclosed throughout this application can be used to generate transgenic animals. For example, DNA encoding amino acids M(−)21 to V63 of SEQ ID NO:2 can be inserted into a vector containing a promoter, such as the actin promoter, which will ubiquitously express the inserted fragment. Primers that can be used to generate such fragments include a 5' primer containing a BamHI restriction site: 5'-CGA AGA GGG ATC CAT GCT GTT GGC CTG GGT ACA AGC-3' (SEQ ID NO:25) and a 3' primer, containing an XbaI restriction site: 5'-GCC GGC TCT AGA TCA GAC GTA GCA CCA GGG CCC GCG CGG G-3' (SEQ ID NO:26). This construct will express the kringle domain of t-PALP under the control of the actin promoter for ubiquitous expression. The region of t-PALP included in this construct extends from M(−)21 to V63 of SEQ ID NO:2. Correspondingly, it would also be routine for one skilled in the art to generate 5' and 3' primers to express only the protease domain, or other fragments, of t-PALP in transgenic animals.

Similarly, DNA encoding full length t-PALP protein, for example M(−)21 to A242 of SEQ ID NO:2, can also be inserted into a vector using the following primers: A 5' primer containing a BamHI restriction site: 5'-CGA AGA GGG ATC CAT GCT GTT GGC CTG GGT ACA AGC-3' (SEQ ID NO:25) and a 3' primer, containing an XbaI restriction site: 5'-CAC TGG TCT AGA TCA GGC CCC AGG AGT CCC GGC-3' (SEQ ID NO:27).

Besides these two examples, other fragments of t-PALP can also be inserted into a vector to create transgenics having ubiquitous expression.

Alternatively, polynucleotides of the invention can be inserted in a vector which controls tissue specific expression through a tissue specific promoter. For example, a construct having a transferrin promoter would express the kringle domain of t-PALP in the liver of transgenic animals. Therefore, DNA encoding amino acids M(−)21 to V63 of SEQ ID NO:2 can be amplified using a 5' primer, containing a BamHI restriction site: 5'-CGA AGA GGG ATC CAT GCT GTT GGC CTG GGT ACA AGC-3' (SEQ ID NO:25) and a 3' primer, containing an XbaI restriction site: 5'-GCC GGC TCT AGA TCA GAC GTA GCA CCA GGG CCC GCG CGG G-3' (SEQ ID NO:26).

Similarly, DNA encoding the full length t-PALP protein can also be inserted into a vector for tissue specific expression using the following primers: A 5' primer containing a BamHI restriction site: 5'-CGA AGA GGG ATC CAT GCT GTT GGC CTG GGT ACA AGC-3' (SEQ ID NO:25) and a 3' primer, containing an XbaI restriction site: 5'-CAC TGG TCT AGA TCA GGC CCC AGG AGT CCC GGC-3' (SEQ ID NO:27). In addition to expressing t-PALP in a ubiquitous or tissue specific manner in transgenic animals, it would also be routine for one skilled in the art to generate constructs which regulate t-PALP expression by a variety of other means (for example, developmentally or chemically regulated expression).

Once transgenic animals have been generated, the expression of the recombinant gene may be assayed utilizing standard techniques. Initial screening may be accomplished by Southern blot analysis or PCR techniques to analyze animal tissues to verify that integration of the transgene has occurred. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of t-PALP polypeptides, studying conditions and/or disorders associated with aberrant t-PALP expression, and in screening for compounds effective in ameliorating such conditions and/or disorders.

Example 29 t-PALP Knock-Out Animals

Endogenous t-PALP gene expression can also be reduced by inactivating or "knocking out" the t-PALP gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the t-PALP polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of t-PALP polypeptides, studying conditions and/or disorders associated with aberrant t-PALP expression, and in screening for compounds effective in ameliorating such conditions and/or disorders.

Example 30

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified t-PALP protein, or truncated forms thereof, is assessed for its ability to induce activation, proliferation, differentiation or inhibition and/or death in B-cell populations and their precursors. The activity of t-PALP protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of t-PALP protein, or truncated forms thereof. Mice receive this treatment for 4 consecutive days, at which time they are sacrificed and various tissues and serum collected for analyses. Comparison of H&E sections from normal and t-PALP protein-treated spleens identify the results of the activity of t-PALP protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from t-PALP protein-treated mice is used to indicate whether t-PALP protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and t-PALP protein-treated mice.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 31

T Cell Proliferation Assay

A CD3-induced proliferation assay is performed on PBMCs and is measured by the uptake of $^3$H-thymidine. The assay is performed as follows. Ninety-six well plates are coated with 100 microliters/well of mAb to CD3 (HIT3a, Pharmingen) or isotype-matched control mAb (B33.1) overnight at 4° C. (1 micrograms/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of t-PALP protein (total volume 200 microliters). Relevant protein buffer and medium alone are controls. After 48 hr. culture at 37° C., plates are spun for 2 min. at 1000 rpm and 100 microliters of supernatant is removed and stored −20° C. for measurement of IL-2 (or other cytokines) if effect on proliferation is observed. Wells are supplemented with 100 microliters of medium containing 0.5 microCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of t-PALP proteins.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 32

Effect of t-PALP on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-alpha, causes a rapid change in surface phenotype (increased expression of MHC class I and II, costimulatory and adhesion molecules, downregulation of FCgammaRII, upregulation of CD83). These changes correlate with increased antigen-presenting capacity and with functional maturation of the dendritic cells.

FACS analysis of surface antigens is performed as follows. Cells are treated 1–3 days with increasing concentrations of t-PALP or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ml) are treated with increasing concentrations of t-PALP for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of t-PALP or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. t-PALP, agonists, or antagonists of t-PALP can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 μg/ml, and then incubaed at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of t-PALP and under the same conditions, but in the absence of t-PALP. For IL-12 production, the cells are primed overnight with IFN (100 U/ml) in presence of t-PALP. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative burst. Purified monocytes are plated in 96-w plate at $2–1\times10^5$ cell/well. Increasing concentrations of t-PALP are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 33 t-PALP Biological Effects

Astrocyte and Neuronal Assays

Recombinant t-PALP, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate t-PALP's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of t-PALP to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or t-PALP with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or t-PALP with or without IL-1α for 24 hours. The supernatants are collected and assayed for IL-6 by ELISA kit (Endogen, Cambridge, Mass.).

Human lung fibroblasts are cultured with FGF-2 or t-PALP for 3 days in basal medium before the addition of Alamar Blue to assess effects on growth of the fibroblasts. FGF-2 should show a stimulation at 10–2500 ng/ml which can be used to compare stimulation with t-PALP.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine (MPP+) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, t-PALP can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of t-PALP is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if t-PALP acts to prolong the survival of dopaminergic neurons, it would suggest that t-PALP may be involved in Parkinson's Disease.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 34

The Effect of t-PALP on the Growth of Vascular Endothelial Cells

On day 1, human umbilical vein endothelial cells (HUVEC) are seeded at 2–5×$10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. t-PALP protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that t-PALP may proliferate vascular endothelial cells.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 35

Stimulatory Effect of t-PALP on the Proliferation of Vascular Endothelial Cells

For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or t-PALP in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 36

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36): 21985–21992 (1996).

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 37

Stimulation of Endothelial Migration

This example will be used to explore the possibility that t-PALP may stimulate lymphatic endothelial cell migration.

Endothelial cell migration assays are performed using a 48 well microchemotaxis chamber (Neuroprobe Inc., Cabin John, M D; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, 2.5×$10^5$ cells suspended in 50 ul M199 containing 1% FBS are seeded in the upper compartment. The apparatus is then incubated for 5 hours at 37° C. in a humidified chamber with 5% $CO_2$ to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 38

Stimulation of Nitric Oxide Production by Endothelial Cells

Nitric oxide released by the vascular endothelium is believed to be a mediator of vascular endothelium relaxation. Thus, t-PALP activity can be assayed by determining nitric oxide production by endothelial cells in response to t-PALP.

Nitric oxide is measured in 96-well plates of confluent microvascular endothelial cells after 24 hours starvation and a subsequent 4 hr exposure to various levels of a positive control (such as VEGF-1) and t-PALP. Nitric oxide in the medium is determined by use of the Griess reagent to measure total nitrite after reduction of nitric oxide-derived nitrate by nitrate reductase. The effect of t-PALP on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

$$2KNO_2+2KI+2H_2SO_462NO+I_2+2H_2O+2K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1\times10^6$ endothelial cells. All values reported are means of four to six measurements in each group (number of cell culture wells). See, Leak et al. *Biochem. and Biophys. Res. Comm.* 217: 96–105 (1995).

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 39

Effect of t-PALP on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or t-PALP (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. beta-esteradiol (1 ng/ml) is used as a negative control. The appropriate buffer (without protein) is also utilized as a control.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 40

Angiogenic Effect on Chick Chorioallantoic Membrane

Chick chorioallantoic membrane (CAM) is a well-established system to examine angiogenesis. Blood vessel formation on CAM is easily visible and quantifiable. The ability of t-PALP to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Using a protocol based on that of Brooks, et al. (See, *Cell* 79:1157–64 (1994); See also, Brooks, et al., *Cell* 92:391–400 (1998)), the effects of t-PALP on the growth of TSU cells were analyzed in a CAM assay. In this experiment, seven to ten day old eggs were candeled to locate the air sac and a window of egg shell approximately 2 cm×2 cm was opened right on the top of the CAM. Approximately $1\times10^6$ freshly harvested TSU cells either transfected with t-PALP or mock-transfected (with expression vector pcDNA3 only) were placed on the CAM. Transfections were performed as described in Example 51. The holes were sealed with parafilm and the eggs were placed in an incubator. Seven days later, the tumor mass on the CAM was carefully cut out and weighed. Fifteen to twenty eggs were used for each treatment and the mean +/− standard error of tumor mass (mg/CAM) was calculated. The resulting data were subjected to the student's t-test for statistical analysis.

In one experiment, the tumor mass associated with TSU cells transfected with vector only was approximately 80 mg/CAM and the tumor mass associated with TSU cells transfected with t-PALP was approximately 10 mg/CAM. These results suggest that t-PALP, and agonists of t-PALP, may play an inhibitory role in tumor growth. Moreover, it is likely that antagonists of t-PALP, for example, anti-t-PALP antibodies of the invention reduce the inhibitory effect of t-PALP on tumor growth.

Example 41

Angiogenesis Assay Using a Matrigel Implant in Mouse

In vivo angiogenesis assay of t-PALP measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with t-PALP at 150 ng/ml at 4 degree C. and drawn into cold 3 ml syringes. Female C57Bl/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 42

Rescue of Ischemia in Rabbit Lower Limb Model

To study the in vivo effects of t-PALP on ischemia, a rabbit hindlimb ischemia model is created by surgical removal of one femoral arteries as described previously (Takeshita, S. et al., *Am J Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J Pathol* 147: 1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked t-PALP expression plasmid by arterial gene transfer technology using a hydrogel-coated balloon catheter as described (Riessen, R. et al. *Hum Gene Ther.* 4:749–758 (1993); Leclerc, G. et al. *J. Clin. Invest.* 90: 936–944 (1992)). When t-PALP is used in the treatment, a single bolus of 500 mg t-PALP protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 43

Effect of t-PALP on Vasodilation

Since dilation of vascular endothelium is important in reducing blood pressure, the ability of t-PALP to affect the blood pressure in spontaneously hypertensive rats (SHR) is examined. Increasing doses (0, 10, 30, 100, 300, and 900 mg/kg) of the t-PALP are administered to 13–14 week old spontaneously hypertensive rats (SHR). Data are expressed as the mean +/− SEM. Statistical analysis are performed with a paired t-test and statistical significance is defined as $p<0.05$ vs. the response to buffer alone.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 44

Rat Ischemic Skin Flap Model

The evaluation parameters include skin blood flow, skin temperature, and factor VIII immunohistochemistry or endothelial alkaline phosphatase reaction. t-PALP expression, during the skin ischemia, is studied using in situ hybridization.

The study in this model is divided into three parts as follows:

a) Ischemic skin
b) Ischemic skin wounds
c) Normal wounds

The experimental protocol includes:

a) Raising a 3×4 cm, single pedicle full-thickness random skin flap (myocutaneous flap over the lower back of the animal).
b) An excisional wounding (4–6 mm in diameter) in the ischemic skin (skin-flap).
c) Topical treatment with t-PALP of the excisional wounds (day 0, 1, 2, 3, 4 post-wounding) at the following various dosage ranges: 1 mg to 100 mg.
d) Harvesting the wound tissues at day 3, 5, 7, 10, 14 and 21 post-wounding for histological, immunohistochemical, and in situ studies.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 45

Peripheral Arterial Disease Model

Angiogenic therapy using t-PALP is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.
b) t-PALP protein, in a dosage range of 20 mg–500 mg, is delivered intravenously and/or intramuscularly 3 times (perhaps more) per week for 2–3 weeks.
c) The ischemic muscle tissue is collected after ligation of the femoral artery at 1, 2, and 3 weeks for the analysis of t-PALP expression and histology. Biopsy is also performed on the other side of normal muscle of the contralateral hindlimb.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 46

Ischemic Myocardial Disease Model t-PALP is evaluated as a potent mitogen capable of stimulating the development of collateral vessels, and restructuring new vessels after coronary artery occlusion. Alteration of t-PALP expression is investigated in situ. The experimental protocol includes:

a) The heart is exposed through a left-side thoracotomy in the rat. Immediately, the left coronary artery is occluded with a thin suture (6-0) and the thorax is closed.
b) t-PALP protein, in a dosage range of 20 mg–500 mg, is delivered intravenously and/or intramuscularly 3 times (perhaps more) per week for 2–4 weeks.
c) Thirty days after the surgery, the heart is removed and cross-sectioned for morphometric and in situ analyzes.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 47

Rat Corneal Wound Healing Model

This animal model shows the effect of t-PALP on neovascularization. The experimental protocol includes:

a) Making a 1–1.5 mm long incision from the center of cornea into the stromal layer.
b) Inserting a spatula below the lip of the incision facing the outer corner of the eye.
c) Making a pocket (its base is 1–1.5 mm form the edge of the eye).
d) Positioning a pellet, containing 50 ng–5 ug of t-PALP, within the pocket.
e) t-PALP treatment can also be applied topically to the corneal wounds in a dosage range of 20 mg–500 mg (daily treatment for five days).

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 48

Diabetic Mouse and Glucocorticoid-Impaired Wound Healing Models

A. Diabetic db+/db+ Mouse Model.

To demonstrate that t-PALP accelerates the healing process, the genetically diabetic mouse model of wound healing is used. The full thickness wound healing model in the db+/db+mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., Lab Invest. 40(4):460–473 (1979); Coleman, D. L., *Diabetes* 31 (Suppl):1–6 (1982)). The homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl- 2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

t-PALP is administered using at a range different doses of t-PALP, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated; and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 $mm^2$, the corresponding size of the dermal punch. Calculations are made using the following formula:

[Open area on day8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with t-PALP. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., J. Clin. Invest. 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that t-PALP can accelerate the healing process, the effects of multiple topical applications of t-PALP on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

t-PALP is administered using at a range different doses of t-PALP, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) t-PALP treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with t-PALP. A calibrated lens micrometer is used by a blinded observer to determine the distance of the wound gap.

Experimental data are analyzed using an unpaired t test. A p value of <0.05 is considered significant.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 49

Lymphadema Animal Model

The purpose of this experimental approach is to create an appropriate and consistent lymphedema model for testing the therapeutic effects of t-PALP in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately 350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software (Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80EC until sectioning. Upon sectioning, the muscle is observed under fluorescent microscopy for lymphatics.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 50

Suppression of TNF Alpha-Induced Adhesion Molecule Expression by t-PALP

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of t-PALP to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 μl of 0.1% paraformaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 μl of diluted primary antibody to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed X3 with PBS (+Ca,Mg)+0.5% BSA.

Then add 20 μl of diluted ExtrAvidin-Alkaline Phosphotase (1:5,000 dilution) to each well and incubated at 37° C. for 30 min. Wells are washed X3 with PBS(+Ca,Mg)+0.5% BSA. 1 tablet of p-Nitrophenol Phosphate pNPP is dissolved in 5 ml of glycine buffer (pH 10.4). 100 μl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$0.5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4 h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity in t-PALP protein. However, one skilled in the art could easily modify the exemplified studies to test the activity of t-PALP polynucleotides (e.g., gene therapy), agonists, and/or antagonists of t-PALP.

Example 51

Effect of Conditioned Medium from t-PALP Transfectants on Endothelial Cells

Conditioned medium from TSU cells was removed following transient transfection with a pcDNA3/t-PALP expression construct. One hundred micrograms of the pcDNA3/t-PALP or pcDNA vector plasmid DNAs were transfected into $1\times10^6$ cells in 100 mm dishes by the CaPO4 method. Transfected cultures were maintained in 10% calf serum-DMEM (Biofluids, Rockville, Md.) containing 800 mg/ml of G418. Clones surviving the G418 selection were pooled and Northern analysis was performed to confirm expression. Aliquots of either 50, 100 or 200 microliters of the conditioned medium was added to the culture medium of endothelial cells. Treated cultures were then incubated at 37° C. The number of cells in each culture was then determined.

Endothelial cell cultures which were treated with 50 or 100 microliters of conditioned medium from TSU cells transfected with t-PALP exhibited no significant effect on the number of cells in the culture. However, endothelial cell cultures which were treated with 200 microliters of conditioned medium from TSU cells transfected with t-PALP contained less cells than endothelial cell cultures which were treated with control conditioned medium. In one experiment approximately 180,000 cells were counted in endothelial cell cultures treated with control conditioned medium as compared to 120,000 cells counted in endothelial cell cultures treated with conditioned medium from TSU cells transfected with t-PALP.

Such a decrease in endothelial cell number in cultures treated with conditioned medium from TSU cell cultures transfected with t-PALP suggests that t-PALP may play a role in endothelial cell growth. Because t-PALP may play a role in endothelial cell growth, it is likely that t-PALP, agonists and/or antagonists thereof, may play a role as mediators of angiogenesis. t-PALP polypeptides and agonists of the invention may function to inhibit angiogenesis, whereas antagonists of t-PALP, for example, anti-t-PALP antibodies of the invention, may function to increase angiogenesis.

Example 52

Effect of t-PALP on Tumor Growth in Nude Mice

The ability of t-PALP to inhibit tumor growth may be assessed by monitoring the growth rate of tumors in nude mice. TSU cells transfected with t-PALP cDNA or mock transfected cells were harvested with 10 mM EDTA-PBS. Transfections were performed as described in Example 51. One million tumor cells suspended in 0.2 ml of DMEM per side was injected subcutaneously into 5 week old nude mice (Taconic, Germantown, N.Y.). Five mice were used in each group. The tumor size was measured twice a week. The mice were sacrificed 4 weeks later and the tumors were removed and weighed and measured. The mean +/− standard error were calculated and the data were subjected to student t-test for statistical analysis.

In one experiment, the mean tumor volumes ($cm^3$) for nude mice injected with mock-transfected tumor cells as compared to nude mice injected with a t-PALP expression vector construct are as follows:

| Days Post-injection | Mock Tumor Vol. | t-PALP Tumor Vol. |
|---|---|---|
| 3 | 0.03 | 0.015 |
| 9 | 0.075 | <0.01 |
| 12 | 0.09 | <0.01 |
| 16 | 0.13 | <0.01 |

Thus, animals which were injected with tumor cells transfected with the mock control developed tumors increasing in volume over time from approximately 0.03 $cm^3$ to approximately 0.13 $cm^3$ from day 3 post-injection to day 16 post-injection, respectively. Conversely, animals which were injected with tumor cells transfected with a t-PALP expression vector developed tumors increasing in volume over time from approximately 0.03 $cm^3$ to approximately 0.13 $cm^3$ from day 3 post-injection to day 16 post-injection, respectively.

t-PALP may therefore play a regulatory role in tumorigenesis and/or agiogenesis t-PALP, and agonists thereof, may inhibit angiogenesis and/or tumor growth, while antagonists of t-PALP, for example, anti-t-PALP antibodies of the invention, may reduce or block the inhibitory effect of t-PALP with respect to angiogenesis and/or tumorigenesis.

Example 53

Anchorage-Dependenat and Anchorage-Independent Cell Growth Assay

In this assay, twenty thousand cells were transfected with pcDNA3 expression vector alone or with pcDNA3/t-PALP and were seeded in a 24 well plate with 1 ml of 10% calf serum-DMEM. Medium was changed every other day. Transfections were performed as described in Example 51. The cells were harvested with 1 ml of 10 mM-PBS at day 1, 3, 5, 7, and 9 and counted with a Coulter counter. In anchorage-dependent growth assay, twenty thousand transfectants in 10% calf serum-DMEM were mixed with 0.36% agar and immediately placed on top of 0.6% bottom layer agar in the same media. Three weeks later, the colonies formed in the soft agar were quantified using an Omnicon Image Analysis system (Imaging Products International Inc, Chantilly, Va.).

Example 54

Immunohistochemical Staining of Vessels in Tumors Formed by t-PALP Transfectants Transfections of pcDNA3 and pcDNA3-t-PALP were performed as described in Example 51 and injected into nude mice as described in Example 52. The tumors formed by mock transfectants and pcDNA3-t-PALP transfectants were immersed into liquid nitrogen immediately after harvested from animals. The frozen sections (10 mm thick) were fixed with aceton and air dry. The sections were stained with 1:500 rabbit anti-factor VIII (a marker of endothelium, DAKO Inc.) and 1:10 Paris (a mouse monoclonal antibody specific to chicken endothelium), followed by correspondent ABC kits (containing biotinylated secondary antibody and strepavidin conjugated peroxidase) and AEC substrate (yield a red color). The number of vessels in 10 random fields were counted.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a polynucleotide selected from the group consisting of:

(a) a nucleotide sequence encoding the t-PALP polypeptide having the amino acid sequence at positions −21 to 242 of SEQ ID NO:2;

(b) a nucleotide sequence encoding the t-PALP polypeptide having the amino acid sequence at positions −20 to 242 of SEQ ID NO:2;

(c) a nucleotide sequence encoding the mature t-PALP polypeptide having the amino acid sequence at positions 1 to 242 in SEQ ID NO:2;

(d) a nucleotide sequence encoding the protease domain of the t-PALP polypeptide having the amino acid sequence at positions 64 to 242 in SEQ ID NO:2;

(e) a nucleotide sequence encoding the complete amino acid sequence encoded by the cDNA clone contained in ATCC Deposit No. 209023;

(f) a nucleotide sequence encoding the complete amino acid sequence excepting the N-terminal methionine encoded by the cDNA clone contained in ATCC Deposit No. 209023;

(g) a nucleotide sequence encoding the mature t-PALP polypeptide encoded by the cDNA clone contained in the ATCC Deposit No. 209023;

(h) a nucleotide sequence encoding the protease domain of the t-PALP polypeptide encoded by the cDNA clone contained in the ATCC Deposit No. 209023; and (i) a nucleotide sequence completely complementary to any of the complete nucleotide sequences in (a), (b), (c), (d), (e), (f), (g), or (h) above.

2. A method for making a recombinant vector comprising inserting an isolated nucleic acid molecule of claim 1 into a vector.

3. A recombinant vector produced by the method of claim 2.

4. A method of making an isolated recombinant host cell comprising introducing the recombinant vector of claim 3 into a host cell.

5. An isolated recombinant host cell produced by the method of claim 4.

6. A recombinant method for producing a t-PALP polypeptide, comprising culturing the recombinant host cell of claim 5 under conditions such that said polypeptide is expressed and recovering said polypeptide.

7. The isolated nucleic acid molecule of claim 1 which comprises polynucleotide sequence (a).

8. The isolated nucleic acid molecule of claim 1 which comprises polynucleotide sequence (b).

9. The isolated nucleic acid molecule of claim 1 which comprises polynucleotide sequence (c).

10. The isolated nucleic acid molecule of claim 1 which comprises polynucleotide sequence (d).

11. The isolated nucleic acid molecule of claim 1 which comprises polynucleotide sequence (e).

12. The isolated nucleic acid molecule of claim 1 which comprises polynucleotide sequence (f).

13. The isolated nucleic acid molecule of claim 1 which comprises polynucleotide sequence (g).

14. The isolated nucleic acid molecule of claim 1 which comprises polynucleotide sequence (h).

15. The isolated nucleic acid molecule of claim 1 wherein the polynucleotide sequence further comprises a heterologous polynucleotide sequence.

16. The isolated nucleic acid molecule of claim 15 wherein the heterologous polynucleotide encodes a heterologous polypeptide.

17. The isolated nucleic acid molecule of claim 16 wherein the heterologous polypeptide is the Fc domain of immunoglobulin, a hexa-histidine peptide, or a FLAG polypeptide.

18. A composition comprising the polynucleotide of claim 1 and a carrier.

19. An isolated nucleic acid molecule consisting of a nucleotide sequence encoding the kringle domain of the t-PALP polypeptide consisting of the amino acid sequence at positions 4 to 63 in SEQ ID NO:2.

20. An isolated nucleic acid molecule consisting of a nucleotide sequence encoding the kringle domain of the t-PALP polypeptide encoded by the cDNA clone contained in the ATCC Deposit No. 209023.

* * * * *